(12) United States Patent
Alevizos et al.

(10) Patent No.: US 8,785,414 B2
(45) Date of Patent: Jul. 22, 2014

(54) DIFFERENTIALLY EXPRESSED MICRORNAS AS BIOMARKERS FOR THE DIAGNOSIS AND TREATMENT OF SJÖGREN'S SYNDROME

(75) Inventors: Ilias Alevizos, Chevy Chase, MD (US); Gabor Illei, Rockville, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 90 days.

(21) Appl. No.: 13/262,125

(22) PCT Filed: Mar. 31, 2010

(86) PCT No.: PCT/US2010/029307
§ 371 (c)(1),
(2), (4) Date: Sep. 29, 2011

(87) PCT Pub. No.: WO2010/117829
PCT Pub. Date: Oct. 14, 2010

(65) Prior Publication Data
US 2012/0029056 A1    Feb. 2, 2012

Related U.S. Application Data

(60) Provisional application No. 61/165,142, filed on Mar. 31, 2009.

(51) Int. Cl.
*A61K 31/70* (2006.01)
*C07H 21/02* (2006.01)
*C07H 21/04* (2006.01)
*C12Q 1/68* (2006.01)

(52) U.S. Cl.
USPC ...... 514/44 A; 514/44 R; 536/23.1; 536/24.2; 536/24.5; 435/375; 435/377

(58) Field of Classification Search
None
See application file for complete search history.

(56) References Cited

U.S. PATENT DOCUMENTS

| | | |
|---|---|---|
| 2006/0019286 A1 | 1/2006 | Horvitz et al. |
| 2006/0185027 A1 | 8/2006 | Bartel et al. |
| 2008/0306006 A1 | 12/2008 | Croce et al. |
| 2008/0306017 A1 | 12/2008 | Croce et al. |
| 2010/0286249 A1* | 11/2010 | Mohapatra et al. ......... 514/44 R |
| 2011/0151460 A1* | 6/2011 | Klass et al. .................. 435/6.11 |

FOREIGN PATENT DOCUMENTS

| | | |
|---|---|---|
| WO | WO 2006/137941 | 12/2006 |
| WO | WO 2007/112754 | 10/2007 |
| WO | WO 2008/147974 | 12/2008 |

OTHER PUBLICATIONS

Ambros et al., "A Uniform System for microRNA Annotation," *RNA*, vol. 9:277-279, 2003.
Bhanji et al., "Clinical and Serological Features of Patients with Autoantibodies to GW/P Bodies," *Clin. Immunol.*, vol. 125(3):247-256, 2007.
Cai et al., "Epstein-Barr Virus MicroRNAs are Evolutionarily Conserved and Differentially Expressed," *PLoS Pathogens*, vol. 2(3):0236-0247, 2006.
Carsons, "A Review and Update of Sjögren's Syndrome: Manifestations, Diagnosis, and Treatment," *Am. J. Manag. Care*, vol. 7(14):S433-S443, 2001.
Dai et al., "Microarray Analysis of MicroRNA Expression in Peripheral Blood Cells of Systemic Lupus Erythematosus Patients," *Lupus*, vol. 16:939-946, 2007.
Edwards et al., Epstein-Barr Virus BART MicroRNAs are Produced from a Large Intron Prior to Splicing, *J. Virol.*, vol. 82(18):9094-9106, 2008.
Griffiths-Jones, "The microRNA Registry," *Nucleic Acids Res.*, vol. 32:D109-D111, 2004.
Griffiths-Jones et al., "miRBase: microRNA Sequences, Targets and Gene Nomenclature," *Nucleic Acids Res.* vol. 34:D140-D144, 2006.
Giffiths-Jones et al., "miRBase: Tools for microRNA Genomics," *Nucleic Acids Res.*, vol. 36:D154-D158, 2008.
Langerman et al., "Utility of Lip Biopsy in the Diagnosis and Treatment of Sjogren's Syndrome," *Laryngoscope*, vol. 117:1004-1008, 2007.
Michael et al., "Exosomes from human saliva as a source of microRNA biomarkers," *Oral Diseases*, vol. 16:34-38, 2009.
Murphy et al., "Suppression of Immediate-Early Viral Gene Expression by Herpesvirus-Coded microRNAs: Implications for Latency," *Proc. Natl. Acad. Sci. USA*, vol. 105(14):5453-5458, 2008.
Nakasa et al., "Expression of MicroRNA-146 in Rheumatoid Arthritis Synovial Tissue," *Arthritis Rheum.*, vol. 58(5):1284-1292, 2008.
Pauley et al., "Upregulated miR-146a Expression in Peripheral Blood Mononuclear Cells from Rheumatoid Arthritis Patients," *Arthritis Res. Ther.*, vol. 10:R101-R110, 2008.

(Continued)

*Primary Examiner* — Sean McGarry
(74) *Attorney, Agent, or Firm* — Klarquist Sparkman, LLP

(57) ABSTRACT

The identification of differentially expressed microRNAs in patients with Sjögren's syndrome is disclosed herein. Provided is a method of diagnosing a subject as having Sjögren's syndrome by measuring the level of at least one differentially expressed miR gene product identified herein. An alteration in the level of the at least one miR gene product in the biological sample of the subject relative to a control indicates the subject has Sjögren's syndrome. Also provided is a method of treating a patient with Sjögren's syndrome by administering to the patient a therapeutically effective amount of an agent that inhibits expression of a miR gene product that is up-regulated in the patient with Sjögren's syndrome relative to a control, or by administering to the patient a therapeutically effective amount of an isolated miR gene product that is down-regulated in the patient with Sjögren's syndrome relative to a control. A method of restoring salivary flow in a patient with Sjögren's syndrome is also provided.

12 Claims, 6 Drawing Sheets

(56) References Cited

OTHER PUBLICATIONS

Samols et al., "Cloning and Identification of a MicroRNA Cluster within the Latency-Associated Region of Kaposi's Sarcoma-Associated Herpesvirus," *J. Virol.*, vol. 79(14):9301-9305, 2005.

Stanczyk et al., Altered Expression of MicroRNA in Synovial Fibroblasts and Synovial Tissue in Rheumatoid Arthritis, *Arthritis Rheum.*, vol. 58(4):1001-1009, 2008.

Tili et al., "MicroRNAs, the Immune System and Rheumatic Disease," *Nat. Clinical Practice Rheumatology*, vol. 4(10):534-541, 2008.

Wang et al., "Direct and Sensitive miRNA Profiling from Low-Input Total RNA," *RNA*, vol. 13:151-159, 2007.

Ach et al., "Measuring microRNAs: Comparisons of Microarray and Quantitative PCR Measurements, and of Different Total RNA Prep Methods," *BMC Biotechnol.*, vol. 8:69-84, 2008.

Alevizos et al., "MicroRNAs in Sjögren's Syndrome as a Prototypic Autoimmune Disease," *Autoimmun. Rev.*, vol. 9:618-621, 2010.

Alevizos et al., "MicroRNA Expression Profiles as Biomarkers of Minor Salivary Gland Inflammation and Dysfunction in Sjögren's Syndrome," *Arthritis & Rheum.*, vol. 63:535-544, 2011.

Kapsogeorgou et al., "Cellular MicroRNAs (miRNAs) and Sjögren's Syndrome: Candidate Regulators of Autoimmune Response and Autoantigen Expression," *J. Autoimmun.*, vol. 37:129-135, 2011.

Worley et al., "Micro-RNAs Associated with Metastasis in Uveal Melanoma Identified by Multiplexed Microarray Profiling," *Melanoma Res.*, vol. 18:184-190, 2008.

Zhang et al., "An Array-Based Analysis of MicroRNA Expression Comparing Matched Frozen and Formalin-Fixed Paraffin-Embedded Human Tissue Samples," *J. Mol. Diagn.*, vol. 10:513-519, 2008.

\* cited by examiner

FIG. 2A

Housekeeper microRNAs identified from the minor salivary gland microarray analysis

| microRNA Array Identifier | Mature microRNA ID |
|---|---|
| hsa-let-7a | MIMAT0000062 |
| hsa-let-7b | MIMAT0000063 |
| hsa-let-7c | MIMAT0000064 |
| hsa-let-7d | MIMAT0000065 |
| hsa-let-7f | MIMAT0000067 |
| hsa-let-7g | MIMAT0000414 |
| hsa-miR-107 | MIMAT0000104 |
| hsa-miR-125b | MIMAT0000423 |
| hsa-miR-151 | MIMAT0000757 |
| hsa-miR-15b | MIMAT0000417 |
| hsa-miR-17-5p | MIMAT0000070 |
| hsa-miR-20b | MIMAT0001413 |
| hsa-miR-218 | MIMAT0000275 |
| hsa-miR-23a | MIMAT0000078 |
| hsa-miR-26a | MIMAT0000082 |
| hsa-miR-26b | MIMAT0000083 |
| hsa-miR-29a | MIMAT0000086 |
| hsa-miR-320 | MIMAT0000510 |
| hsa-miR-331 | MIMAT0000760 |
| hsa-miR-345 | MIMAT0000772 |
| hsa-miR-34a | MIMAT0000255 |
| hsa-miR-34b | MIMAT0000685 |
| hsa-miR-361 | MIMAT0000703 |
| hsa-miR-365 | MIMAT0000710 |
| hsa-miR-660 | MIMAT0003338 |
| hsa-miR-98 | MIMAT0000096 |
| hsa-miR-99a | MIMAT0000097 |

FIG. 2B

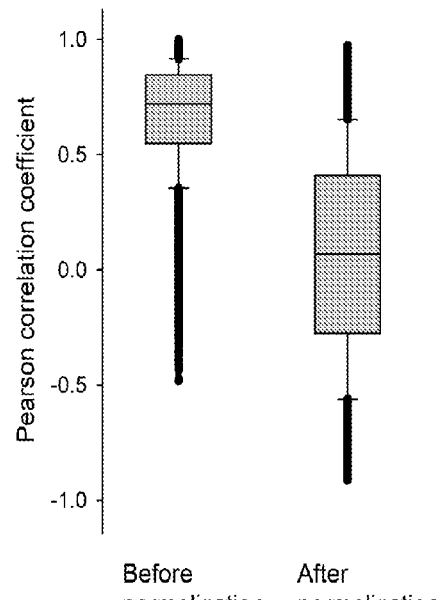

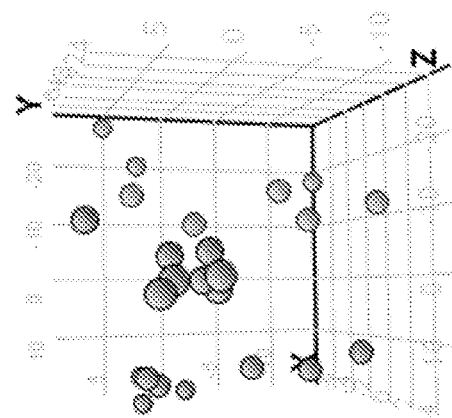
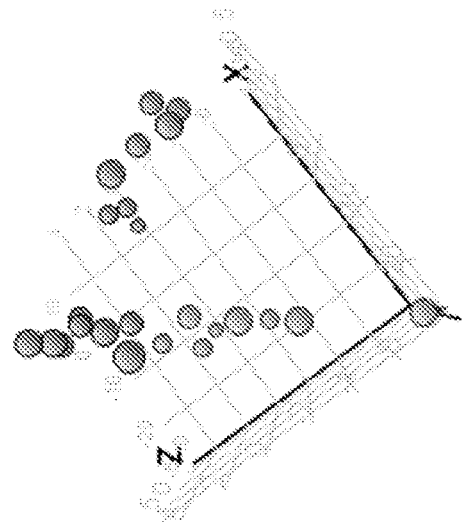
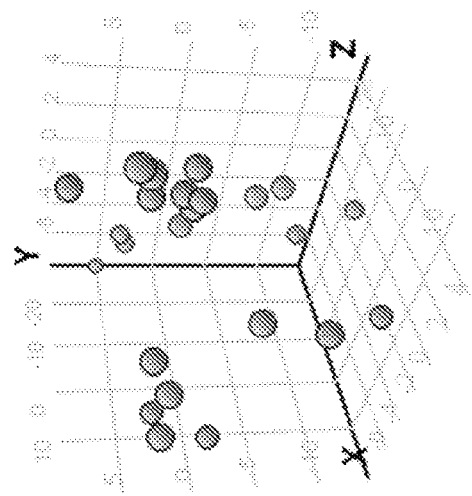
FIG. 3

DIFFERENTIALLY EXPRESSED MICRORNAS AS BIOMARKERS FOR THE DIAGNOSIS AND TREATMENT OF SJÖGREN'S SYNDROME

CROSS REFERENCE TO RELATED APPLICATIONS

This application is the U.S. National Stage of International Application No. PCT/US2010/029307, filed Mar. 31, 2010, published in English under PCT Article 21(2), which claims the benefit of U.S. Provisional Application No. 61/165,142, filed Mar. 31, 2009, which is herein incorporated by reference in its entirety.

FIELD

This disclosure concerns microRNAs that are differentially expressed in patients with Sjögren's syndrome compared with healthy individuals, and use of the disclosed microRNAs for the diagnosis and treatment of Sjögren's syndrome.

BACKGROUND

Sjögren's syndrome is an autoimmune disorder in which immune cells attack and destroy the glands that produce tears and saliva. The hallmark symptoms of the disorder are dry mouth and dry eyes. Sjögren's syndrome may also cause skin, nose and vaginal dryness, and can affect other organs of the body including the kidneys, blood vessels, lungs, liver, pancreas and brain. Sjögren's syndrome affects 1-4 million people in the United States, with women being nine times more likely to develop the disease. The majority of Sjögren's sufferers are at least 40 years old at the time of diagnosis. Sjögren's syndrome can occur as a primary condition or as a secondary disorder in association with other autoimmune diseases, such as systemic lupus erythematosus ("lupus") or rheumatoid arthritis.

Sjögren's syndrome can damage vital organs of the body with symptoms that may remain stable, worsen, or go into remission. Some patients experience only the mild symptoms of dry eyes and mouth, while others go through cycles of good health followed by severe disease. While many patients are able to treat problems symptomatically, others suffer from blurred vision, constant eye discomfort, recurrent mouth infections, swollen parotid glands, hoarseness, and difficulty in swallowing and eating. Debilitating fatigue and joint pain can seriously impair quality of life. The diagnosis of Sjögren's syndrome is made based on various combinations of subjective and objective evidence of dryness and the presence of markers of autoimmunity (autoantibodies) and/or inflammation in the salivary gland. More objective diagnostic biomarkers are highly desirable to improve the accuracy of Sjögren's syndrome diagnosis.

There is currently no known cure for Sjögren's syndrome, nor is there a universally effective treatment to restore gland secretion. Treatment is generally symptomatic and supportive, including moisture replacement therapies to relieve the symptoms of eye and mouth dryness. A subset of patients has some response to orally available drugs (pilocarpine and cevimeline) that stimulate saliva production but the response is usually limited and many patients do not tolerate the drugs due to side effects. Non-steroidal anti-inflammatory drugs can be used to treat musculoskeletal symptoms. For individuals with severe complications, corticosteroids or immunosuppressive drugs are often prescribed. These drugs can have serious side effects. Therefore, a need exists to not only accurately diagnose patients with Sjögren's syndrome, but to identify viable therapeutic targets for treatment of the disease.

SUMMARY

MicroRNAs (miRNAs or miRs) are small, single-stranded RNA molecules that regulate gene expression. It is disclosed herein that patients with Sjögren's syndrome exhibit differential miR gene expression as compared to healthy control subjects. It is further disclosed herein that a number of miRs are differentially expressed in Sjögren's syndrome patients with normal salivary flow relative to patients with low salivary flow, as well as in Sjögren's syndrome patients with a high focus score (high inflammation) and low focus score (low inflammation).

Thus, provided herein is a method of diagnosing a subject as having Sjögren's syndrome by measuring the level of at least one differentially expressed miR gene product identified herein. The method includes measuring the level of at least one miR gene product in a biological sample (such as a salivary gland biopsy or saliva) of a patient with Sjögren's syndrome. An alteration in the level of the at least one miR gene product in the biological sample of the subject, relative to a control, indicates the subject has Sjögren's syndrome. In some embodiments, the method further includes providing an appropriate therapy to the subject diagnosed with Sjögren's syndrome.

Also provided is a method of treating a patient with Sjögren's syndrome by administering to the patient a therapeutically effective amount of an agent that inhibits expression of a miR gene product that is up-regulated in the patient with Sjögren's syndrome relative to a control. Further provided is a method of treating a patient with Sjögren's syndrome by administering to the patient a therapeutically effective amount of an isolated miR gene product that is down-regulated in the patient with Sjögren's syndrome relative to a control.

A method of restoring salivary flow in a patient with Sjögren's syndrome is also provided. The method includes administering to the patient a therapeutically effective amount of an isolated miR gene product (or a combination of miR gene products) that is up-regulated in a normal salivary flow Sjögren's syndrome patient relative to a patient with low salivary flow. Alternatively, the method includes administering to the patient a therapeutically effective amount of an agent that inhibits expression of a miR gene product that is down-regulated in a normal salivary flow Sjögren's syndrome patient relative to a patient with low salivary flow.

Further provided is a method of diagnosing a Sjögren's syndrome patient as having a high or low focus score by measuring the level of at least one miR gene product associated with a high or low focus score in a biological sample of the subject.

The foregoing and other objects, features, and advantages of the invention will become more apparent from the following detailed description, which proceeds with reference to the accompanying figures.

BRIEF DESCRIPTION OF THE FIGURES

FIG. 2A is a table of housekeeper microRNAs used to normalize microarray data. FIG. 2B is a graph showing boxplots comparing the distributions of Pearson correlation coefficients for expression of all pairs of microRNAs over all microarrays before and after normalization to the housekeeping microRNAs as indicated. Only microRNAs that were scored as present by the Agilent Feature Extraction Software on all microarrays were included in the calculations.

FIG. 3 is a series of 3-dimensional plots showing the results of principal component analysis (PCA) of all 24 hybridized samples. The samples are plotted along their first three principal components. Three orientations of the PCA plot are shown. Non-SS minor salivary glands are represented by medium-sized circles, low focus score MSGs are represented by large circles and high focus score MSGs are represented by small circles. The plots were exported from GENE-SPRING™.

DETAILED DESCRIPTION

Figure 1:
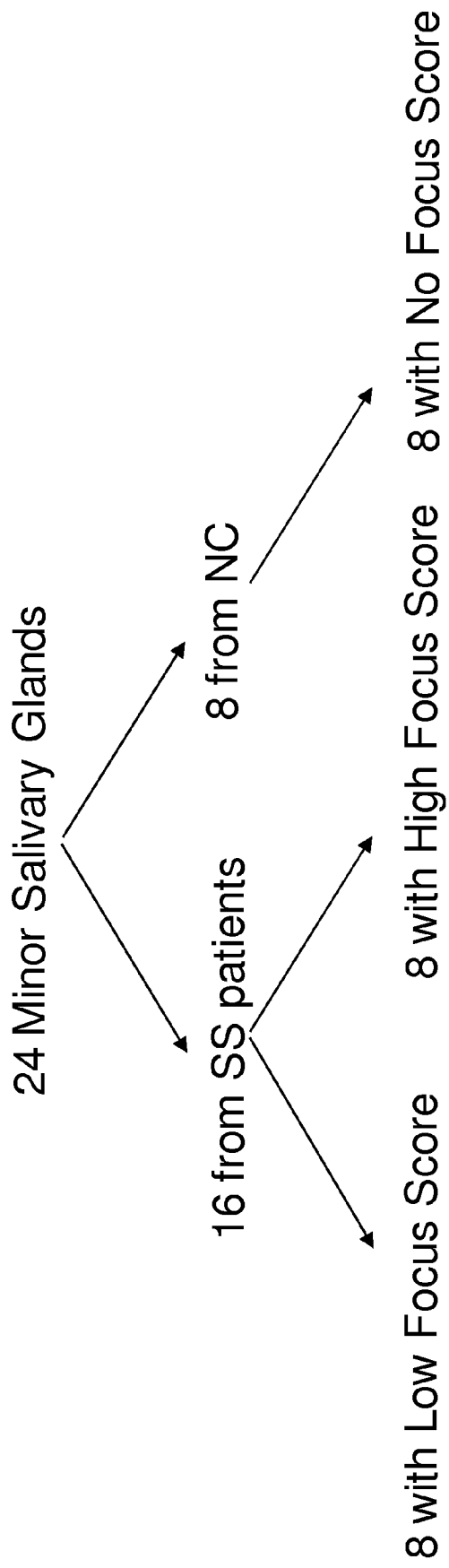
FIG. 1 is a schematic diagram of the minor salivary gland (MSG) classes used for microarray expression analysis. A total of 24 MSGs were used, 8 of which were biopsied from normal controls (NC) and 16 were obtained from Sjögren's syndrome (SS) patients. Eight of the 16 SS biopsies had a high focus score (12) and 8 SS biopsies had a low focus score ($\leq 2$).

I. Abbreviations ebv Epstein-Barr virus
FS Focus score
hcmv Human cytomegalovirus
hiv1 Human immunodeficiency virus-1
hsa *Homo sapiens*
hsv1 Herpes simplex virus-1
kshv Kaposi's sarcoma herpes virus
miR MicroRNA
miRNA MicroRNA
MSG Minor salivary gland
NC Normal control
NPV Negative predictive value
NSAID Non-steroidal anti-inflammatory drug
PCA Principal component analysis
PCR Polymerase chain reaction
PPV Positive predictive value
RNA Ribonucleic acid
siRNA Small interfering RNA
SS Sjögren's syndrome

II Terms and Methods

Unless otherwise noted, technical terms are used according to conventional usage. Definitions of common terms in molecular biology may be found in Benjamin Lewin, *Genes IX*, published by Jones and Bartlett Publishers, 2007 (ISBN 0763740632); Kendrew et al. (eds.), *The Encyclopedia of Molecular Biology*, published by Blackwell Science Inc., 1998; and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Administration: To provide or give a subject an agent, such as a therapeutic agent, by any effective route. Exemplary routes of administration include, but are not limited to, injection (such as subcutaneous, intramuscular, intradermal, intraperitoneal, and intravenous), oral, intraductal, sublingual, rectal, transdermal, intranasal, vaginal and inhalation routes.

Agent: Any protein, nucleic acid molecule (including chemically modified nucleic acids), compound, small molecule, organic compound, inorganic compound, or other molecule of interest. Agent can include a therapeutic agent, a diagnostic agent or a pharmaceutical agent. A therapeutic or pharmaceutical agent is one that alone or together with an additional compound induces the desired response (such as inducing a therapeutic or prophylactic effect when administered to a subject).

Agent that promotes salivary production: Any compound that increases the amount of saliva produced in a subject (for example, a subject with Sjögren's syndrome). In some cases, an agent that promotes salivary production is a therapeutic agent prescribed by a physician, such as pilocarpine (Salagen™) or cevimeline (Evoxac™). In some examples, the agent that promotes salivary production is a microRNA gene product, such as a gene product that is down-regulated in patients with Sjögren's syndrome relative to healthy subjects, or that is down-regulated in Sjögren's syndrome patients with low salivary flow compared with normal salivary flow Sjögren's syndrome patients.

Alteration in expression: An alteration in expression of a miR gene product refers to a change in the level of the miR gene product that is detectable in a biological sample (such as a sample from a patient with Sjögren's syndrome) relative to a control (such as a healthy subject). An "alteration" in expression includes an increase in expression (up-regulation) or a decrease in expression (down-regulation).

Antisense compound: Refers to an oligomeric compound that is at least partially complementary to the region of a target nucleic acid molecule (such as a miR gene product) to which it hybridizes. As used herein, an antisense compound that is "specific for" a target nucleic acid molecule is one which specifically hybridizes with and modulates expression of the target nucleic acid molecule. As used herein, a "target" nucleic acid is a nucleic acid molecule to which an antisense compound is designed to specifically hybridize and modulate expression. In some examples, the target nucleic acid molecule is a miR gene product.

Nonlimiting examples of antisense compounds include primers, probes, antisense oligonucleotides, siRNAs, miRNAs, shRNAs and ribozymes. As such, these compounds can be introduced as single-stranded, double-stranded, circular, branched or hairpin compounds and can contain structural elements such as internal or terminal bulges or loops. Double-stranded antisense compounds can be two strands hybridized to form double-stranded compounds or a single strand with sufficient self complementarity to allow for hybridization and formation of a fully or partially double-stranded compound. In particular examples herein, the antisense compound is an antisense oligonucleotide, siRNA or ribozyme.

Antisense oligonucleotide: As used herein, an "antisense oligonucleotide" is a single-stranded antisense compound that is a nucleic acid-based oligomer. An antisense oligonucleotide can include one or more chemical modifications to the sugar, base, and/or internucleoside linkages. Generally, antisense oligonucleotides are "DNA-like" such that when the antisense oligonucleotide hybridizes to a target RNA molecule, the duplex is recognized by RNase H (an enzyme that recognizes DNA:RNA duplexes), resulting in cleavage of the RNA.

Array: An arrangement of molecules, such as biological macromolecules (such nucleic acid molecules), in addressable locations on or in a substrate. A "microarray" is an array that is miniaturized so as to require or be aided by microscopic examination for evaluation or analysis. Arrays are sometimes called DNA chips or biochips.

The array of molecules ("features") makes it possible to carry out a very large number of analyses on a sample at one time. In certain example arrays, one or more molecules (such as an oligonucleotide probe) will occur on the array a plurality of times (such as twice), for instance to provide internal controls. The number of addressable locations on the array can vary, for example from at least 2, at least 5, at least 10, at least 14, at least 15, at least 20, at least 30, at least 50, at least 75, at least 100, at least 150, at least 200, at least 300, at least 500, least 550, at least 600, at least 800, at least 1000, at least 10,000, or more. In a particular example, an array includes 5-1000 addressable locations, such as 10-100 addressable locations. In particular examples, an array consists essentially of probes or primers (such as those that permit amplification) specific for the miR gene products listed in one or more of Tables 1-6 and 16-21.

Within an array, each arrayed sample is addressable, in that its location can be reliably and consistently determined within at least two dimensions of the array. The feature application location on an array can assume different shapes. For example, the array can be regular (such as arranged in uniform rows and columns) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays usually are computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

Biological sample: A biological specimen containing genomic DNA, RNA (including mRNA and microRNA), protein, or combinations thereof, obtained from a subject. Examples include, but are not limited to, saliva, peripheral blood, urine, tissue biopsy, surgical specimen, and autopsy material. In one example, a sample includes a biopsy of a salivary gland, such as from a patient with Sjögren's syndrome or a healthy control subject. In other embodiments, the biological sample is a saliva sample. In some examples, exosomes are isolated from the saliva and used as a source of miRNA. In other embodiments, the biological sample is blood, or a component thereof, such as plasma or serum.

Blood: The fluid that circulates through the heart, arteries, capillaries, and veins and is the chief means of transport (such as for transport of gases, metabolites and waste products) within the body. Blood is primarily composed of plasma (the fluid portion) and blood cells and platelets (the solid portion). "Plasma" refers to the fluid portion of the blood, in which the blood cells are suspended. Plasma is mostly water and contains plasma proteins, inorganic salts, nutrients, gases, waste materials from the cells, and various hormones, secretions and enzymes. "Serum" refers to the clear, straw-colored, liquid portion of the plasma that does not contain fibrinogen or blood cells, and remains fluid after clotting of blood.

Control: A "control" refers to a sample or standard used for comparison with an experimental sample, such as a salivary gland sample obtained from a patient with Sjögren's syndrome. In some embodiments, the control is a sample obtained from a healthy patient (also referred to herein as a "normal" control). In some embodiments, the control is a historical control or standard value (i.e. a previously tested control sample or group of samples that represent baseline or normal values).

Corticosteroids: Steroid hormones that are produced in the adrenal cortex. Corticosteroids are involved in a wide range of physiologic systems such as stress response, immune response and regulation of inflammation, carbohydrate metabolism, protein catabolism, blood electrolyte levels, and behavior. Examples of corticosteroids include cortisol and prednisone.

Diagnosis: The process of identifying a disease by its signs, symptoms and/or results of various tests. The conclusion reached through that process is also called "a diagnosis." Forms of testing commonly performed include blood tests, medical imaging, genetic analysis, urinalysis, and biopsy.

Diagnostically significant amount: As used herein a "diagnostically significant amount" refers to an increase or decrease in the level of a miR gene product in a biological sample that is sufficient to allow one to distinguish one patient population from another (such as a Sjögren's syndrome patient population from a group of healthy individuals). In some embodiments, the diagnostically significant increase or decrease is at least 2-fold, at least 3-fold, at least 4-fold, at least 5-fold, at least 6-fold, at least 8-fold, at least 10-fold, at least 15-fold, at least 20-fold, at least 30-fold or at least 40-fold. In some examples, the diagnostically significant amount is the fold-change in miR gene expression shown in Tables 1-6. A diagnostically significant amount can also be determined by calculating the fold-change in expression of a particular miR between two sample types (such as between a control subject and a Sjogren's syndrome patient, or between Sjogren's syndrome patients with a high focus score and a low focus score) shown in any one of Tables 16, 19 or 20. Microarray analysis is provided herein as one example of how miR gene product expression can be detected. However, one of skill in the art will recognize that other methods exist to measure gene expression (such as one of the methods described herein) and variation in detected expression levels can occur depending on the method that is used. Thus, the diagnostically significant amount may vary if another method of detection is used, such as RT-PCR.

Differential expression or altered expression of a microRNA: A difference, such as an increase or decrease, in the conversion of the information encoded in a microRNA gene into microRNA gene product. In some examples, the difference is relative to a control or reference value, such as an amount of microRNA expression in a sample from a healthy control subject.

Downregulated or decreased: When used in reference to the expression of a nucleic acid molecule (such as a microRNA), refers to any process which results in a decrease in production of a gene product. In the context of the present disclosure, a gene product can be a primary transcript microRNA (pri-miRNA), precursor microRNA (pre-miRNA), or mature microRNA. Gene downregulation includes any detectable decrease in the production of a microRNA gene product. In certain examples, production of a microRNA decreases by at least 2-fold, at least 3-fold, at least 4-fold, at least 5-fold, at least 6-fold, at least 8-fold, at least 10-fold, at least 15-fold, at least 20-fold, at least 30-fold or at least 40-fold, as compared to a control. In some examples, a control is a relative amount of microRNA expression in one or more subjects who do not have Sjögren's syndrome.

Exosomes: Small, right-side out cell-secreted vesicles of about 30-100 nm, derived from fusion of multivesicular bodies to plasma membranes. Exosomes are morphologically distinct from secreted microvesicles, which are larger (approximately 1 micron), and are instead derived from pinching off of the plasma membrane. Both microvesicles and exosomes retain cytoplasmic contents, but exosomes have characteristic surface markers, including CD63, CD9, CD81, and TSG101, not found on other secreted vesicle populations. Exosomes are derived from a wide range of cells, primarily hematopoietic cells such as reticulocytes, platelets, dendritic cells, B & T lymphocytes, and macrophages. However, exosomes are also secreted by various epithelial cells (such as alveolar lung tissue, tubule cells and podocytes from nephrons, and intestinal cells) and tumor cells.

Focus score: A measure of inflammation often used in the diagnosis of Sjögren's syndrome. Focus score is determined by measuring the number of lymphocytic foci (containing at least 50 inflammatory cells) in a 4 mm$^2$ glandular section. In some embodiments, a low focus score is a score of 0-4. In particular examples, a low focus score is a score of 0-2. In some embodiments, a high focus score is a score of 8 or greater. In particular examples, a high focus score is a score of 12 or greater.

Gene expression profile (or fingerprint or signature): Differential or altered gene expression can be detected by changes in the detectable amount of gene expression (such as mRNA or microRNA) or by changes in the detectable amount of proteins expressed by those genes. A gene expression profile is a distinct or identifiable pattern of gene expression, for instance a pattern of high and low expression of a defined set of genes. In some examples, as few as one or two genes or gene products provides a profile, but more genes or gene products can be used in a profile, for example at least 5, at least 10, at least 15, at least 20, at least 25, at least 30, at least 40 or at least 50. A gene expression profile (also referred to as a fingerprint or signature) can be linked to a tissue or cell type (such as a salivary gland), to a particular stage of a disease, or to any other distinct or identifiable condition that influences gene expression in a predictable way. Gene expression profiles can include relative as well as absolute expression levels of specific genes, and can be viewed in the context of a test sample compared to a baseline or control sample profile (such as a sample from a subject who does not have Sjögren's syndrome). In some examples, a gene expression profile in a subject is read on an array (such as a nucleic acid array).

Healthy control subject: A subject that is not clinically diagnosed with Sjögren's syndrome after an appropriate examination.

Hybridization: To form base pairs between complementary regions of two strands of DNA, RNA, or between DNA and RNA, thereby forming a duplex molecule. Hybridization conditions resulting in particular degrees of stringency will vary depending upon the nature of the hybridization method and the composition and length of the hybridizing nucleic acid sequences. Generally, the temperature of hybridization and the ionic strength (such as the Na$^+$ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:

Very High Stringency (detects sequences that share at least 90% identity)
Hybridization: 5×SSC at 65° C. for 16 hours
Wash twice: 2×SSC at room temperature (RT) for 15 minutes each
Wash twice: 0.5×SSC at 65° C. for 20 minutes each
High Stringency (detects sequences that share at least 80% identity)
Hybridization: 5×-6×SSC at 65° C.-70° C. for 16-20 hours
Wash twice: 2×SSC at RT for 5-20 minutes each
Wash twice: 1×SSC at 55° C.-70° C. for 30 minutes each
Low Stringency (detects sequences that share at least 60% identity)
Hybridization: 6×SSC at RT to 55° C. for 16-20 hours
Wash at least twice: 2×-3×SSC at RT to 55° C. for 20-30 minutes each.

Immunosuppressive drug: Includes any agent or compound having the ability to decrease the body's immune system responses. In some embodiments, the immunosuppressive drug is a corticosteroid. In other embodiments, the immunosuppressive drug is a small molecule (such as cyclosporine) or a monoclonal antibody (such as a cytokine blocker).

Isolated: An "isolated" biological component (such as a nucleic acid molecule, protein, or cell) has been substantially separated or purified away from other biological components in the cell or tissue of the organism, or the organism itself, in which the component naturally occurs, such as other chromosomal and extra-chromosomal DNA and RNA, proteins and cells. Nucleic acid molecules and proteins that have been "isolated" include those purified by standard purification methods. The term also embraces nucleic acid molecules and proteins prepared by recombinant expression in a host cell as well as chemically synthesized nucleic acid molecules and proteins.

Measuring the level of expression: As used herein, measuring the level of expression of a particular miR gene product refers to quantifying the amount of the miR gene product present in a sample. Quantification can be either numerical or relative. Detecting expression of the miR gene product can be achieved using any method known in the art or described herein, such as by RT-PCR. Detecting expression of a miR gene product includes detecting expression of either a mature form of the miR or a precursor form (i.e., a pri-miRNA or pre-miRNA) that is correlated with expression of the miR. Typically, miR detection methods involve sequence specific detection, such as by RT-PCR. miR-specific primers and probes can be designed using the precursor and mature miR nucleic acid sequences that are known in the art (the miRBase microRNA database is available online by the University of Manchester at www.mirbase.org).

In primary embodiments, the change detected is an increase or decrease in expression as compared to a control, such as a reference value or a healthy control subject. In some examples, the detected increase or decrease is an increase or decrease of at least two-fold compared with the control. In other examples, the detected increase or decrease is a change rounded down to the nearest whole number (so that both 2.05 and 2.67 are rounded down to 2) of the fold change shown for a miR in any of Tables 1-6, or is rounded to the nearest whole number (so that 2.05 would be rounded to 2 and 2.67 would be rounded to 3). In other embodiments of the methods, the increase or decrease is of a diagnostically significant amount, which refers to a change of a sufficient magnitude to provide a statistical probability of the diagnosis. In particular examples, the change is the magnitude of change shown in any of Tables 1-6, or the fold-change in the geometric mean of intensities between two samples shown in Tables 16, 19 or 20.

MicroRNA (miRNA or miR): A single-stranded RNA molecule that regulates gene expression in plants, animals and viruses. A gene encoding a microRNA is transcribed to form a primary transcript microRNA (pri-miRNA), which is processed to form a short stem-loop molecule, termed a precursor microRNA (pre-miRNA), followed by endonucleolytic cleavage to form the mature microRNA. Mature microRNAs are approximately 21-23 nucleotides in length and are partially complementary to the 3'UTR of one or more target messenger RNAs (mRNAs). The term "microRNA gene product" includes pri-miRNAs, pre-miRNAs and mature microRNAs (including minor mature miRNA species referred to as miR*).

MicroRNAs modulate gene expression by promoting cleavage of target mRNAs or by blocking translation of the cellular transcript. Thus far, over 900 unique human microRNAs (referred to as hsa-miR) have been identified. Numerous human viral miRs have also been identified, including miRs from Epstein-Barr virus (ebv-miR), Kaposi's sarcoma herpes virus (kshv-miR), herpes simplex virus-1 (hsv1-miR), human immunodeficiency virus-1 (hiv1-miR) and human cytomegalovirus (hcmv-miR). Viral miRs have been identified in human cells and, in some cases, have been linked to human disease, such as cancer.

As new microRNAs are identified, researchers register the sequences prior to publication of their work to ensure that each unique microRNA is assigned an official number (the miRBase Registry is available online through the University of Manchester at www.mirbase.org), eliminating any ambiguity in the literature regarding the identity of particular microRNAs. All miRs referred to by their miRBase registry numbers are herein incorporated by reference as they appear in the miRBase registry as of the filing date of this application. The miRBase registry also provides sequence information for known miRs.

Non-steroidal anti-inflammatory drug (NSAID): A type of anti-inflammatory agent that works by inhibiting the production of prostaglandins. NSAIDS exert anti-inflammatory, analgesic and antipyretic actions. Examples of NSAIDS include ibuprofen, ketoprofen, piroxicam, naproxen, sulindac, aspirin, choline subsalicylate, diflunisal, fenoprofen, indomethacin, meclofenamate, salsalate, tolmetin and magnesium salicylate.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Patient: As used herein, the term "patient" includes human and non-human animals. The preferred patient for treatment is a human. "Patient" and "subject" are used interchangeably herein.

Pharmaceutically acceptable vehicles: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds, molecules or agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease (such as Sjögren's syndrome) refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Prognosis: The likelihood of the clinical outcome for a subject afflicted with a specific disease or disorder. With regard to Sjögren's syndrome, the prognosis is a representation of the likelihood (probability) that the disease will progress (worsen) in a subject (develop more severe signs and/or symptoms of the disease). For example, a poor prognosis can indicate an increase in inflammation of the salivary glands, which can lead to mouth dryness, swallowing difficulties, dental decay, gum disease, mouth sores and swelling, infection of the parotid glands and dry lips. In some cases, a poor prognosis indicates swelling of other glands, such as those lining the breathing passages (leading to lung infections) and vagina (causing recurrent vaginal infections). A poor prognosis can also indicate extraglandular symptoms, such as joint pain or inflammation (arthritis), Raynaud's phenomenon, lung inflammation, lymph-node enlargement, kidney, nerve, or muscle disease, or inflammation of the blood vessels (vasculitis).

Recombinant: A recombinant nucleic acid molecule is one that has a sequence that is not naturally occurring or has a sequence that is made by an artificial combination of two otherwise separated segments of sequence. This artificial combination can be accomplished by chemical synthesis or by the artificial manipulation of isolated segments of nucleic acid molecules, such as by genetic engineering techniques.

Restoring salivary flow: Refers to the process of increasing salivary production in a subject with diminished salivary flow, such as may result from Sjögren's syndrome. In some embodiments, restoring salivary flow can be accomplished by administering a therapeutic agent. In some examples, the therapeutic agent is a pharmaceutical, such as pilocarpine (Salagen™) or cevimeline (Evoxac™). In other examples, the therapeutic agent is an isolated miR gene product that is down-regulated in patients with Sjögren's syndrome relative to healthy individuals, or is down-regulated in Sjögren's syndrome patients with low salivary flow compared with normal salivary flow Sjögren's syndrome patients.

Ribozyme: A catalytic RNA molecule. In some cases, ribozymes can bind to specific sites on other RNA molecules and catalyze the hydrolysis of phosphodiester bonds in the RNA molecules.

Salivary glands: Exocrine glands that produce saliva. As used herein, a "salivary gland" includes any salivary gland in a human subject, including, for example, the parotid glands, minor salivary glands, submandibular glands, sublingual glands and Von Ebner's glands. In particular examples, the salivary gland is a minor salivary gland or a parotid gland. There are over 600 minor salivary glands located throughout the oral cavity. Minor salivary glands are 1-2 mm in diameter. The parotid glands are a pair of glands located in the subcutaneous tissue of the face overlying the mandibular ramus and anterior and inferior to the external ear.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215: 403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI) and on the internet, for use in connection with the sequence analysis programs blastp, blastn, blastx, tblastn and tblastx. Additional information can be found at the NCBI web site.

Sialogogue medications: Orally available medications that increase saliva production by stimulating the muscarinic acetylcholine receptors. Currently, pilocarpine (Salagen™) and cevimeline (Evoxac™) are approved for this indication in the United States.

Sjögren's syndrome: An autoimmune disorder characterized by immune cells that attack and destroy the glands that produce tears and saliva. Sjögren's syndrome is not life-threatening or life-shortening, but can significantly reduce quality of life. The hallmark symptoms of the disorder are dry mouth and dry eyes. Sjögren's syndrome may also cause skin, nose and vaginal dryness, and can affect other organs of the body including the kidneys, blood vessels, lungs, liver, pancreas and brain. Sjögren's syndrome affects 1-4 million people in the United States, with women being nine times more likely to develop the disease. The majority of Sjögren's sufferers are at least 40 years old at the time of diagnosis. Sjögren's syndrome can occur as a primary condition or as a secondary disorder in association with a connective tissue disease, such as systemic lupus erythematosus ("lupus"), rheumatoid arthritis or scleroderma.

Small interfering RNA (siRNA): A double-stranded nucleic acid molecule that modulates gene expression through the RNAi pathway (see, for example, Bass, *Nature* 411:428-9, 2001; Elbashir et al., *Nature* 411:494-8, 2001; and PCT Publication Nos. WO 00/44895; WO 01/36646; WO 99/32619; WO 00/01846; WO 01/29058; WO 99/07409; and WO 00/44914). siRNA molecules are generally 20-25 nucleotides in length with 2-nucleotide overhangs on each 3' end. However, siRNAs can also be blunt ended. Generally, one strand of a siRNA molecule is at least partially complementary to a target nucleic acid, such as a target mRNA. siRNAs are also referred to as "small inhibitory RNAs," "small interfering RNAs" or "short inhibitory RNAs." As used herein, siRNA molecules need not be limited to those molecules containing only RNA, but further encompasses chemically modified nucleotides and non-nucleotides having RNAi capacity or activity. In an example, a siRNA molecule is one that reduces or inhibits the biological activity or expression of a miR gene product.

Subject: Living multi-cellular vertebrate organisms, a category that includes human and non-human mammals.

Therapeutic or therapy: A generic term that includes both diagnosis and treatment. Treatment refers to a prescribed course of action (including administration of therapeutic agents) to alter the normal course of a disorder.

Therapeutic agent: A chemical compound, small molecule, or other composition, such as an antisense compound, antibody, protease inhibitor, hormone, chemokine or cytokine, capable of inducing a desired therapeutic or prophylactic effect when properly administered to a subject.

Therapeutically effective amount: A quantity of a specified pharmaceutical or therapeutic agent sufficient to achieve a desired effect in a subject, or in a cell, being treated with the agent. The effective amount of the agent will be dependent on several factors, including, but not limited to the subject or cells being treated, and the manner of administration of the therapeutic composition.

Upregulated or activated: When used in reference to the expression of a nucleic acid molecule (such as a microRNA), refers to any process which results in an increase in production of a gene product. In the context of the present disclosure, a gene product can be a primary transcript microRNA (pri-miRNA), precursor microRNA (pre-miRNA), or mature microRNA. Gene upregulation includes any detectable increase in the production of a microRNA gene product. In certain examples, production of a microRNA increases by at least 2-fold, at least 3-fold, at least 4-fold, at least 5-fold, at least 6-fold, at least 8-fold, at least 10-fold, at least 15-fold, at least 20-fold, at least 30-fold or at least 40-fold, as compared to a control. In some examples, a control is a relative amount of microRNA expression in one or more subjects who do not have Sjögren's syndrome.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of inserted gene or genes. In some embodiments herein, the vector is a plasmid vector. In other embodiments, the vector is a viral vector.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

Described herein is the identification of microRNAs that are differentially expressed in patients with Sjögren's syndrome compared with healthy control subjects. Also disclosed are microRNAs that are up-regulated in Sjögren's syndrome patients exhibiting normal salivary flow as compared to Sjögren's syndrome patients with low salivary flow. Using microarray expression analysis of 470 human and 64 human viral microRNAs, numerous microRNAs were identified that were up- or down-regulated at least 2-fold in Sjögren's syndrome patients relative to a control. In some cases, microRNA gene product expression was altered as much as 45-fold or 92-fold. Thus, by measuring expression of one or more of the differentially expressed microRNAs in a subject, one can diagnose a subject as having Sjögren's syndrome.

Provided herein is a method of diagnosing a subject as having Sjögren's syndrome by measuring the level of at least one microRNA (miR) gene product in a biological sample of the subject. In some embodiments, the at least one miR gene product includes any miR gene product listed in any one of Tables 1-6 and 16-21. In particular embodiments, the at least one miR gene product is a miR-150, ebv-miR-BART13, ebv-miR-BART19, miR-768-3p, miR-574, miR-513, miR-188, miR-202, hcmv-miR-US4, miR-565, miR-509, miR-154, miR-99b, miR-564, miR-30b or miR-409-3p gene product. An alteration in the level of the at least one miR gene product in the biological sample of the subject relative to a control indicates the subject has Sjögren's syndrome. As described herein, an increase in the level of miR-150, an increase in the level of ebv-miR-BART13, an increase in the level of ebv-miR-BART19, an increase in the level of miR-768-3p, a decrease in the level of miR-574, an increase in the level of miR-513, an increase in the level of miR-188, an increase in the level of miR-202, an increase in the level of hcmv-miR-US4, an increase in the level of miR-565, an increase in the level of miR-509, an increase in the level of miR-154, an increase in the level of miR-99b, an increase in the level of miR-564, an increase in the level of miR-30b or an increase in the level of miR-409-3p, or a combination thereof, in the biological sample of the subject with Sjögren's syndrome relative to a control, indicates the subject has Sjögren's syndrome. In some embodiments, the increase or decrease in the level of the miR gene product is of a diagnostically significant amount.

In some embodiments of the methods, the diagnostically significant increase or decrease in expression of the miR gene product is at least 2-fold. In other embodiments, the diagnostically significant increase or decrease is at least 3-fold. In some examples, miR-150 is increased at least 32-fold, ebv-miR-BART13 is increased at least 7-fold, ebv-miR-BART19 is increased at least 45-fold, miR-768-3p is increased at least 3-fold, miR-574 is decreased at least 4-fold, miR-513 is increased at least 6-fold, miR-188 is increased at least 2-fold, miR-202 is increased at least 2-fold, hcmv-miR-US4 is increased at least 2-fold, miR-565 is increased at least 6-fold, miR-509 is increased at least 2-fold, miR-154 is increased at least 2-fold, miR-99b is increased at least 2-fold, miR-564 increased at least 6-fold, miR-30b is increased at least 3-fold, or miR-409-3p is increased at least 2-fold, or a combination thereof, in the biological sample of the subject with Sjögren's syndrome relative to the control.

In other examples, miR-150 is increased at least 38-fold, ebv-miR-BART13 is increased at least 21-fold, ebv-miR-BART19 is increased at least 92-fold, miR-768-3p is increased at least 3-fold, miR-574 is decreased at least 2-fold, miR-513 is increased at least 16-fold, miR-188 is increased at least 7-fold, miR-202 is increased at least 5-fold, hcmv-miR-US4 is increased at least 6-fold, miR-565 is increased at least 7-fold, miR-509 is increased at least 18-fold, miR-154 is increased at least 3-fold, miR-99b is increased at least 5-fold, miR-564 increased at least 29-fold, miR-30b is increased at least 4-fold, or miR-409-3p is increased at least 3-fold, or a combination thereof, in the biological sample of the subject with Sjögren's syndrome relative to the control.

A diagnostically significant increase or decrease can also be determined from any one of Tables 1-6, 16, 19 or 20, which either provide a specific fold-change in miR expression, or provide geometric means of intensities between Sjögren's syndrome patients and normal controls (or high and low focus score Sjögren's syndrome patients), which can be used to calculate fold-change.

In other examples of the diagnostic method, the at least one miR gene product is a miR-150, miR-183, miR-494, miR-513, miR-548c, miR-564, miR-565, miR-585, miR-768-5p, miR-801, ebv-miR-BART13 or ebv-miR-BART19 gene product. As described herein, the level of miR-150 is increased, the level of miR-183 is decreased, the level of miR-494 is increased, the level of miR-513 is increased, the level of miR-548c is decreased, the level of miR-564 is increased, the level of miR-565 is increased, the level of miR-585 is decreased, the level of miR-768-5p is decreased, the level of miR-801 is increased, the level of ebv-miR-BART13 is increased, and/or the level of ebv-miR-BART19 is increased in the subject with Sjögren's syndrome relative to the control.

In some cases, the at least one miR gene product is a miR-150, miR-183, miR-494, miR-513, miR-548c, miR- 564, miR-565, miR-585, miR-768-5p, miR-801, ebv-miR-BART13, ebv-miR-BART19, hsa-let-7d, hsa-let-7e, miR-125a, miR-148a or miR-32 gene product; and an increase in the level of miR-150, a decrease in the level of miR-183, an increase in the level of miR-494, an increase in the level of miR-513, a decrease in the level of miR-548c, an increase in the level of miR-564, an increase in the level of miR-565, a decrease in the level of miR-585, a decrease in the level of miR-768-5p, an increase in the level of miR-801, an increase in the level of ebv-miR-BART13, an increase in the level of ebv-miR-BART19, a decrease in the level of hsa-let-7d, a decrease in the level of hsa-let-7e, a decrease in the level of miR-125a, a decrease in the level of miR-148a or a decrease in the level of miR-32, or a combination thereof, in the biological sample of the subject with Sjögren's syndrome relative to a control, indicates the subject has Sjögren's syndrome.

In some embodiments, the method further includes measuring the level of one or more additional miR gene products. Accordingly, in some examples, the at least one miR gene product further comprises a miR-126, miR-189, miR-200c, miR-212, miR-22, miR-30b, miR-326, miR-328, miR-574, miR-575, miR-768-3p or miR-9 gene product, or a combination thereof. As taught herein, the level of miR-126 is increased, miR-189 is decreased, miR-200c is decreased, miR-212 is increased, miR-22 is decreased, miR-30b is increased, miR-326 is decreased, miR-328 is decreased, miR-574 is decreased, miR-575 is increased, miR-768-3p is increased and/or miR-9 is decreased in the subject with Sjögren's syndrome relative to the control.

In some embodiments of the methods, the diagnostically significant increase or decrease in expression of the miR gene product is at least 2-fold. In other embodiments, the diagnostically significant increase or decrease is at least 3-fold. In particular examples, miR-150 is increased at least 32-fold, miR-183 is decreased at least 7-fold, miR-494 is increased at least 6-fold, miR-513 is increased at least 6-fold, miR-548c is decreased at least 7-fold, miR-564 increased at least 6-fold, miR-565 is increased at least 6-fold, miR-585 is decreased at least 10-fold, miR-768-5p is decreased at least 8-fold, miR-801 is increased at least 7-fold, ebv-miR-BART13 is increased at least 7-fold, ebv-miR-BART19 is increased at least 45-fold, miR-126 is increased at least 4-fold, miR-189 is decreased at least 4-fold, miR-200c is decreased at least 3-fold, miR-212 is increased at least 4-fold, miR-22 is decreased at least 3-fold, miR-30b is increased at least 3-fold, miR-326 is decreased at least 3-fold, miR-328 is decreased at least 4-fold, miR-574 is decreased at least 4-fold, miR-575 is increased at least 4-fold, miR-768-3p is increased at least 3-fold or miR-9 is decreased at least 3-fold, hsa-let-7d is decreased at least 2-fold, hsa-let-7e is decreased at least 2-fold, miR-125a is decreased at least 2-fold, miR-148a is decreased at least 2-fold, or miR-32 is decreased at least 2-fold, or a combination thereof, in the biological sample of the subject with Sjögren's syndrome relative to the control.

It is understood that the methods disclosed herein include measuring the level of any single miR gene product, or any combination or subcombination of the miR gene products listed in Tables 1-6 or 16-21. In particular examples, the combination of miR gene products includes miR-150, ebv-miR-BART13, ebv-miR-BART19, miR-768-3p, miR-574, miR-513, miR-188, miR-202, hcmv-miR-US4, miR-565, miR-509, miR-154, miR-99b, miR-564, miR-30b and miR-409-3p, or any subcombination thereof. In other examples, the combination of miR gene products includes miR-150, miR-768-3p, miR-574, miR-513, miR-188, ebv-miR-BART19, miR-501, miR-126*, miR-342, miR-330, miR-135b, miR-142-5p and miR-650, or any subcombination thereof. In other examples, the combination of miR gene products includes miR-150, miR-585 and ebv-miR-BART19, or any subcombination thereof. In other examples, the combination of miR gene products includes miR-150, miR-183, miR-548c, miR-585, miR-768-5p, miR-801, ebv-miR-BART13 and ebv-miR-BART19, or any subcombination thereof. In other examples, the combination of miR gene products includes miR-150, miR-183, miR-494, miR-513, miR-548c, miR-564, miR-565, miR-585, miR-768-5p, miR-801, ebv-miR-BART13 and ebv-miR-BART19, or any subcombination thereof. In other examples, the combination of miR gene products includes miR-126, miR-150, miR-183, miR-189, miR-200c, miR-212, miR-22, miR-30b, miR-326, miR-328, miR-494, miR-513, miR-548c, miR-564, miR-565, miR-574, miR-575, miR-585, miR-768-3p, miR-768-5p, miR-801, miR-9, ebv-miR-BART13 and ebv-miR-BART19, or any subcombination thereof. In other examples, the combination of miR gene products includes miR-150, miR-183, miR-494, miR-513, miR-548c, miR-564, miR-565, miR-585, miR-768-5p, miR-801, ebv-miR-BART13, ebv-miR-BART19, hsa-let-7d, hsa-let-7e, miR-125a, miR-148a and miR-32, or any subcombination thereof.

In some cases, the method includes measuring the level of a single miR gene product. In one example, the single miR gene product is miR-574. In another example, the single miR gene product is ebv-miR-BART-13. In another example, the single miR gene product is ebv-miR-BART19. In another example, the single miR gene product is miR-150. In another example, the single miR gene product is miR-768-3p. In another example, the single miR gene product is miR-574. In another example, the single miR gene product is miR-513. In another example, the single miR gene product is miR-188. In another example, the single miR gene product is miR-202. In another example, the single miR gene product is hcmv-miR-US4. In another example, the single miR gene product is miR-565. In another example, the single miR gene product is miR-509. In another example, the single miR gene product is miR-154. In another example, the single miR gene product is miR-99b. In another example, the single miR gene product is miR-564. In another example, the single miR gene product is miR-30b. In another example, the single miR gene product is miR-409-3p. In another example, the single miR gene product is miR-183. In another example, the single miR gene product is miR-548c. In another example, the single miR gene product is miR-585. In another example, the single miR gene product is miR-768-5p. In another example, the single miR gene product is miR-801.

Methods of detecting and measuring miR expression are well known in the art and are described in detail below. In some examples, RT-PCR is used to measure the level of a miR gene product, such as when a single miR gene product is analyzed. In other cases, when multiple miR gene products are to be measured, it is desirable to use microarray analysis.

The miR gene product measured can be a primary miRNA (pri-miRNA) precursor miRNA (pre-miRNA), or a mature miRNA (including minor mature miRNA products denoted miR*).

In some embodiments of the methods, the biological sample is a salivary gland, such as a minor salivary gland or a parotid salivary gland. In some cases it is desirable to obtain a sample from the minor salivary gland as the biopsy procedure for this type of gland is less intrusive. In other embodiments, the biological sample is saliva. It has been determined that microRNAs can be isolated from exosomes found within the saliva (Michael et al., *Oral Dis.* 16:34-38, 2010). Thus, in some examples, microRNAs are isolated from exosomes of a saliva sample. In some embodiments, the biological sample is blood, or a component thereof, such as plasma or serum.

In some embodiments, the method further includes providing an appropriate therapy for the subject diagnosed with Sjögren's syndrome. In some examples, the therapy includes administering an agent that promotes salivary production. Such agents are known in the art, including pilocarpine or cevimeline. In other examples, the therapy includes administering a corticosteroid, such as cortisol or prednisone. In other examples, the therapy includes administering an immunosuppressive drug, such as a small molecule (e.g. cyclosporine) or a monoclonal antibody (e.g. a cytokine blocker). In other examples, the therapy includes administering an isolated miR gene product, such a miR gene product that has been identified as down-regulated in Sjögren's syndrome patients relative to a control, or down-regulated in Sjögren's syndrome patients with low salivary flow relative to normal salivary flow Sjögren's syndrome patients. In other examples, the therapy includes administering an agent that inhibits expression of a miR gene product, such as an agent that inhibits a miR gene product identified as up-regulated in Sjögren's syndrome patients relative to a control, or up-regulated in Sjögren's syndrome patients with low salivary flow relative to normal salivary flow Sjögren's syndrome patients.

Also provided herein is a method of treating a patient with Sjögren's syndrome by administering to the patient a therapeutically effective amount of an agent that inhibits expression of a miR gene product that is up-regulated in the patient with Sjögren's syndrome relative to a control, or by administering to the patient a therapeutically effective amount of an isolated miR gene product that is down-regulated in the patient with Sjögren's syndrome relative to a control.

In some embodiments, the miR gene product up-regulated in Sjögren's syndrome patients is any gene product listed in Table 1 or Table 2 that is categorized as "down" in the regulation column (which indicates decreased expression in normal subjects). In some embodiments, the up-regulated miR gene product is any miR gene product listed in Table 3 that is categorized as "up" in the regulation column (which indicates increased expression in low salivary flow Sjögren's syndrome patients relative to healthy subjects). In some embodiments, the miR gene product up-regulated in Sjögren's syndrome patients is any gene product listed in Table 16, 19 or 20, wherein the geometric mean of intensities value in the Sjögren's syndrome patient is greater than the value in the normal control. In particular embodiments, the up-regulated miR gene product is a miR-150, ebv-miR-BART13, ebv-miR-BART19, miR-768-3p, miR-513, miR-188, miR-202, hcmv-miR-US4, miR-565, miR-509, miR-154, miR-99b, miR-564, miR-30b, or miR-409-3p gene product. In other examples, the up-regulated miR gene product is a miR-126, miR-150, miR-212, miR-30b, miR-494, miR-513, miR-564, miR-565, miR-575, miR-768-3p, miR-801, ebv-miR-BART13 or ebv-miR-BART19 gene product. The agent can be any compound, such as a nucleic acid molecule, polypeptide, small molecule or other compound that is capable of inhibiting expression of one or more miR gene products. In some embodiments, the agent that inhibits expression of a miR gene product is an antisense compound specific for the miR gene product. In some examples, the antisense compound is an antisense oligonucleotide, siRNA or ribozyme.

In some embodiments, the miR gene product down-regulated in Sjögren's syndrome patients is any gene product listed in Table 1 or Table 2 that is categorized as "up" in the regulation column (which indicates increased expression in normal subjects). In some embodiments, the down-regulated miR gene product is any miR gene product listed in Table 3 that is categorized as "down" in the regulation column (which indicates decreased expression in low salivary flow Sjögren's syndrome patients relative to healthy subjects). In some embodiments, the miR gene product down-regulated in Sjögren's syndrome patients is any gene product listed in Table 16, 19 or 20, wherein the geometric mean of intensities value in the Sjögren's syndrome patient is less than the value in the normal control. In particular embodiments, the down-regulated miR gene product is a miR-183, miR-189, miR-200c, miR-22, miR-326, miR-328, miR-548c, miR-574, miR-585, miR-768-5p or a miR-9 gene product. In particular examples, the down-regulated miR gene product is a miR-574 gene product. In some examples, administration of the isolated miR gene product comprises administering a vector encoding the miR gene product, such as a plasmid vector or a viral vector. In other embodiments, the isolated miR gene product can be delivered, for example, as naked miR or using a liposomal formulation (e.g., the miR can be encapsulated in a liposome), cationic lipids or a polypeptide carrier.

Further provided herein is a method of restoring salivary flow in a patient with Sjögren's syndrome by administering to the patient a therapeutically effective amount of an isolated miR gene product. In some embodiments, the miR gene product is any miR gene product listed in Table 4 or Table 5 that is categorized as "up" in the regulation column (which indicates up-regulation in normal salivary flow Sjögren's syndrome patients relative to low salivary flow patients). In particular embodiments, the miR gene product is a miR-150, ebv-miR-BART13, ebv-miR-BART19, miR-768-3p, miR-574, miR-513, miR-188, miR-202, hcmv-miR-US4, miR-565, miR-509, miR-154, miR-99b, miR-564, miR-30b or miR-409-3p gene product. In other examples, the miR gene product is a miR-136, miR142-3p, miR-144, miR-19a, miR-212, miR-219, miR-301, miR-33, miR-330 or miR-340 gene product. In some embodiments, the isolated miR gene product comprises administering a vector encoding the miR gene product, such as a viral vector or plasmid vector. In other embodiments, the isolated miR gene product can be delivered, for example, as naked miR or using a liposomal formulation (e.g., the miR can be encapsulated in a liposome), cationic lipids or a polypeptide carrier.

Further provided is the use of the expression level of at least one miR gene product in a biological sample of a subject for the diagnosis of the subject as having Sjögren's syndrome and/or the treatment of the subject with Sjögren's syndrome, wherein the at least one miR gene product is a miR-150, ebv-miR-BART13, ebv-miR-BART19, miR-768-3p, miR-574, miR-513, miR-188, miR-202, hcmv-miR-US4, miR-565, miR-509, miR-154, miR-99b, miR-564, miR-30b or miR-409-3p gene product, and wherein: (i) an increase in the level of miR-150, an increase in the level of ebv-miR-BART13, an increase in the level of ebv-miR-BART19, an increase in the level of miR-768-3p, a decrease in the level of miR-574, an increase in the level of miR-513, an increase in the level of miR-188, an increase in the level of miR-202, an increase in the level of hcmv-miR-US4, an increase in the level of miR-565, an increase in the level of miR-509, an increase in the level of miR-154, an increase in the level of miR-99b, an increase in the level of miR-564, an increase in the level of miR-30b or an increase in the level of miR-409-3p, or a combination thereof; in the biological sample of the subject relative to a control, indicates the subject has Sjögren's syndrome, wherein the increase or decrease is of a diagnostically significant amount; and/or (ii) administering to the patient a therapeutically effective amount of an agent that inhibits expression of a miR gene product that is up-regulated in the patient with Sjögren's syndrome relative to a control, or by administering to the patient a therapeutically effective amount of an isolated miR gene product that is down-regulated in the patient with Sjögren's syndrome relative to a control. In some embodiments, the use further comprises providing an appropriate therapy or a second appropriate therapy for the subject diagnosed with Sjögren's syndrome.

Also provided is the use of a therapeutically effective amount of an agent that inhibits expression of a miR gene product that is up-regulated in the patient with Sjögren's syndrome relative to a control, or a therapeutically effective amount of an isolated miR gene product that is down-regulated in the patient with Sjögren's syndrome relative to a control, in the preparation of a medicament for the treatment of a patient with Sjögren's syndrome.

A therapeutically effective amount of an agent that inhibits expression of a miR gene product that is up-regulated in the patient with Sjögren's syndrome relative to a control, or a therapeutically effective amount of an isolated miR gene product that is down-regulated in the patient with Sjögren's syndrome relative to a control for use in a method for the treatment of Sjögren's syndrome or in a method for restoring salivary flow in a patient with Sjögren's syndrome, is further provided.

Use of a therapeutically effective amount of an isolated miR gene product in the preparation of a medicament for restoring salivary flow in a patient with Sjögren's syndrome, wherein the miR gene product is a miR-150, ebv-miR-BART13, ebv-miR-BART19, miR-768-3p, miR-574, miR-513, miR-188, miR-202, hcmv-miR-US4, miR-565, miR-509, miR-154, miR-99b, miR-564, miR-30b or miR-409-3p gene product, is also provided.

Also provided is a method of diagnosing a Sjögren's syndrome patient as having a high or low focus score, which is a measure of inflammation. In some embodiments, the method includes measuring the level of at least on miR gene product in a biological sample of the subject. The at least one miR gene product can be any miR gene product listed in any one of Tables 6, 19 or 20. For example, Table 6 shown miRs that are differentially expressed between low and high focus score Sjögren's syndrome patients. Tables 19 and 20 provide the geometric mean of intensities between high focus score Sjögren's syndrome patients, low focus score Sjögren's syndrome patients and normal controls for the miRs shown.

In some examples, the at least one miR gene product is a miR-150, miR-768-3p, miR-574, miR-513, miR-188, ebv-miR-BART19, miR-501, miR-126*, miR-342, miR-330, miR-135b, miR-142-5p, or miR-650 gene product. An increase in the level of miR-150, an increase in the level of miR-768-3p, a decrease in the level of miR-574, an increase in the level of miR-513, an increase in the level of miR-188, an increase in the level of ebv-miR-BART19, an increase in the level of miR-501, an increase in the level of miR-126*, an increase in the level of miR-342, an increase in the level of miR-330, an increase in the level of miR-135b, an increase in the level of miR-142-5p or an increase in the level of miR-650, or a combination thereof, in the biological sample of the patient with Sjögren's syndrome relative to a control, indicates the Sjögren's syndrome patient has a high focus score. In addition, or alternatively, a decrease in the level of miR-150, a decrease in the level of miR-768-3p, an increase in the level of miR-574, a decrease in the level of miR-513, a decrease in the level of miR-188, a decrease in the level of ebv-miR-BART19, a decrease in the level of miR-501, a decrease in the level of miR-126*, a decrease in the level of miR-342, a decrease in the level of miR-330, a decrease in the level of miR-135b, a decrease in the level of miR-142-5p or a decrease in the level of miR-650, or a combination thereof, in the biological sample of the patient with Sjögren's syndrome relative to a control, indicates the Sjögren's syndrome patient has a low focus score.

In some embodiments, the increase or decrease is of a diagnostically significant amount. In some embodiments, the diagnostically significant increase or decrease in the level of the miR gene product is at least 2-fold, at least 3-fold, at least 4-fold or at least 5-fold.

In other embodiments, the method includes measuring the level of at least one miR gene product in a biological sample of the subject, wherein the at least one miR gene product is a miR-150, miR-338, miR-219, miR-142-5p, miR-142-3p, miR-155, miR-650, miR-146b, miR-181a, miR-200a, miR-223, miR-299-3p, miR-375 or miR-377 gene product. An increase in the level of miR-142-3p, an increase in the level of miR-142-5p, an increase in the level of miR-146b, an increase in the level of miR-150, an increase in the level of miR-155, an increase in the level of miR181a, a decrease in the level of miR-200a, a decrease in the level of miR-219, an increase in the level of miR-223, a decrease in the level of miR-299-3p, a decrease in the level of miR-338, a decrease in the level of miR-375, a decrease in the level of miR-377 or an increase in the level of miR-650, or a combination thereof, in the biological sample of the patient with Sjögren's syndrome relative to a control, indicates the Sjögren's syndrome patient has a high focus score. In contrast, a decrease in the level of miR-142-3p, a decrease in the level of miR-142-5p, a decrease in the level of miR-146b, a decrease in the level of miR-150, a decrease in the level of miR-155, a decrease in the level of miR181a, an increase in the level of miR-200a, an increase in the level of miR-219, a decrease in the level of miR-223, an increase in the level of miR-299-3p, an increase in the level of miR-338, an increase in the level of miR-375, an increase in the level of miR-377 or a decrease in the level of miR-650, or a combination thereof, in the biological sample of the patient with Sjögren's syndrome relative to a control, indicates the Sjögren's syndrome patient has a low focus score.

For the diagnosis and treatment methods disclosed herein, the control can be any suitable control, such as a reference value. For example, the reference value (or values if more than one miR gene product is measured) can be an historical value based on average expression of the miR gene product in Sjögren's syndrome patients, including Sjögren's syndrome patients known to have either a high or low focus score. The control can also be a biological sample from a healthy subject (a subject that has not been diagnosed with Sjögren's syndrome).

Also provided herein is an in vitro process for screening therapeutic agents for the treatment of Sjögren's syndrome, comprising: (i) contacting a cell culture with a candidate agent; and (ii) measuring the level of at least one miR gene product selected from miR-150, ebv-miR-BART13, ebv-miR-BART19, miR-768-3p, miR-574, miR-513, miR-188, miR-202, hcmv-miR-US4, miR-565, miR-509, miR-154, miR-99b, miR-564, miR-30b and miR-409-3p gene product, wherein a decreases in the level of miR-150, ebv-miR-BART13, ebv-miR-BART19, miR-768-3p, miR-513, miR-188, miR-202, hcmv-miR-US4, miR-565, miR-509, miR-154, miR-99b, miR-564, miR-30b and/or miR-409-3p and/or an increase in the level of miR-574 relative to a control identifies a candidate agent as a therapeutic agent for the treatment of Sjögren's syndrome.

Also provided is the use of the expression level of at least one miR gene product for screening therapeutic agents for the treatment of a patient with Sjögren's syndrome, wherein the at least one miR gene product is a miR-150, ebv-miR-BART13, ebv-miR-BART19, miR-768-3p, miR-574, miR-513, miR-188, miR-202, hcmv-miR-US4, miR-565, miR-509, miR-154, miR-99b, miR-564, miR-30b or miR-409-3p gene product, and wherein an agent that decreases the level of miR-150, ebv-miR-BART13, ebv-miR-BART19, miR-768-3p, miR-513, miR-188, miR-202, hcmv-miR-US4, miR-565, miR-509, miR-154, miR-99b, miR-564, miR-30b or miR-409-3p and/or increases the level of miR-574 is a therapeutic agent for the treatment of Sjögren's syndrome.

An array comprising at least two oligonucleotides that specifically hybridize with a miR gene product selected from the miR gene products listed in any one of Tables 1-6 and 16-21 is also provided. In some embodiments, the array comprises at least two oligonucleotides that specifically hybridize with a miR gene product selected from the group consisting of miR-150, ebv-miR-BART13, ebv-miR-BART19, miR-768-3p, miR-574, miR-313, miR-188, miR-202, hcmv-miR-US4, miR-565, miR-509, miR-154, miR-99b, miR-564, miR-30b and miR-409-3p. Further provided is the use of such arrays for selecting an appropriate therapy for a subject with Sjögren's syndrome. The arrays can also be used to monitor the course of a selected therapy to determine whether the therapy is effective for the treatment of Sjögren's syndrome, as evidence by an increase or decrease in the level of one or more miRs associated with Sjögren's syndrome, as disclosed herein.

Also provided are kits comprising at least two oligonucleotide probes specific for a miR gene product selected from the miR gene products listed in any one of Tables 1-6 and 16-21. In some embodiments, the kits comprise at least two oligonucleotide probes specific for a miR gene product selected from the group consisting of miR-150, ebv-miR-BART13, ebv-miR-BART19, miR-768-3p, miR-574, miR-513, miR-188, miR-202, hcmv-miR-US4, miR-565, miR-509, miR-154, miR-99b, miR-564, miR-30b and miR-409-3p.

IV. MicroRNA Nomenclature and Nucleotide Sequences

MicroRNAs (also known as miRNAs and miRs) are short RNA sequences expressed from longer transcripts found in the genomes of animals, plants and viruses and at least one single-celled eukaryote (Molnár et al., Nature 447:1126-1129, 2007; Zhao et al., Genes Dev. 21:1190-1203, 2007). MicroRNAs regulate the expression of target genes by binding to complementary sites in the target gene transcripts to cause translational repression or transcript degradation (Pillai et al., Trends Cell Biol. 17:118-126, 2007). These small RNA molecules have been implicated in a number of biological processes related to development, cell proliferation, apoptosis, metabolism, morphogenesis and disease (particularly cancer) (Kloosterman and Plasterk, Dev. Cell 11:441-450, 2006).

A gene encoding a microRNA is transcribed to form a primary transcript microRNA (pri-miRNA), which is processed to form a short stem-loop molecule, termed a precursor microRNA (pre-miRNA), followed by endonucleolytic cleavage to form the mature microRNA. Mature microRNAs are approximately 21-23 nucleotides in length and are partially complementary to the 3'UTR of one or more target messenger RNAs (mRNAs).

A nomenclature scheme has been well established for microRNAs (Griffiths-Jones et al., Nucleic Acids Res. 34:D140-D144, 2006; Ambros et al., RNA 9:277-279, 2003; Griffiths-Jones, Nucleic Acids Res. 32:D109-D111, 2004). For example, a microRNA name includes a three or four letter species prefix, such as "hsa" for Homo sapiens, and a numeric suffix, such as "150," resulting in a complete name of "hsa-miR-150." Mature miRNA sequences expressed from more than one hairpin precursor molecule are distinguished by "-1" and "-2" (such as miR-6-1 and miR-6-2). Related hairpin loci expressing related mature microRNA sequences have lettered suffixes (such as miR-181a and miR-181b). In some cases, mature miRNAs from both the 5' and 3' arms of the hairpin precursor are identified, which are designated "3p" or "5p" (such as miR-768-3p and miR-768-5p). Viral microRNA names relate to the locus from which the microRNA is derived (for example, ebv-miR-BART1 is from the Epstein-Barr virus BART locus).

MicroRNA gene product sequences are well described throughout the scientific and patent literature and are available online through miRBase (www.mirbase.org), provided by the University of Manchester (previously provided by the Sanger Institute). The miRBase registry provides the nucleotide sequences of all published animal, plant and viral microRNAs (Griffiths-Jones et al., Nucleic Acids Res. 36:D154-D158, 2008). Provided by miRBase are the sequences of precursor microRNAs (stem-loop miRNAs), mature miRNAs and minor microRNA species (miR*). Precursor miRNAs predominantly express one species of miRNA, referred to as the mature miRNA. However, minor miRNA sequences have also been detected and are referred to as miR*.

V Methods for Detecting and Measuring MicroRNA Expression

MicroRNAs are noncoding RNA molecules with potential as biomarkers for diagnosis and prognosis of a variety of diseases (Calin et al., N Engl J Med 353:1793-801, 2005; Johnson et al., Cell 120:635-47, 2005; Volinia et al., Proc Natl Acad Sci USA 103:2257-61, 2006; Yanaihara et al., Cancer Cell 9:189-98, 2006; Cummins et al., Proc Natl Acad Sci USA 103:3687-92, 2006). Combining multiple prognostic biomarkers may improve the ability to diagnose and treat specific diseases, such as Sjögren's syndrome, compared to individual biomarkers. Thus, in some embodiments of the methods provided herein, microRNA expression profiles are used to diagnose Sjögren's syndrome and to predict the prognosis and develop potential therapies for patients with Sjögren's syndrome.

The sequences of precursor microRNAs and mature miRNAs are publicly available, such as through the miRBase database, available online by the University of Manchester, and formerly maintained by the Sanger Institute (see Griffiths-Jones et al., Nucleic Acids Res. 36:D154-D158, 2008; Griffiths-Jones et al., Nucleic Acids Res. 34:D140-D144, 2006; and Griffiths-Jones, Nucleic Acids Res. 32:D109-D111, 2004).

Detection and quantification of microRNA expression can be achieved by any one of a number of methods well known in the art (see, for example, U.S. Patent Application Publication Nos. 2006/0211000 and 2007/0299030). Using the known sequences for a microRNA of interest, specific probes and primers can be designed for use in the detection methods described herein as appropriate.

In some cases, the microRNA detection method requires isolation of nucleic acid from a sample, such as a cell, biological fluid sample or tissue sample (for example, a salivary gland or saliva). Nucleic acids, including RNA and specifically miRNA, can be isolated using any suitable technique known in the art. For example, phenol-based extraction is a common method for isolation of RNA. Phenol-based reagents contain a combination of denaturants and RNase inhibitors for cell and tissue disruption and subsequent separation of RNA from contaminants. Phenol-based isolation procedures can recover RNA species in the 10-200-nucleotide range (e.g., precursor and mature miRNAs, 5 S and 5.8 S ribosomal RNA (rRNA), and U1 small nuclear RNA (snRNA)). In addition, extraction procedures such as those using TRIZOL™ or TRI REAGENT™, will purify all RNAs, large and small, and are efficient methods for isolating total RNA from biological samples that contain miRNAs and siRNAs.

Microarray analysis of microRNAs can be accomplished according to any method known in the art (see, for example, PCT Publication No. WO 2008/054828; Ye et al., *Nat. Med.* 9(4):416-423, 2003; Calin et al., *N Engl. J. Med.* 353(17): 1793-1801, 2005). In one example, RNA is extracted from a cell or tissue sample, the small RNAs (18-26-nucleotide RNAs) are size-selected from total RNA using denaturing polyacrylamide gel electrophoresis. Oligonucleotide linkers are attached to the 5' and 3' ends of the small RNAs and the resulting ligation products are used as templates for an RT-PCR reaction with 10 cycles of amplification. The sense strand PCR primer has a fluorophore attached to its 5' end, thereby fluorescently labeling the sense strand of the PCR product. The PCR product is denatured and then hybridized to the microarray. A PCR product, referred to as the target nucleic acid that is complementary to the corresponding microRNA capture probe sequence on the array will hybridize, via base pairing, to the spot at which the capture probes are affixed. The spot will then fluoresce when excited using a microarray laser scanner. The fluorescence intensity of each spot is then evaluated in terms of the number of copies of a particular miRNA, using a number of positive and negative controls and array data normalization methods, which will result in assessment of the level of expression of a particular miRNA.

In an alternative method, total RNA containing the small RNA fraction (including the miRNA) extracted from a cell, biological fluid or tissue sample is used directly without size-selection of small RNAs, and 3' end labeled using T4 RNA ligase and either a fluorescently-labeled short RNA linker. The RNA samples are labeled by incubation at 30° C. for 2 hours followed by heat inactivation of the T4 RNA ligase at 80° C. for 5 minutes. The fluorophore-labeled miRNAs complementary to the corresponding miRNA capture probe sequences on the array will hybridize, via base pairing, to the spot at which the capture probes are affixed. The microarray scanning and data processing is carried out as described above.

Any one of a number of methods for detecting expression of a gene of interest (including microRNAs) known in the art can be used to detect expression of a microRNA. A number of these methods, including qRT-PCR, array, microarray, in situ hybridization, in situ PCR, SAGE are described in further detail below. miRNA detection can also be accomplished by deep sequencing, according to methods known in the art (Creighton et al., *Brief Bioinform.* 10(5):490-2009 Ma497, 2009).

A. RT-PCR

Methods for quantitating RNA, including microRNA, are well known in the art. In some embodiments, the method utilizes RT-PCR. Generally, the first step in gene expression profiling by RT-PCR is the reverse transcription of the RNA template into cDNA, followed by its exponential amplification in a PCR reaction. Two commonly used reverse transcriptases are avian myeloblastosis virus reverse transcriptase (AMV-RT) and Moloney murine leukemia virus reverse transcriptase (MMLV-RT). However, any suitable reverse transcriptase known in the art can be used for RT-PCR. The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif.), following the manufacturer's instructions. The derived cDNA can then be used as a template in the subsequent PCR reaction.

Although the PCR step can use a variety of thermostable DNA-dependent DNA polymerases, it often employs the Taq DNA polymerase, which has a 5'-3' nuclease activity but lacks a 3'-5' proofreading endonuclease activity. TaqMan® PCR typically utilizes the 5'-nuclease activity of Taq or Tth DNA polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TAQMAN® RT-PCR can be performed using commercially available equipment, such as, for example, ABI PRISM 7700® Sequence Detection System® (Perkin-Elmer-Applied Biosystems, Foster City, Calif.), or Lightcycler (Roche Molecular Biochemicals, Mannheim, Germany). In one example, the 5' nuclease procedure is run on a real-time quantitative PCR device such as the ABI PRISM 7700® Sequence Detection System®. The system includes of thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

To minimize errors and the effect of sample-to-sample variation, RT-PCR can be performed using an internal standard. The ideal internal standard is expressed at a constant level among different tissues, and is unaffected by the experimental treatment. RNAs commonly used to normalize patterns of gene expression are mRNAs for the housekeeping genes glyceraldehyde-3-phosphate-dehydrogenase (GAPDH), beta-actin, and 18 S ribosomal RNA.

The steps of a representative protocol for quantitating gene expression using fixed, paraffin-embedded tissues as the RNA source, including RNA isolation, purification, primer extension and amplification are given in various published journal articles (see Godfrey et al., *J. Mol. Diag.* 2:84 91, 2000; Specht et al., *Am. J. Pathol.* 158:419-29, 2001). Briefly, a representative process starts with cutting about 10 nm thick sections of paraffin-embedded tissue samples. The RNA is then extracted, and protein and DNA are removed. Alternatively, RNA is located directly from a tissue, cell or fluid sample. After analysis of the RNA concentration, RNA repair and/or amplification steps can be included, if necessary, and RNA is reverse transcribed using gene specific promoters followed by RT-PCR. The primers used for the amplification are selected so as to amplify a unique segment of the gene of interest, such as a microRNA. Primers that can be used to amplify a particular microRNA are commercially available (in some instance) or can be designed and synthesized according to well known methods using publically available sequences of the microRNA.

B. Serial Analysis of Gene Expression (SAGE)

SAGE is another method that allows the simultaneous and quantitative analysis of a large number of gene transcripts, without the need of providing an individual hybridization probe for each transcript. First, a short sequence tag (about 10-14 base pairs) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag (see, for example, Velculescu et al., *Science* 270:484-7, 1995; and Velculescu et al., *Cell* 88:243-51, 1997).

C. In Situ Hybridization (ISH)

ISH is another method for detecting and comparing expression of genes of interest. ISH applies and extrapolates the technology of nucleic acid hybridization to the single cell level, and, in combination with the art of cytochemistry, immunocytochemistry and immunohistochemistry, permits the maintenance of morphology and the identification of cellular markers to be maintained and identified, and allows the localization of sequences to specific cells within populations, such as tissues and blood samples. ISH is a type of hybridization that uses a complementary nucleic acid to localize one or more specific nucleic acid sequences in a portion or section of tissue (in situ), or, if the tissue is small enough, in the entire tissue (whole mount ISH). RNA ISH can be used to assay expression patterns in a tissue, such as the expression of microRNAs.

Sample cells or tissues are treated to increase their permeability to allow a probe, such as microRNA-specific probe, to enter the cells. The probe is added to the treated cells, allowed to hybridize at pertinent temperature, and excess probe is washed away. A complementary probe is labeled with a radioactive, fluorescent or antigenic tag, so that the probe's location and quantity in the tissue can be determined using autoradiography, fluorescence microscopy or immunoassay. The sample may be any sample as herein described, such as a salivary gland sample. Since the sequences of the microRNAs of interest are known, probes can be designed accordingly such that the probes specifically bind the gene of interest.

D. In Situ PCR

In situ PCR is the PCR based amplification of the target nucleic acid sequences prior to ISH. For detection of RNA, an intracellular reverse transcription step is introduced to generate complementary DNA from RNA templates prior to in situ PCR. This enables detection of low copy RNA sequences.

Prior to in situ PCR, cells or tissue samples are fixed and permeabilized to preserve morphology and permit access of the PCR reagents to the intracellular sequences to be amplified. PCR amplification of target sequences is next performed either in intact cells held in suspension or directly in cytocentrifuge preparations or tissue sections on glass slides. In the former approach, fixed cells suspended in the PCR reaction mixture are thermally cycled using conventional thermal cyclers. After PCR, the cells are cytocentrifuged onto glass slides with visualization of intracellular PCR products by ISH or immunohistochemistry. In situ PCR on glass slides is performed by overlaying the samples with the PCR mixture under a coverslip which is then sealed to prevent evaporation of the reaction mixture. Thermal cycling is achieved by placing the glass slides either directly on top of the heating block of a conventional or specially designed thermal cycler or by using thermal cycling ovens.

Detection of intracellular PCR products is generally achieved by one of two different techniques, indirect in situ PCR by ISH with PCR-product specific probes, or direct in situ PCR without ISH through direct detection of labeled nucleotides (such as digoxigenin-11-dUTP, fluorescein-dUTP, 3H-CTP or biotin-16-dUTP), which have been incorporated into the PCR products during thermal cycling.

E. Arrays for Profiling MicroRNA Expression

In particular embodiments provided herein, arrays can be used to evaluate microRNA expression, for example to diagnose or prognose Sjögren's syndrome. When describing an array that comprise probes or primers specific for a particular set of microRNAs (such as miR-126, miR-150, miR-183, miR-189, miR-200c, miR-212, miR-22, miR-30b, miR-326, miR-328, miR-494, miR-513, miR-548c, miR-564, miR-565, miR-574, miR-575, miR-585, miR-768-3p, miR-768-5p, miR-801, miR-9, ebv-miR-BART13 and ebv-miR-BART19), such an array includes probes or primers specific for the recited microRNAs, and can further include control probes (for example to confirm the incubation conditions are sufficient), and optionally probes for additional microRNAs. Exemplary control probes include GAPDH, actin, and YWHAZ. In one example, an array is a multi-well plate (e.g., 98 or 364 well plate).

In one example, the array includes, consists essentially of, or consists of probes or primers that can recognize miR-126, miR-150, miR-183, miR-189, miR-200c, miR-212, miR-22, miR-30b, miR-326, miR-328, miR-494, miR-513, miR-548c, miR-564, miR-565, miR-574, miR-575, miR-585, miR-768-3p, miR-768-5p, miR-801, miR-9, ebv-miR-BART13 and ebv-miR-BART19. The oligonucleotide probes or primers can further include one or more detectable labels, to permit detection of hybridization signals between the probe and target sequence (such as one of the microRNAs disclosed herein).

i. Array Substrates

The solid support of the array can be formed from an organic polymer. Suitable materials for the solid support include, but are not limited to: polypropylene, polyethylene, polybutylene, polyisobutylene, polybutadiene, polyisoprene, polyvinylpyrrolidine, polytetrafluoroethylene, polyvinylidene difluoroide, polyfluoroethylene-propylene, polyethylenevinyl alcohol, polymethylpentene, polycholorotrifluoroethylene, polysulfornes, hydroxylated biaxially oriented polypropylene, aminated biaxially oriented polypropylene, thiolated biaxially oriented polypropylene, etyleneacrylic acid, thylene methacrylic acid, and blends of copolymers thereof (see U.S. Pat. No. 5,985,567).

In general, suitable characteristics of the material that can be used to form the solid support surface include: being amenable to surface activation such that upon activation, the surface of the support is capable of covalently attaching a biomolecule such as an oligonucleotide thereto; amenability to "in situ" synthesis of biomolecules; being chemically inert such that at the areas on the support not occupied by the oligonucleotides or proteins (such as antibodies) are not amenable to non-specific binding, or when non-specific binding occurs, such materials can be readily removed from the surface without removing the oligonucleotides or proteins (such as antibodies).

In one example, the solid support surface is polypropylene. Polypropylene is chemically inert and hydrophobic. Non-specific binding is generally avoidable, and detection sensitivity is improved. Polypropylene has good chemical resistance to a variety of organic acids (such as formic acid), organic agents (such as acetone or ethanol), bases (such as sodium hydroxide), salts (such as sodium chloride), oxidizing agents (such as peracetic acid), and mineral acids (such as hydrochloric acid). Polypropylene also provides a low fluorescence background, which minimizes background interference and increases the sensitivity of the signal of interest.

In another example, a surface activated organic polymer is used as the solid support surface. One example of a surface activated organic polymer is a polypropylene material aminated via radio frequency plasma discharge. Such materials are easily utilized for the attachment of nucleotide molecules. The amine groups on the activated organic polymers are reactive with nucleotide molecules such that the nucleotide molecules can be bound to the polymers. Other reactive groups can also be used, such as carboxylated, hydroxylated, thiolated, or active ester groups.

ii. Array Formats

A wide variety of array formats can be employed in accordance with the present disclosure. One example includes a linear array of oligonucleotide bands, generally referred to in the art as a dipstick. Another suitable format includes a two-dimensional pattern of discrete cells (such as 4096 squares in a 64 by 64 array). As is appreciated by those skilled in the art, other array formats including, but not limited to slot (rectangular) and circular arrays are equally suitable for use (see U.S. Pat. No. 5,981,185). In some examples, the array is a multi-well plate. In one example, the array is formed on a polymer medium, which is a thread, membrane or film. An example of an organic polymer medium is a polypropylene sheet having a thickness on the order of about 1 mil. (0.001 inch) to about 20 mil., although the thickness of the film is not critical and can be varied over a fairly broad range. The array can include biaxially oriented polypropylene (BOPP) films, which in addition to their durability, exhibit a low background fluorescence.

The array formats of the present disclosure can be included in a variety of different types of formats. A "format" includes any format to which the solid support can be affixed, such as microliter plates (e.g. multi-well plates), test tubes, inorganic sheets, dipsticks, and the like. For example, when the solid support is a polypropylene thread, one or more polypropylene threads can be affixed to a plastic dipstick-type device; polypropylene membranes can be affixed to glass slides. The particular format is, in and of itself, unimportant. All that is necessary is that the solid support can be affixed thereto without affecting the functional behavior of the solid support or any biopolymer absorbed thereon, and that the format (such as the dipstick or slide) is stable to any materials into which the device is introduced (such as clinical samples and hybridization solutions).

The arrays of the present disclosure can be prepared by a variety of approaches. In one example, oligonucleotide sequences are synthesized separately and then attached to a solid support (see U.S. Pat. No. 6,013,789). In another example, sequences are synthesized directly onto the support to provide the desired array (see U.S. Pat. No. 5,554,501). Suitable methods for covalently coupling oligonucleotides to a solid support and for directly synthesizing the oligonucleotides onto the support are known to those working in the field; a summary of suitable methods can be found in Matson et al., Anal. Biochem. 217:306-10, 1994. In one example, the oligonucleotides are synthesized onto the support using conventional chemical techniques for preparing oligonucleotides on solid supports (such as see PCT applications WO 85/01051 and WO 89/10977, or U.S. Pat. No. 5,554,501).

A suitable array can be produced using automated means to synthesize oligonucleotides in the wells of the array by laying down the precursors for the four bases in a predetermined pattern. Briefly, a multiple-channel automated chemical delivery system is employed to create oligonucleotide probe populations in parallel rows (corresponding in number to the number of channels in the delivery system) across the substrate. Following completion of oligonucleotide synthesis in a first direction, the substrate can then be rotated by 90° to permit synthesis to proceed within a second (2°) set of rows that are now perpendicular to the first set. This process creates a multiple-channel array whose intersection generates a plurality of discrete cells.

The oligonucleotides can be bound to the polypropylene support by either the 3' end of the oligonucleotide or by the 5' end of the oligonucleotide. In one example, the oligonucleotides are bound to the solid support by the 3' end. However, one of skill in the art can determine whether the use of the 3' end or the 5' end of the oligonucleotide is suitable for bonding to the solid support. In general, the internal complementarity of an oligonucleotide probe in the region of the 3' end and the 5' end determines binding to the support.

In particular examples, the oligonucleotide probes on the array include one or more labels, that permit detection of oligonucleotide probe:target sequence hybridization complexes.

F. Output of MiR Gene Expression Analysis Results

Gene expression can be evaluated using any technique described above, or any other method known in the art. As described herein, gene expression can be measured, for example, using labeled probes that can be detected using standard equipment. For example, gene expression measurements using microarray or RT-PCR (which typically use labeled probes specific for a gene product) can be quantitated using a microarray scanner or other suitable scanner for detecting the label. In some embodiments, the device used to measure gene expression is a microarray scanner. Microarray scanners are well known and are commercially available, such as the Model G250 GB Microarray Scanner from Agilent Technologies.

The results of gene expression analysis can be transmitted using any one of a number of output devices or formats known in the art. For example, the output device can be a visual output device, such as a computer screen or a printed piece of paper. In other examples, the output device can be an auditory output device, such as a speaker. In other examples, the output device is a printer. In some cases, the data is recorded in a patient's electronic medical record.

VI. Modulating MicroRNA Expression for Treatment of Sjögren's Syndrome

It is disclosed herein that many microRNAs are differentially expressed in patients with Sjögren's syndrome. As such, an increase in the level of one or more microRNAs down-regulated in Sjögren's syndrome patients, or a decrease in the level of one or more microRNAs up-regulated in Sjögren's syndrome patients may be beneficial for inhibiting the development or progression of Sjögren's syndrome and/or for alleviating one or more signs or symptoms of Sjögren's syndrome (for example, decreased salivary flow).

Without wishing to be bound by theory, it is believed that alterations in the level of one or more miR gene products in cells can result in the deregulation of one or more intended targets for these miRs, which can lead to the development or progression of Sjögren's syndrome. Therefore, altering the level of the miR gene product (e.g., by decreasing the level of a miR that is up-regulated in Sjögren's syndrome or by increasing the level of a miR that is down-regulated in Sjögren's syndrome) may successfully treat or ameliorate one or more signs or symptoms of Sjögren's syndrome.

A. Use of Agents that Inhibit Up-Regulated MicroRNAs

Provided herein is a method of treating a patient with Sjögren's syndrome by administering to the patient a therapeutically effective amount of an agent that inhibits expression of a miR gene product that is up-regulated in Sjögren's syndrome patients compared with a control (such as a healthy control subject), or up-regulated in Sjögren's syndrome patients with low salivary flow relative to a control (such as a Sjögren's syndrome patient with normal salivary flow).

As used herein, "inhibiting expression of miR gene product" means that the production of the precursor and/or active, mature form of the miR gene product after treatment is less than the amount produced prior to treatment. One skilled in the art can readily determine whether miR expression has been inhibited in a subject, using the techniques known in the art and described herein. Inhibition can occur at the level of gene expression (i.e., by inhibiting transcription of a miR gene encoding the miR gene product) or at the level of processing (e.g., by inhibiting processing of a miR precursor into a mature miR).

As used herein, a therapeutically effective amount of a compound that inhibits miR expression is an amount sufficient to result in a biological effect (such as alleviating one or more signs or symptoms of Sjögren's syndrome). For example, an agent can decrease the expression level of a target miR by a desired amount, for example by at least 2-fold, at least 3-fold, at least 4-fold, at least 5-fold, at least 6-fold, at least 8-fold, at least 10-fold, at least 15-fold, at least 20-fold, at least 30-fold or at least 40-fold relative to a control or reference value. In some examples, the diagnostically significant amount is the fold-change in miR gene expression shown in Tables 1-6.

One skilled in the art can readily determine a therapeutically effective amount of an agent to be administered to a given subject by taking into account several factors, such as the size and weight of the subject; the extent of disease progression; the age, health and sex of the subject; the route of administration; and whether the administration is regional or systemic. One skilled in the art can also readily determine an appropriate dosage regimen for administering to a subject an agent that inhibits expression of miR gene product.

In some embodiments, a single agent that inhibits expression of a miR gene product is administered to the subject in need of treatment. In other embodiments, two or more agents (such as 2, 3, 4, 5, 6, 7, 8, 9 or 10 or more) that inhibit expression of a miR gene product are administered to the subject. When two or more agents are administered to the subject, the agents can be administered simultaneously (or within quick succession, such as within minutes of each other), or they can be administered at different times. For example, two or more agents can be administered one hour, twelve hours, one day, two days, five days, one week, two weeks or one month apart.

In some embodiments, an agent that inhibits miR expression can be administered to a subject in combination with one or more additional treatments for Sjögren's syndrome. Exemplary Sjögren's syndrome treatments include, but are not limited to, administration of agents that promote salivary production (such as pilocarpine or cevimeline), moisture replacement therapies (such as eye drops), or administration of NSAIDS or corticosteroids, or other immunosuppressive or immunomodulatory drugs.

An agent that inhibits expression of a miR gene product can be any type of compound, such as, but not limited to, a nucleic acid molecule, polypeptide, antibody or small molecule, that is capable of inhibiting expression of one or more miR gene products. In some embodiments, the agent is an antisense compound.

Any type of antisense compound that specifically targets a miR gene product is contemplated for use to inhibit expression of the target miR gene product. In some examples, the agent is an antisense compound selected from an antisense oligonucleotide, a siRNA, or a ribozyme. Methods of designing, preparing and using antisense compounds are within the abilities of one of skill in the art. Furthermore, sequences for the disclosed miR gene products are publicly available. Antisense compounds specifically targeting a miR that is differentially expressed in Sjögren's syndrome (or other target nucleic acid) can be prepared by designing compounds that are complementary to the target nucleotide sequence, such as a pri-microRNA, pre-microRNA or mature microRNA sequence. Antisense compounds need not be 100% complementary to the target nucleic acid molecule to specifically hybridize with the target nucleic acid molecule. For example, the antisense compound, or antisense strand of the compound If a double-stranded compound, can be at least 75%, at least 80%, at least 85%, at least 90%, at least 95%, at least 99% or 100% complementary to the selected target nucleic acid sequence. Methods of screening antisense compounds for specificity are well known in the art (see, for example, U.S. Patent Application Publication No. 2003-0228689).

Generally, the principle behind antisense technology is that an antisense compound hybridizes to a target nucleic acid and effects the modulation of gene expression activity or function. The modulation of gene expression can be achieved by, for example, target RNA degradation or occupancy-based inhibition. An example of modulation of target RNA function by degradation is RNase H-based degradation of the target RNA upon hybridization with a DNA-like antisense compound, such as an antisense oligonucleotide.

Another example of modulation of gene expression by target degradation is RNA interference (RNAi) using small interfering RNAs (siRNAs). RNAi is a form of antisense-mediated gene silencing involving the introduction of double stranded (ds)RNA-like oligonucleotides leading to the sequence-specific reduction of targeted endogenous mRNA levels. Other compounds that are often classified as antisense compounds are ribozymes. Ribozymes are catalytic RNA molecules that can bind to specific sites on other RNA molecules and catalyze the hydrolysis of phosphodiester bonds in the RNA molecules. Ribozymes modulate gene expression by direct cleavage of a target nucleic acid, such as a miR gene product.

Each of the above-described antisense compounds provides sequence-specific target gene regulation. This sequence-specificity makes antisense compounds effective tools for the selective modulation of a target nucleic acid of interest, such as a miR gene product.

In some embodiments, the antisense compounds are antisense oligonucleotides. The miR gene product-specific antisense oligonucleotides can be any suitable length to allow for hybridization and modulation of gene expression. The length of an antisense oligonucleotide can vary, but is typically about 15 to about 40 nucleotides, including 15, 16, 17, 18, 19, 20, 21, 22, 23, 24, 25, 26, 27, 28, 29, 30, 31, 32, 33, 34, 35, 36, 37, 38, 39 or 40 nucleotides. In some embodiments, the antisense oligonucleotides are about 20 to about 35 nucleotides in length. The antisense oligonucleotides can be DNA, RNA or analogs thereof. Furthermore, the oligonucleotides provided herein can be unmodified or can comprise one or more modifications, such as modified internucleoside linkages, modified sugar moieties, modified bases, or a combination thereof. Oligonucleotide modifications are described in detail below.

In other embodiments, the antisense compounds are siRNA molecules. siRNAs useful for the disclosed methods include short double-stranded RNA from about 17 nucleotides to about 29 nucleotides in length, preferably from about 19 to about 25 nucleotides in length, such as about 21 to about 23 nucleotides in length. The siRNAs are made up of a sense RNA strand and a complementary antisense RNA strand annealed together by standard Watson-Crick base-pairing interactions. The sense strand includes a nucleic acid sequence that is substantially identical to a nucleic acid sequence contained within the target miR gene product. As used herein, an siRNA nucleic acid sequence that is "substantially identical" to a target sequence is a nucleic acid sequence that is identical to the target sequence, or that differs from the target sequence by one, two or three nucleotides. The sense and antisense strands of the siRNA can either include two complementary, single-stranded RNA molecules, or can be a single molecule having two complementary portions (which are base-paired) separated a single-stranded "hairpin" region.

The siRNA can also be altered RNA that differs from naturally-occurring RNA by the addition, deletion, substitution and/or alteration of one or more nucleotides. Such alterations can include addition of non-nucleotide material, such as to one or both of the ends of the siRNA or to one or more internal nucleotides of the siRNA; modifications that make the siRNA resistant to nuclease digestion; or the substitution of one or more nucleotides in the siRNA with deoxyribonucleotides. One or both strands of the siRNA can also include a 3' overhang. As used herein, a "3' overhang" refers to at least one unpaired nucleotide extending from the 3'-end of a duplexed RNA strand. Thus, in certain embodiments, the siRNA includes at least one 3' overhang of from 1 to about 6 nucleotides (which includes ribonucleotides or deoxyribonucleotides) in length, from 1 to about 5 nucleotides in length, from 1 to about 4 nucleotides in length, or from about 2 to about 4 nucleotides in length. In a particular embodiment, the 3' overhang is present on both strands of the siRNA and is 2 nucleotides in length. For example, each strand of the siRNA can comprise 3' overhangs of dithymidylic acid ("TT") or diuridylic acid ("uu").

In other embodiments, the antisense compound is a ribozyme. Ribozymes are nucleic acid molecules having a substrate binding region that is complementary to a contiguous nucleic acid sequence of a miR gene product, and which is able to specifically cleave the miR gene product. The substrate binding region need not be 100% complementary to the target miR gene product. For example, the substrate binding region can be, for example, at least about 50%, at least about 75%, at least about 85%, or at least about 95% complementary to a contiguous nucleic acid sequence in a miR gene product. The enzymatic nucleic acids can also include modifications at the base, sugar, and/or phosphate groups.

Antisense compounds, such as antisense oligonucleotides, siRNAs and ribozymes, can be produced chemically or biologically, or can be expressed from a recombinant plasmid or viral vector, as described in further detail below in regard to expression of isolated miR gene products. Exemplary methods for producing and testing antisense compounds are well known in the art (see, for example, U.S. Pat. Nos. 5,849,902 and 4,987,071; U.S. Patent Application Publication Nos. 2002/0173478 and 2004/0018176; Stein and Cheng, Science 261:1004, 1993; Werner and Uhlenbeck, Nucl. Acids Res. 23:2092-2096, 1995; Hammann et al., Antisense and Nucleic Acid Drug Dev. 9:25-31).

In some examples, the antisense compounds specific for a miR gene product contain one or more modifications to enhance nuclease resistance and/or increase activity of the compound. Modified antisense compounds include those comprising modified backbones or non-natural internucleoside linkages. As defined herein, oligonucleotides having modified backbones include those that retain a phosphorus atom in the backbone and those that do not have a phosphorus atom in the backbone.

Examples of modified oligonucleotide backbones include, but are not limited to, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkyl-phosphonates, thionoalkylphosphotriesters, and boranophosphates having normal 3'-5' linkages, 2'-5' linked analogs of these, and those having inverted polarity wherein the adjacent pairs of the nucleoside units are linked 3'-5' to 5'-3' or 2'-5' to 5'-2'. Representative U.S. patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Examples of modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative U.S. patents that teach the preparation of the above oligonucleosides include, but are not limited to, U.S. Pat. Nos. 5,034,506; 5,166,315; 5,185,444; 5,214,134; 5,216, 141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

In some embodiments, both the sugar and the internucleoside linkage of the nucleotide units of the oligonucleotide or antisense compound are replaced with novel groups. One such modified compound is an oligonucleotide mimetic referred to as a peptide nucleic acid (PNA). In PNA compounds, the sugar-backbone of an oligonucleotide is replaced with an amide containing backbone, in particular an aminoethylglycine backbone. The bases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262. Further teaching of PNA compounds can be found in Nielsen et al. (*Science* 254, 1497-1500, 1991).

Modified oligonucleotides can also contain one or more substituted sugar moieties. In some examples, the oligonucleotides can comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. In other embodiments, the antisense compounds comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, N3, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. In one example, the modification includes 2'-methoxyethoxy (also known as 2'-O-(2-methoxyethyl) or 2'-MOE) (Martin et al., *Helv. Chim. Acta.,* 78, 486-504, 1995). In other examples, the modification includes 2'-dimethylaminooxyethoxy (also known as 2'-DMAOE) or 2'-dimethylaminoethoxyethoxy (also known in the art as 2'-O-dimethylaminoethoxyethyl or 2'-DMAEOE).

Similar modifications can also be made at other positions of the compound. Antisense compounds can also have sugar mimetics such as cyclobutyl moieties in place of the pentofuranosyl sugar. Representative United States patents that teach the preparation of modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920.

Oligonucleotides can also include base modifications or substitutions. As used herein, "unmodified" or "natural" bases include the purine bases adenine (A) and guanine (G), and the pyrimidine bases thymine (T), cytosine (C) and uracil (U). Modified bases include other synthetic and natural bases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further modified bases have been described (see, for example, U.S. Pat. No. 3,687,808; and Sanghvi, Y. S., Chapter 15, Antisense Research and Applications, pages 289-302, Crooke, S. T. and Lebleu, B., ed., CRC Press, 1993).

Certain of these modified bases are useful for increasing the binding affinity of antisense compounds. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. Representative U.S. patents that teach the preparation of modified bases include, but are not limited to, U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; and 5,750,692.

B. Use of Nucleic Acid Molecules Encoding Down-Regulated MicroRNAs

Also provided is a method of treating a patient with Sjögren's syndrome by administering to the patient a therapeutically effective amount of an isolated microRNA gene product that is down-regulated in a patient with Sjögren's syndrome relative to a control (such as a healthy subject), or is down-regulated in a Sjögren's syndrome patient with low salivary flow compared with a control (such as a Sjögren's syndrome patient with normal salivary flow). Further provided is a method of restoring salivary flow in a patient with Sjögren's syndrome by administering a therapeutically effective amount of an isolated miR gene product that is down-regulated in Sjögren's syndrome patients with low salivary flow, relative to a control (such as a Sjögren's syndrome patient with normal salivary flow). As described herein, the miR gene product can be a pri-miRNA, a pre-miRNA or a mature miRNA.

The disclosed methods comprise administering an effective amount of at least one isolated miR gene product, or an isolated variant or biologically-active fragment thereof. The isolated miR gene product that is administered to the subject can be identical to an endogenous wild-type miR gene product (such as a pri-miRNA, pre-miRNA or mature miRNA) that is down-regulated in the patient with Sjögren's syndrome, or it can be a variant or biologically-active fragment thereof. As defined herein, a "variant" of a miR gene product refers to a miRNA that has less than 100% identity to a corresponding wild-type miR gene product and possesses one or more biological activities of the corresponding wild-type miR gene product. Examples of such biological activities include, but are not limited to, inhibition of expression of a target RNA molecule (e.g., inhibiting translation of a target RNA molecule, modulating the stability of a target RNA molecule, or inhibiting processing of a target RNA molecule) and inhibition of a cellular process associated with Sjögren's syndrome (e.g., saliva production). These variants include species variants and variants that are the consequence of one or more mutations (e.g., a substitution, a deletion, an insertion) in a miR gene. In certain embodiments, the variant is at least about 70%, at least about 75%, at least about 80%, at least about 85%, at least about 90%, at least about 95%, at least about 98%, or at about 99% identical to a corresponding wild-type miR gene product.

As used herein, a "biologically-active fragment" of a miR gene product refers to an RNA fragment of a miR gene product that possesses one or more biological activities of a corresponding wild-type miR gene product. As described above, examples of such biological activities include, but are not limited to, inhibition of expression of a target RNA molecule and inhibition of a cellular process associated with Sjögren's syndrome. In certain embodiments, the biologically-active fragment is at least about 9, at least about 11, at least about 13, at least about 15, at least about 17 or at least about 19 nucleotides in length.

A therapeutically effective amount of an isolated gene product can be, for example, the amount necessary to alleviate one or more signs or symptoms of Sjögren's syndrome, and/or the amount required to delay progression of the disease. One of skill in the art can determine the amount of an isolated miR gene product required for therapeutic efficacy.

In some embodiments, a single isolated miR gene product is administered to the subject in need of treatment. In other embodiments, two or more miR gene products (such as 2, 3, 4, 5, 6, 7, 8, 9 or 10 or more) are administered to the subject. When two or more miR gene products are administered to the subject, the miR gene products can be administered simultaneously (or within quick succession, such as within minutes of each other), or they can be administered at different times. For example, two or more miR gene products can be administered one hour, twelve hours, one day, two days, five days, one week, two weeks or one month apart.

In some embodiments, an isolated miR gene product can be administered to a subject in combination with one or more additional treatments for Sjögren's syndrome. Exemplary Sjögren's syndrome treatments include, but are not limited to, administration of agents that promote salivary production (such as pilocarpine or cevimeline), moisture replacement therapies (such as eye drops), or administration of NSAIDs or corticosteroids.

As used herein, an "isolated" miR gene product is one that is synthesized, or is purified away from other biological components of the cell or tissue in which the miR naturally occurs. For example, a synthetic miR gene product, or a miR gene product partially or completely separated from the other biological components of its natural state is considered to be "isolated." Isolated miR gene products can be obtained using a number of standard techniques. For example, the miR gene products can be chemically synthesized or recombinantly produced using methods known in the art. In one embodiment, miR gene products are chemically synthesized using appropriately protected ribonucleoside phosphoramidites and a conventional DNA/RNA synthesizer. Commercial suppliers of synthetic RNA molecules or synthesis reagents include, for example, Proligo (Hamburg, Germany), Dharmacon Research (Lafayette, Colo.), Pierce Chemical (Rockford, Ill.), Glen Research (Sterling, VS), ChemGenes (Ashland, Mass.) and Cruachem (Glasgow, United Kingdom).

In some embodiments, the method includes administering a vector encoding a miR gene product. Vectors can be of non-viral (for example, plasmids) or viral (for example, adenovirus, adeno-associated virus, retrovirus, herpes virus, vaccinia virus) origin. Suitable vectors, such as gene therapy vectors, are well known in the art.

In some examples, the miR gene products are expressed from recombinant circular or linear DNA plasmids using any suitable promoter. Suitable promoters for expressing RNA from a plasmid include, for example, the U6 or H1 RNA pol III promoter sequences, or a cytomegalovirus promoter. Selection of other suitable promoters is within the skill in the art. The recombinant plasmids of the invention can also comprise inducible or regulatable promoters for expression of the miR gene products.

When two or more miR gene products are to be expressed, the miR gene products can each be expressed from separate recombinant plasmids, or they can be expressed from the same recombinant plasmid. In one embodiment, the miR gene products are expressed as RNA precursor molecules from a single plasmid, and the precursor molecules are processed into the functional miR gene product within the target cell. Selection of plasmids suitable for expressing the miR gene products, methods for inserting nucleic acid sequences into the plasmid to express the gene products, and methods of delivering the recombinant plasmid to the cells of interest are within the skill in the art (see, for example, Zeng et al., *Mol. Cell.* 9:1327-1333, 2002; Tuschl, *Nat. Biotechnol.*, 20:446-448, 2002; Brummelkarnp et al., Science 296:550-553, 2002; Miyagishi et al., *Nat. Biotechnol.* 20:497-500, 2002; Paddison et al., *Genes Dev.* 16:948-958, 2002; Lee et al., *Nat. Biotechnol.* 20:500-505, 2002; and Paul et al., *Nat. Biotechnol.* 20:505-508, 2002). In one embodiment, a plasmid expressing the miR gene product comprises a sequence encoding a miR precursor RNA operably linked to the CMV intermediate-early promoter.

The miR gene products can also be expressed from recombinant viral vectors. When administering two or more miR gene products, it is contemplated that the miR gene products can be expressed from two separate recombinant viral vectors, or from the same viral vector. The RNA expressed from the recombinant viral vectors can either be isolated from cultured cell expression systems by standard techniques, or can be expressed directly in target cells or tissues of a patient with Sjögren's syndrome.

The recombinant viral vectors of use with the disclosed methods include sequences encoding the miR gene products and any suitable promoter for expressing the RNA sequences. Suitable promoters include, but are not limited to, the U6 or H1 RNA pol III promoter sequences, or a cytomegalovirus promoter. Selection of other suitable promoters is within the skill in the art. The recombinant viral vectors of the invention can also comprise inducible or regulatable promoters for expression of the miR gene products.

Suitable viral vectors include, but are not limited to, adenovirus vectors, adeno-associated virus vectors, retroviral vectors, lentiviral vectors, herpesviral vectors, and the like. For example, adenovirus vectors can be first, second, third and/or fourth generation adenoviral vectors or gutless adenoviral vectors. Adenovirus vectors can be generated to very high titers of infectious particles; infect a great variety of cells; efficiently transfer genes to cells that are not dividing; and are seldom integrated in the host genome, which avoids the risk of cellular transformation by insertional mutagenesis (Douglas and Curiel, *Science and Medicine, March/April* 1997, pages 44-53; Zern and Kresinam, *Hepatology* 25(2), 484-491, 1997). Representative adenoviral vectors which can be used for the methods provided herein are described by Stratford-Perricaudet et al. (*J. Clin. Invest.* 90: 626-630, 1992); Graham and Prevec (In Methods in Molecular Biology: Gene Transfer and Expression Protocols 7: 109-128, 1991); and Barr et al. (*Gene Therapy*, 2:151-155, 1995).

Adeno-associated virus (AAV) vectors also are suitable for administration of HCC-associated genes. Methods of generating AAV vectors, administration of AAV vectors and their use are well known in the art (see, for example, U.S. Pat. No. 6,951,753; U.S. Pre-Grant Publication Nos. 2007-036757, 2006-205079, 2005-163756, 2005-002908; and PCT Publication Nos. WO 2005/116224 and WO 2006/119458).

Retrovirus, including lentivirus, vectors can also be used with the methods described herein. Lentiviruses include, but are not limited to, human immunodeficiency virus (such as HIV-1 and HIV-2), feline immunodeficiency virus, equine infectious anemia virus and simian immunodeficiency virus. Other retroviruses include, but are not limited to, human T-lymphotropic virus, simian T-lymphotropic virus, murine leukemia virus, bovine leukemia virus and feline leukemia virus. Methods of generating retrovirus and lentivirus vectors and their uses have been well described in the art (see, for example, U.S. Pat. Nos. 7,211,247; 6,979,568; 7,198,784; 6,783,977; and 4,980,289).

Suitable herpesvirus vectors can be derived from any one of a number of different types of herpesviruses, including, but not limited to, herpes simplex virus-1 (HSV-1), HSV-2 and herpesvirus saimiri. Recombinant herpesvirus vectors, their construction and uses are well described in the art (see, for example, U.S. Pat. Nos. 6,951,753; 6,379,6741 6,613,892;

6,692,955; 6,344,445; 6,319,703; and 6,261,552; and U.S. Patent Application Publication No. 2003-0083289).

As used herein, a "therapeutically effective amount" of an isolated miR gene product is an amount sufficient to result in a biological effect (such as alleviating one or more signs or symptoms of Sjögren's syndrome. One skilled in the art can readily determine a therapeutically effective amount of a miR gene product to be administered to a given subject, by taking into account factors, such as the size and weight of the subject; the extent of disease progression; the age, health and sex of the subject; the route of administration; and whether the administration is regional or systemic.

For example, an effective amount of an isolated miR gene product can be based on the approximate body weight of a subject to be treated. Such effective amounts can be administered by any suitable route, such as, for example, parenterally or enterally. In some examples, a therapeutically effective amount of the isolated miR gene product that is administered to a subject can range from about 5 to about 3000 micrograms/kg of body weight, from about 700 to about 1000 micrograms/kg of body weight, or greater than about 1000 micrograms/kg of body weight.

One skilled in the art can also readily determine an appropriate dosage regimen for the administration of an isolated miR gene product to a given subject. For example, a miR gene product can be administered to the subject once (e.g., as a single injection or deposition). Alternatively, a miR gene product can be administered once or twice daily to a subject for a period of from about three to about twenty-eight days, more particularly from about seven to about ten days. In a particular dosage regimen, a miR gene product is administered once a day for seven days. Where a dosage regimen comprises multiple administrations, it is understood that the effective amount of the miR gene product administered to the subject can comprise the total amount of gene product administered over the entire dosage regimen.

C. Administration of Therapeutic Agents

Therapeutic agents can be administered to a subject in need of treatment using any suitable means known in the art. Methods of administration include, but are not limited to, intraductal, intradermal, intramuscular, intraperitoneal, parenteral, intravenous, subcutaneous, vaginal, rectal, intranasal, inhalation, oral or by gene gun. Intranasal administration refers to delivery of the compositions into the nose and nasal passages through one or both of the nares and can comprise delivery by a spraying mechanism or droplet mechanism, or through aerosolization of the nucleic acid or virus. Administration of the compositions by inhalant can be through the nose or mouth via delivery by spraying or droplet mechanisms. Delivery can be directly to any area of the respiratory system via intubation. Parenteral administration is generally achieved by injection. Injectables can be prepared in conventional forms, either as liquid solutions or suspensions, solid forms suitable for solution of suspension in liquid prior to injection, or as emulsions. Injection solutions and suspensions can be prepared from sterile powders, granules, and tablets. Administration can be systemic or local.

Therapeutic agents can be administered in any suitable manner, preferably with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Administration can be accomplished by single or multiple doses. The dose required will vary from subject to subject depending on the species, age, weight and general condition of the subject, the particular therapeutic agent being used and its mode of administration. An appropriate dose can be determined by one of ordinary skill in the art using only routine experimentation.

In some embodiments, the therapeutic agent is a nucleic acid molecule, such as a miR gene product, a vector encoding a miR gene product, an antisense compound or a vector encoding an antisense compound. A nucleic acid-based therapeutic agent can be administered to a subject by any suitable route. In some examples, the agents are administered using an enteral or parenteral administration route. Suitable enteral administration routes include, for example, oral, rectal, or intranasal delivery. Suitable parenteral administration routes include, for example, intravascular administration (such as intravenous bolus injection, intravenous infusion, intra-arterial bolus injection, intra-arterial infusion and catheter instillation into the vasculature); subcutaneous injection or deposition, including subcutaneous infusion (such as by osmotic pumps); direct application to the tissue of interest, for example by a catheter or other placement device (e.g., a suppository or an implant comprising a porous, non-porous, or gelatinous material); and inhalation. Particularly suitable administration routes are injection, infusion and direct injection into a target tissue.

In the context of the present disclosure, a miR gene product or an antisense compound can be administered to the subject either as naked RNA or DNA in combination with a delivery reagent, or can be encoded by a recombinant plasmid or viral vector. Recombinant plasmids and viral vectors including sequences that express the miR gene products or antisense compounds, and techniques for delivering such plasmids and vectors to target cells, are well known in the art.

In some embodiments, liposomes are used to deliver a miR gene product or antisense compound (or nucleic acids comprising sequences encoding them) to a subject. Liposomes can also increase the blood half-life of the gene products or nucleic acids. Suitable liposomes for use in the invention can be formed from standard vesicle-forming lipids, which generally include neutral or negatively charged phospholipids and a sterol, such as cholesterol. The selection of lipids is generally guided by consideration of several factors, such as the desired liposome size and half-life of the liposomes in the blood stream. A variety of methods are known in the art for preparing liposomes (see, for example, Szoka et al., *Ann. Rev. Biophys. Bioeng.* 9:467, 1980; and U.S. Pat. Nos. 4,235,871; 4,501,728; 4,837,028; and 5,019,369). In some embodiments, polymers can be used to deliver a miR gene product or antisense compound to a subject. Cationic lipids and polymers that can be used to deliver therapeutic RNA molecules have been described (see, for example, Zhang et al., *J Control Release*. 123(1):1-10, 2007; Vorhies et al., *Methods Mol. Biol.* 480:11-29, 2009; and U.S. Patent Application Publication No. 2009/0306194). Polypeptide carriers can also be used to administer a miR gene product to a subject (see, for example, Rahbek et al., *J. Gene Med.* 10:81-93, 2008).

The following examples are provided to illustrate certain particular features and/or embodiments. These examples should not be construed to limit the disclosure to the particular features or embodiments described.

EXAMPLES

Example 1

Identification of Differentially Expressed MicroRNAs in Patients with Sjögren's Syndrome Materials and Methods Sample Acquisition and MicroRNA Isolation Minor salivary gland samples were obtained from Caucasian women with primary Sjögren's syndrome and from normal volunteers. All subjects had a complete rheumatologic, oral and ophthalmologic exam and laboratory evaluation at the Clinical Center of the National Institutes of Health. All Sjögren's syndrome patients fulfilled European-American criteria for primary Sjögren's syndrome. The median age of the patients at the time of biopsy for the control group was 43.5 years (ranging from 21-58 years), for the low focus score group was 58 years (ranging from 23-67 years) and for the high focus score group was 51.5 years (ranging from 37-70 years).

Minor salivary glands from the lower lip were excised and extra specimens were snap frozen for microRNA isolation. The tissues were homogenized and microRNA was isolated with the miRNeasy™ mini kit (Qiagen, Valencia, Calif.). The quality of miRNA was assessed with the Agilent Small RNA Kit on the 2100 Agilent Bioanalyzer (Agilent Technologies, Santa Clara, Calif.) and NanoDrop 8000 (NanoDrop Technologies, Wilmington, Del.).

Microarrays

Agilent miRNA Microarrays (V1) (Agilent Technologies) with probes specific for 470 human and 64 human viral miRNAs (8 arrays per slide) were used to profile minor salivary gland miRNA. Only samples with an RNA integrity number greater than 7 on the Agilent RNA 6000 Nano Chip, an optimum miRNA curve on the Agilent Small RNA Chip (determined by the manufacturer's instructions), and 260/280 and 260/230 ratios greater than 2.00 on the NanoDrop 8000 were used for microarray analysis. For each array, 100 ng of total RNA was used. Arrays were run according to the manufacturer's protocol. Microarrays were scanned using the Model G2505B Microarray Scanner (Agilent Technologies) and data was extracted and array quality control was performed using the Agilent Feature Extraction Software.

Four categories of patients were compared with each other (n=16) and with normal volunteers (n=8). Half the patients had low grade inflammation in the minor salivary gland (low focus score of 1 or 2) and half had extensive inflammation in minor salivary gland (high focus score of 12). In each group of patients, half had preserved salivary flow ($\geq$1.5 mL/15 minutes; "high flow") and half had low salivary flow (<1.5 mL/15 minutes; "low flow") (FIG. 1).

Analysis

Normalization.

MicroRNA array data were normalized using a set of (putative) housekeeper microRNAs that were identified in the minor salivary gland arrays as follows. A housekeeper microRNA is by definition expressed at constant levels in all tissue samples. Accordingly, the ratio of the intensities of two housekeepers should be the same across all arrays in the data set independent of normalization. To search for possible housekeeper microRNAs that behaved in this way, only 'candidate' microRNAs that were scored as present by the Agilent Feature Extraction Software on all the arrays (i.e. for which gIsGeneDetected=1 on all arrays; there were a total of 132 such microRNAs) were considered. The array data were normalized in turn to the intensities of each of these candidate microRNAs. In each case we calculated the mean and coefficient of variation (CV) for all other candidate microRNAs across the normalized arrays and counted the number for which CV<0.22 i.e., the number of other candidate microRNAs whose expression appeared to vary in synchrony with the microRNA used to normalize the arrays.

Candidate microRNAs for which these scores were 7 or greater were then used as a set of preliminary housekeepers. Next, each array was normalized to the geometric mean of the intensities of the preliminary housekeepers on that array. The mean and CV for all candidate microRNAs on these normalized arrays were then calculated and those with CV<0.22 were used as the next set of preliminary housekeepers. This process was repeated until the set of housekeepers yielded by the calculation was the same as that used to derive it (i.e., until a self-consistent result was obtained). The arrays were then normalized to 0.001 times the geometric means of these final housekeeper microRNAs (the geometric mean was typically about 1000 so this yielded a normalization factor about 1). In this final normalized dataset, the intensities of microRNAs that were scored as absent by the Agilent Feature Extraction Software (i.e., for which gIsGeneDetected=0) were set equal to 1.0.

Data Analysis and Software.

All of the microarray analyses reported herein were performed using BRB-ArrayTools (version 3.7.0) developed by Dr. Richard Simon and the BRB-ArrayTools Development Team, with the exception of the principle component analysis (PCA), which was carried out using the program GENESPRING™ version 10.0 (Agilent). The above normalized microRNA array data were loaded into BRB ArrayTools where they were thresholded to 1.0, log 2-transformed, and filtered to remove microRNAs with low variability (specifically those microRNAs whose variance across all arrays was not significantly greater (p>0.01) than that of the median of all such variances).

Of the 534 microRNAs on the arrays 239 passed the filtering criteria. The resultant filtered dataset was used for all subsequent analyses. For microRNA target prediction, the RNA22 algorithm was used (*homo sapiens* 3' UTR precompiled predictions) (Miranda et al., *Cell* 126:1203-1217, 2006). Data were also analyzed through the use of Ingenuity Pathways Analysis (Ingenuity Systems™). A dataset containing mRNA identifiers was uploaded into the application. Only mRNAs targeted by at least 20% of the microRNAs on each of the groups of interest were used for downstream analysis.

Each identifier was mapped to its corresponding gene object in the Ingenuity knowledge base. These genes, called 'focus genes' by the software, were overlaid onto a global molecular network developed from information contained in the Ingenuity knowledge base. Networks of these focus genes were then algorithmically generated based on their connectivity. The Functional Analysis of a network identified the biological functions and/or diseases that were most significant to the genes in the network. The network genes associated with biological functions and/or diseases in the Ingenuity knowledge base were considered for the analysis. Fischer's exact test was used to calculate a p-value determining the probability that each biological function and/or disease assigned to that network is due to chance alone. Canonical Pathways Analysis identified the pathways from the Ingenuity Pathways Analysis library of canonical pathways that were most significant to the dataset. The significance of the association between the dataset and the canonical pathway was measured in 2 ways: (1) A ratio of the number of genes from the dataset that met the expression value cutoff that map to the pathway divided by the total number of molecules that exist in the canonical pathway is displayed; and (2) Fischer's exact test was used to calculate a p-value determining the probability that the association between the genes in the dataset and the canonical pathway is explained by chance alone.

Real Time Quantitative PCR

Real Time Quantitative PCR analysis was performed on 15 minor salivary gland samples with various inflammatory scores using the TaqMan™ microRNA Assay (Applied Biosystems); these samples were independent of those used in the microRNA microarray analyses described herein. Reverse transcription was performed according to the manufacturer's instructions using 10 ng starting material (determined based on optimized test assays to ensure detection was within sensitivity limits). Specific microRNA primers were used for the detection of microRNAs hsa-mir-768-3p and hsa-mir-574-3p, both acquired from Applied Biosystems (part numbers 4395188 and 4395460, respectively). Briefly, for the reverse transcription, a 15 µL RT reaction was run on a Veriti 96-well thermal cycler (Applied Biosystems, Foster City, Calif.) for 30 minutes at 16° C., 30 minutes at 42° C., and 5 minutes at 85° C. Real Time PCR was run on an ABI Prism 7500 (Applied Biosystems). Each PCR reaction was run in triplicate. The 20 µL PCR reaction was run with cycling conditions of 10 minutes at 95° C., followed by 40 cycles of denaturing for 15 seconds at 95° C. and annealing and extending for 60 seconds at 60° C.

There were three replicates for each of the PCR samples. For each sample, there was a control endogenous small nucleolar RNA, RNU48. The level of each sample was compared to the level of this control using the $2^{-\Delta\Delta C}T$ Method (Livak et al., *Methods (Duluth)* 25:402-408, 2001).

Example 2

Analysis of MicroRNA Microarray Data

Analysis Methods

Statistical analysis was performed using the Agilent GENESPRING™ program Versions 9 and 10, and the BRB Array tools package version 3.7.0 Stable Release. For analysis with GENESPRING™, data was imported and normalized according to the array manufacturer's instructions.

Differentially expressed miRNAs were detected between categories of patients and normal volunteers using an unpaired T-Test and the Benjamini-Hochberg correction. Differentially expressed miRNAs were considered those with a statistical significance (p<0.05) with correction in the unpaired T-Test and a fold change greater than 2. Data was collected comparing the following five categories:
1) All Sjögren's syndrome samples versus normal volunteers (Table 1 and Table 2)
2) Low focus score Sjögren's syndrome samples compared with normal volunteers (Table 3)
3) Normal salivary flow versus low salivary flow among high focus score samples (Table 4)
4) Normal salivary flow versus low salivary flow among low focus score samples (Table 5)
5) High focus score versus low focus score samples (Table 6)

Results

Table 1 provides a list of microRNAs that are differentially expressed in the minor salivary glands of Sjögren's syndrome patients, compared to minor salivary glands of normal healthy volunteers. Shown are microRNAs exhibiting a two-fold or greater increase or decrease in expression (statistical significance set at p=0.01). Also listed is the fold-change in microRNA expression (middle column) and whether the microRNA is up-regulated ("up") or down-regulated ("down") in normal salivary glands compared with salivary glands from Sjögren's syndrome patients (right column). In this table, the minor salivary glands from Sjögren's syndrome patients are grouped together independent of their focus score (a measure of inflammation) or their salivary flow. All normal volunteer minor salivary glands had a focus score of 0.

TABLE 1

Differentially expressed microRNAs in minor salivary glands of Sjögren's syndrome patients relative to healthy control subjects (p = 0.01)

| microRNA | Fold change (Normal vs. Sjögrens) | Regulation (Normal vs. Sjögrens) |
| --- | --- | --- |
| ebv-miR-BART13 | 7.00 | down |
| ebv-miR-BART19 | 45.73 | down |
| hsa-let-7d | 2.05 | up |
| hsa-let-7e | 2.37 | up |
| hsa-miR-125a | 2.29 | up |
| hsa-miR-126* | 4.22 | down |
| hsa-miR-139 | 2.97 | up |
| hsa-miR-140 | 2.45 | up |
| hsa-miR-143 | 2.38 | up |
| hsa-miR-145 | 2.56 | up |
| hsa-miR-148a | 2.67 | up |
| hsa-miR-148b | 2.10 | up |
| hsa-miR-149 | 3.05 | up |
| hsa-miR-150 | 32.05 | down |
| hsa-miR-152 | 2.19 | up |
| hsa-miR-17-3p | 2.42 | up |
| hsa-miR-183 | 7.15 | up |
| hsa-miR-188 | 2.59 | down |

TABLE 1-continued

Differentially expressed microRNAs in minor salivary glands of Sjögren's syndrome patients relative to healthy control subjects (p = 0.01)

| microRNA | Fold change (Normal vs. Sjögrens) | Regulation (Normal vs. Sjögrens) |
|---|---|---|
| hsa-miR-189 | 4.75 | up |
| hsa-miR-191* | 2.37 | up |
| hsa-miR-197 | 2.6 | up |
| hsa-miR-198 | 3.07 | down |
| hsa-miR-200a | 2.92 | up |
| hsa-miR-200a* | 3.29 | up |
| hsa-miR-200b | 2.98 | up |
| hsa-miR-200c | 3.88 | up |
| hsa-miR-202 | 2.67 | down |
| hsa-miR-205 | 2.11 | down |
| hsa-miR-212 | 4.35 | down |
| hsa-miR-22 | 3.74 | up |
| hsa-miR-23b | 2.00 | up |
| hsa-miR-28 | 2.96 | up |
| hsa-miR-299-5p | 2.58 | up |
| hsa-miR-30a-3p | 2.16 | up |
| hsa-miR-30b | 3.37 | down |
| hsa-miR-30e-3p | 2.23 | up |
| hsa-miR-32 | 2.19 | up |
| hsa-miR-324-5p | 2.04 | up |
| hsa-miR-326 | 2.84 | up |
| hsa-miR-328 | 4.52 | up |
| hsa-miR-335 | 2.27 | up |
| hsa-miR-339 | 2.76 | up |
| hsa-miR-340 | 3.05 | up |
| hsa-miR-342 | 3.49 | down |
| hsa-miR-363 | 3.23 | up |
| hsa-miR-370 | 3.31 | down |
| hsa-miR-375 | 3.25 | up |
| hsa-miR-378 | 2.12 | up |
| hsa-miR-379 | 2.96 | up |
| hsa-miR-410 | 2.57 | up |
| hsa-miR-423 | 2.52 | up |
| hsa-miR-424 | 3.47 | up |
| hsa-miR-429 | 2.15 | up |
| hsa-miR-432 | 2.49 | up |
| hsa-miR-455 | 2.26 | down |
| hsa-miR-493-5p | 2.44 | up |
| hsa-miR-494 | 6.58 | down |
| hsa-miR-509 | 2.38 | down |
| hsa-miR-512-3p | 2.63 | down |
| hsa-miR-513 | 6.47 | down |
| hsa-miR-542-3p | 2.33 | up |
| hsa-miR-548c | 7.13 | up |
| hsa-miR-557 | 2.15 | up |
| hsa-miR-560 | 2.49 | down |
| hsa-miR-564 | 6.23 | down |
| hsa-miR-565 | 6.10 | down |
| hsa-miR-574 | 4.28 | up |
| hsa-miR-575 | 4.53 | down |
| hsa-miR-582 | 2.38 | up |
| hsa-miR-585 | 10.59 | up |
| hsa-miR-590 | 2.17 | up |
| hsa-miR-622 | 3.15 | down |
| hsa-miR-625 | 2.10 | up |
| hsa-miR-768-3p | 3.93 | down |
| hsa-miR-768-5p | 8.32 | up |
| hsa-miR-801 | 7.31 | down |
| hsa-miR-9* | 3.58 | up |
| hsa-miR-92 | 2.32 | up |
| hsa-miR-96 | 2.13 | up |
| hsa-miR-99b | 2.23 | down |
| kshv-miR-K12-3 | 3.01 | down |

Similarly, Table 2 provides a list of microRNAs that are differentially expressed in the minor salivary glands of Sjögren's syndrome patients, compared to minor salivary glands of normal healthy volunteers, but with a statistical significance set at p=0.05.

TABLE 2

Differentially expressed microRNAs in minor salivary glands of Sjögren's syndrome patients relative to healthy control subjects (p = 0.05)

| microRNA | Fold change (Normal vs. Sjögrens) | Regulation (Normal vs. Sjögrens) |
|---|---|---|
| ebv-miR-BART13 | 7.00 | down |
| ebv-miR-BART19 | 45.73 | down |
| hsa-let-7d | 2.05 | up |
| hsa-let-7e | 2.37 | up |
| hsa-miR-125a | 2.29 | up |
| hsa-miR-126* | 4.22 | down |
| hsa-miR-139 | 2.97 | up |
| hsa-miR-140 | 2.45 | up |
| hsa-miR-142-5p | 3.04 | down |
| hsa-miR-143 | 2.38 | up |
| hsa-miR-145 | 2.56 | up |
| hsa-miR-148a | 2.67 | up |
| hsa-miR-148b | 2.10 | up |
| hsa-miR-149 | 3.05 | up |
| hsa-miR-150 | 32.05 | down |
| hsa-miR-152 | 2.19 | up |
| hsa-miR-17-3p | 2.42 | up |
| hsa-miR-183 | 7.15 | up |
| hsa-miR-187 | 2.14 | up |
| hsa-miR-188 | 2.59 | down |
| hsa-miR-189 | 4.75 | up |
| hsa-miR-191* | 2.37 | up |
| hsa-miR-197 | 2.56 | up |
| hsa-miR-198 | 3.07 | down |
| hsa-miR-200a | 2.92 | up |
| hsa-miR-200a* | 3.29 | up |
| hsa-miR-200b | 2.98 | up |
| hsa-miR-200c | 3.88 | up |
| hsa-miR-202 | 2.67 | down |
| hsa-miR-205 | 2.11 | down |
| hsa-miR-212 | 4.35 | down |
| hsa-miR-22 | 3.74 | up |
| hsa-miR-23b | 2.00 | up |
| hsa-miR-28 | 2.96 | up |
| hsa-miR-299-5p | 2.58 | up |
| hsa-miR-30a-3p | 2.16 | up |
| hsa-miR-30b | 3.37 | down |
| hsa-miR-30e-3p | 2.23 | up |
| hsa-miR-32 | 2.19 | up |
| hsa-miR-324-5p | 2.04 | up |
| hsa-miR-326 | 2.84 | up |
| hsa-miR-328 | 4.52 | up |
| hsa-miR-335 | 2.27 | up |
| hsa-miR-338 | 2.94 | up |
| hsa-miR-339 | 2.76 | up |
| hsa-miR-340 | 3.05 | up |
| hsa-miR-342 | 3.49 | down |
| hsa-miR-363 | 3.23 | up |
| hsa-miR-370 | 3.31 | down |
| hsa-miR-375 | 3.25 | up |
| hsa-miR-378 | 2.12 | up |
| hsa-miR-379 | 2.96 | up |
| hsa-miR-410 | 2.57 | up |
| hsa-miR-423 | 2.52 | up |
| hsa-miR-424 | 3.47 | up |
| hsa-miR-429 | 2.15 | up |
| hsa-miR-432 | 2.49 | up |
| hsa-miR-452 | 2.13 | down |
| hsa-miR-455 | 2.26 | down |
| hsa-miR-493-5p | 2.44 | up |
| hsa-miR-494 | 6.58 | down |
| hsa-miR-509 | 2.38 | down |
| hsa-miR-512-3p | 2.63 | down |
| hsa-miR-513 | 6.47 | down |
| hsa-miR-542-3p | 2.33 | up |
| hsa-miR-548c | 7.13 | up |
| hsa-miR-551b | 2.11 | up |
| hsa-miR-557 | 2.15 | up |
| hsa-miR-560 | 2.49 | down |
| hsa-miR-564 | 6.23 | down |
| hsa-miR-565 | 6.10 | down |
| hsa-miR-574 | 4.28 | up |

TABLE 2-continued

Differentially expressed microRNAs in minor salivary glands of Sjögren's syndrome patients relative to healthy control subjects (p = 0.05)

| microRNA | Fold change (Normal vs. Sjögrens) | Regulation (Normal vs. Sjögrens) |
|---|---|---|
| hsa-miR-575 | 4.53 | down |
| hsa-miR-582 | 2.38 | up |
| hsa-miR-585 | 10.59 | up |
| hsa-miR-590 | 2.17 | up |
| hsa-miR-622 | 3.15 | down |
| hsa-miR-625 | 2.10 | up |
| hsa-miR-662 | 2.61 | down |
| hsa-miR-768-3p | 3.93 | down |
| hsa-miR-768-5p | 8.32 | up |
| hsa-miR-801 | 7.31 | down |
| hsa-miR-9* | 3.58 | up |
| hsa-miR-92 | 2.317 | up |
| hsa-miR-96 | 2.13 | up |
| hsa-miR-99b | 2.23 | down |
| hsv1-miR-H1 | 2.15 | down |
| kshv-miR-K12-3 | 3.01 | down |

Table 3 provides a list of microRNAs that are differentially expressed in the minor salivary glands of Sjögren's syndrome patients with a low focus score (a measure of inflammation), compared to minor salivary glands of normal healthy volunteers minor salivary glands. Shown are microRNAs exhibiting a two-fold or greater increase or decrease in expression (statistical significance set at p=0.01). Also listed is the fold-change in microRNA expression (middle column) and whether the microRNA is up-regulated ("up") or down-regulated ("down") in Sjögren's syndrome patients with a low focus score compared with salivary glands from normal subjects (right column).

TABLE 3

Differentially expressed microRNAs in minor salivary glands of Sjögren's syndrome patients with a low focus score relative to healthy control subjects

| microRNA | Fold change (Low vs. Normal) | Regulation (Low vs. Normal) |
|---|---|---|
| ebv-miR-BART13 | 7.33 | up |
| ebv-miR-BART19 | 28.69 | up |
| hsa-let-7e | 2.37 | down |
| hsa-miR-125a | 2.02 | down |
| hsa-miR-126* | 2.46 | up |
| hsa-miR-139 | 2.63 | down |
| hsa-miR-140 | 2.66 | down |
| hsa-miR-149 | 2.29 | down |
| hsa-miR-150 | 11.53 | up |
| hsa-miR-17-3p | 2.36 | down |
| hsa-miR-183 | 4.91 | down |
| hsa-miR-186 | 2.22 | down |
| hsa-miR-189 | 3.00 | down |
| hsa-miR-197 | 2.96 | down |
| hsa-miR-198 | 2.42 | up |
| hsa-miR-200a* | 2.46 | down |
| hsa-miR-200b | 2.15 | down |
| hsa-miR-200c | 2.87 | down |
| hsa-miR-202 | 2.69 | up |
| hsa-miR-205 | 2.25 | up |
| hsa-miR-21 | 2.14 | down |
| hsa-miR-212 | 4.34 | up |
| hsa-miR-22 | 3.44 | down |
| hsa-miR-28 | 2.63 | down |
| hsa-miR-30b | 3.96 | up |
| hsa-miR-30e-3p | 2.12 | down |
| hsa-miR-326 | 3.85 | down |
| hsa-miR-328 | 4.29 | down |

TABLE 3-continued

Differentially expressed microRNAs in minor salivary glands of Sjögren's syndrome patients with a low focus score relative to healthy control subjects

| microRNA | Fold change (Low vs. Normal) | Regulation (Low vs. Normal) |
|---|---|---|
| hsa-miR-339 | 2.52 | down |
| hsa-miR-340 | 2.92 | down |
| hsa-miR-363 | 2.39 | down |
| hsa-miR-379 | 2.18 | down |
| hsa-miR-423 | 2.56 | down |
| hsa-miR-424 | 2.52 | down |
| hsa-miR-454-3p | 2.11 | down |
| hsa-miR-455 | 2.21 | up |
| hsa-miR-494 | 5.96 | up |
| hsa-miR-513 | 3.62 | up |
| hsa-miR-548c | 7.98 | down |
| hsa-miR-557 | 2.14 | down |
| hsa-miR-564 | 5.28 | up |
| hsa-miR-565 | 6.66 | up |
| hsa-miR-574 | 3.08 | down |
| hsa-miR-575 | 3.27 | up |
| hsa-miR-584 | 2.01 | up |
| hsa-miR-585 | 8.40 | down |
| hsa-miR-622 | 2.99 | up |
| hsa-miR-625 | 2.82 | down |
| hsa-miR-652 | 2.07 | down |
| hsa-miR-768-3p | 3.06 | up |
| hsa-miR-768-5p | 12.05 | down |
| hsa-miR-801 | 4.64 | up |
| hsa-miR-9* | 2.90 | down |
| hsa-miR-92 | 2.55 | down |
| kshv-miR-K12-3 | 2.98 | up |

Table 4 provides a list of microRNAs that are differentially expressed in the minor salivary glands of Sjögren's syndrome patients with a high focus score and low salivary flow, relative to Sjögren's syndrome patients with a high focus score and normal salivary flow. Shown are microRNAs exhibiting a two-fold or greater increase or decrease in expression (statistical significance set at p=0.05). Also listed is the fold-change in microRNA expression (middle column) and whether the microRNA is up-regulated ("up") or down-regulated ("down") in Sjögren's syndrome patients with high focus score/normal salivary flow compared to high focus score/low salivary flow (right column). In this table, all the microRNAs are overexpressed in the high focus score minor salivary glands from normal salivary flow Sjögren's syndrome patients when compared to high focus score minor salivary glands from low salivary flow Sjögren's syndrome patients.

TABLE 4

Differentially expressed microRNAs in minor salivary glands of Sjögren's syndrome patients with a high focus score/normal salivary flow (Normal) relative to Sjögren's syndrome patients with a high focus score/low salivary flow (Low)

| microRNA | Fold change (Normal vs. Low) | Regulation (Normal vs. Low) |
|---|---|---|
| hsa-miR-101 | 2.77 | up |
| hsa-miR-136 | 7.09 | up |
| hsa-miR-141 | 3.62 | up |
| hsa-miR-142-3p | 5.10 | up |
| hsa-miR-144 | 13.69 | up |
| hsa-miR-18a | 2.42 | up |
| hsa-miR-18b | 2.72 | up |
| hsa-miR-193a | 2.07 | up |
| hsa-miR-19a | 6.04 | up |
| hsa-miR-19b | 2.88 | up |
| hsa-miR-212 | 5.22 | up |
| hsa-miR-219 | 9.11 | up |

TABLE 4-continued

Differentially expressed microRNAs in minor salivary glands of Sjögren's syndrome patients with a high focus score/normal salivary flow (Normal) relative to Sjögren's syndrome patients with a high focus score/low salivary flow (Low)

| microRNA | Fold change (Normal vs. Low) | Regulation (Normal vs. Low) |
|---|---|---|
| hsa-miR-29b | 2.11 | up |
| hsa-miR-301 | 5.67 | up |
| hsa-miR-30e-5p | 3.24 | up |
| hsa-miR-32 | 2.67 | up |
| hsa-miR-33 | 8.89 | up |
| hsa-miR-376b | 3.57 | up |
| hsa-miR-377 | 3.75 | up |
| hsa-miR-590 | 2.04 | up |

Table 5 provides a list of microRNAs that are differentially expressed in the minor salivary glands of Sjögren's syndrome patients with a low focus score and normal salivary flow, relative to Sjögren's syndrome patients with a low focus score and low salivary flow. Shown are microRNAs exhibiting a 1.5-fold or greater increase or decrease in expression (statistical significance set at p=0.05). Also listed is the fold-change in microRNA expression (middle column) and whether the microRNA is up-regulated ("up") or down-regulated ("down") in Sjögren's syndrome patients with low focus score/normal salivary flow compared to low focus score/low salivary flow (right column). In this table, hsa-mir-330 is 2-fold downregulated in the Sjögren's syndrome patients with a low focus score and normal salivary flow, compared to Sjögren's syndrome patients with a low focus score and low salivary flow. In addition, hsa-mir-340 is 1.6-fold upregulated in the Sjögren's syndrome patients with a low focus score and normal salivary flow relative to Sjögren's syndrome patients with a low focus score and low salivary flow.

TABLE 5

Differentially expressed microRNAs in minor salivary glands of Sjögren's syndrome patients with a low focus score/normal salivary flow (Normal) relative to Sjögren's syndrome patients with a low focus score/low salivary flow (Low)

| microRNA | Fold change (Normal vs. Low) | Regulation (Normal vs. Low) |
|---|---|---|
| hsa-miR-330 | 1.99 | down |
| hsa-miR-340 | 1.61 | up |

Table 6 provides a list of microRNAs that are differentially expressed in the minor salivary glands of Sjögren's syndrome patients with a low focus score, relative to Sjögren's syndrome patients with a high focus score. Shown are microRNAs exhibiting a 2-fold or greater increase or decrease in expression (statistical significance set at p=0.05). Also listed is the fold-change in microRNA expression (middle column) and whether the microRNA is up-regulated ("up") or down-regulated ("down") in Sjögren's syndrome patients with low focus score compared to high focus score (right column).

TABLE 6

Differentially expressed microRNAs in minor salivary glands of Sjögren's syndrome patients with a low focus score to Sjögren's syndrome patients with a high focus score

| microRNA | Fold change (Low vs. High) | Regulation (Low vs. High) |
|---|---|---|
| hsa-miR-126* | 2.94 | down |
| hsa-miR-135b | 2.27 | down |
| hsa-miR-141 | 2.95 | up |
| hsa-miR-142-3p | 5.16 | down |
| hsa-miR-142-5p | 4.74 | down |
| hsa-miR-143 | 2.15 | up |
| hsa-miR-146b | 2.97 | down |
| hsa-miR-148a | 2.63 | up |
| hsa-miR-150 | 7.73 | down |
| hsa-miR-154* | 2.09 | up |
| hsa-miR-155 | 5.84 | down |
| hsa-miR-181a* | 2.48 | down |
| hsa-miR-189 | 2.51 | up |
| hsa-miR-200a | 2.16 | up |
| hsa-miR-21 | 2.49 | down |
| hsa-miR-219 | 3.89 | up |
| hsa-miR-223 | 2.57 | down |
| hsa-miR-299-3p | 3.10 | up |
| hsa-miR-299-5p | 2.19 | up |
| hsa-miR-324-3p | 2.09 | down |
| hsa-miR-329 | 2.71 | up |
| hsa-miR-335 | 2.25 | up |
| hsa-miR-338 | 3.59 | up |
| hsa-miR-342 | 3.07 | down |
| hsa-miR-375 | 3.17 | up |
| hsa-miR-376b | 2.7 | up |
| hsa-miR-377 | 3.47 | up |
| hsa-miR-381 | 2.03 | up |
| hsa-miR-410 | 2.45 | up |
| hsa-miR-411 | 2.08 | up |
| hsa-miR-493-5p | 2.42 | up |
| hsa-miR-495 | 2.39 | up |
| hsa-miR-551b | 2.07 | up |
| hsa-miR-650 | 5.94 | down |
| hsa-miR-766 | 2.88 | down |
| hsa-miR-768-5p | 2.09 | down |
| hsa-miR-92b | 2.88 | down |

Example 3

Class Prediction Analysis of Differentially Expressed MicroRNAs

This example describes class prediction of analysis of microRNAs that are differentially expressed in patients with Sjögren's syndrome compared with healthy control subjects.
Description of the Problem
 Number of classes: 2
 Number of genes that passed filtering criteria: 243
 Experiment descriptors that define class variables: SS (Sjögren's syndrome) vs. N (Normal Volunteers)
 Number of arrays in each class: 8 in class label N, 16 in class label S
Feature Selection Criteria
 Genes significantly different between the classes at 0.001 significance level were used for class prediction.
Cross-Validation Method
 Leave-one-out cross-validation method was used to compute mis-classification rate. T-values used for the (Bayesian) compound covariate predictor were truncated at abs(t)=10 level. Equal class prevalence is used in the Bayesian compound covariate predictor. Threshold of predicted probability for a sample being predicted to a class from the Bayesian compound covariate predictor is 0.8.

TABLE 7

Performance of classifiers during cross-validation

| | Array ID | Class label | Mean Number of genes in classifier | Compound Covariate Predictor Correct? | Diagonal Linear Discriminant Analysis Correct? | 1-Nearest Neighbor Correct? | 3-Nearest Neighbors Correct? | Nearest Centroid Correct? | Support Vector Machines Correct? | Bayesian Compound Covariate Predictor Correct? |
|---|---|---|---|---|---|---|---|---|---|---|
| 1 | 2A-1 | N | 52 | YES | YES | YES | YES | YES | YES | YES |
| 2 | 2A-2 | N | 54 | YES | YES | YES | YES | YES | YES | YES |
| 3 | 2A-3 | N | 51 | YES | YES | YES | YES | YES | YES | YES |
| 4 | 2A-4 | N | 50 | YES | YES | YES | YES | YES | YES | YES |
| 5 | 2A-5 | N | 55 | YES | YES | YES | YES | YES | YES | YES |
| 6 | 2A-6 | N | 53 | YES | YES | YES | YES | YES | YES | YES |
| 7 | 2A-7 | N | 53 | YES | YES | YES | YES | YES | YES | YES |
| 8 | 2A-8 | N | 56 | YES | YES | YES | YES | YES | YES | YES |
| 9 | 1A-1 | S | 54 | YES | YES | YES | YES | YES | YES | YES |
| 10 | 1A-2 | S | 53 | YES | YES | YES | YES | YES | YES | YES |
| 11 | 1A-3 | S | 55 | YES | YES | YES | YES | YES | YES | YES |
| 12 | 1A-4 | S | 55 | YES | YES | YES | YES | YES | YES | YES |
| 13 | 1B-1 | S | 54 | YES | YES | YES | YES | YES | YES | YES |
| 14 | 1B-2 | S | 54 | YES | YES | YES | YES | YES | YES | YES |
| 15 | 1B-3 | S | 56 | YES | YES | YES | YES | YES | YES | YES |
| 16 | 1B-4 | S | 54 | YES | YES | YES | YES | YES | YES | YES |
| 17 | 1C-1 | S | 53 | YES | YES | YES | YES | YES | YES | YES |
| 18 | 1C-2 | S | 53 | YES | YES | YES | YES | YES | YES | YES |
| 19 | 1C-3 | S | 54 | YES | YES | YES | YES | YES | YES | YES |
| 20 | 1C-4 | S | 58 | YES | YES | YES | YES | YES | YES | YES |
| 21 | 1D-1 | S | 54 | YES | YES | YES | YES | YES | YES | YES |
| 22 | 1D-2 | S | 55 | YES | YES | YES | YES | YES | YES | YES |
| 23 | 1D-3 | S | 54 | YES | YES | YES | YES | YES | YES | YES |
| 24 | 1D-4 | S | 53 | YES | YES | YES | YES | YES | YES | YES |
| Mean percent of correct classification: | | | | 100 | 100 | 100 | 100 | 100 | 100 | 100 |

TABLE 8

Predicted probability of each sample belonging to the class (N) during cross-validation from the Bayesian Compound Covariate

| | Array ID | Class label | Probability |
|---|---|---|---|
| 1 | 2A-1 | N | 1 |
| 2 | 2A-2 | N | 0.995 |
| 3 | 2A-3 | N | 1 |
| 4 | 2A-4 | N | 1 |
| 5 | 2A-5 | N | 0.984 |
| 6 | 2A-6 | N | 0.995 |
| 7 | 2A-7 | N | 0.933 |
| 8 | 2A-8 | N | 1 |
| 9 | 1A-1 | S | 0.004 |
| 10 | 1A-2 | S | p < 1.0e−3 |
| 11 | 1A-3 | S | 0.002 |
| 12 | 1A-4 | S | 0.002 |
| 13 | 1B-1 | S | p < 1.0e−3 |
| 14 | 1B-2 | S | p < 1.0e−3 |
| 15 | 1B-3 | S | 0.004 |
| 16 | 1B-4 | S | p < 1.0e−3 |
| 17 | 1C-1 | S | p < 1.0e−3 |
| 18 | 1C-2 | S | p < 1.0e−3 |
| 19 | 1C-3 | S | p < 1.0e−3 |
| 20 | 1C-4 | S | p < 1.0e−3 |
| 21 | 1D-1 | S | p < 1.0e−3 |
| 22 | 1D-2 | S | 0.578 |
| 23 | 1D-3 | S | 0.001 |
| 24 | 1D-4 | S | p < 1.0e−3 |

Performance of classifiers during cross-validation:
Let, for some class A,
  $n11$ = number of class A samples predicted as A
  $n12$ = number of class A samples predicted as non-A
  $n21$ = number of non-A samples predicted as A
  $n22$ = number of non-A samples predicted as non-A
Then the following parameters can characterize performance of classifiers:

Sensitivity = $n11/(n11+n12)$

Specificity = $n22/(n21+n22)$

Positive Predictive Value (PPV) = $n11/(n11+n21)$

Negative Predictive Value (NPV) = $n22/(n12+n22)$

Sensitivity is the probability for a class A sample to be correctly predicted as class A. Specificity is the probability for a non-class A sample to be correctly predicted as non-A. PPV is the probability that a sample predicted as class A actually belongs to class A. NPV is the probability that a sample predicted as non class A actually does not belong to class A. For each classification method and each class, these parameters are listed in Tables 9-15 below.

TABLE 9

Performance of the Compound Covariate Predictor Classifier

| Class | Sensitivity | Specificity | PPV | NPV |
|---|---|---|---|---|
| N | 1 | 0.938 | 0.889 | 1 |
| S | 0.938 | 1 | 1 | 0.889 |

TABLE 10

Performance of the Diagonal Linear Discriminant Analysis Classifier

| Class | Sensitivity | Specificity | PPV | NPV |
|---|---|---|---|---|
| N | 1 | 0.938 | 0.889 | 1 |
| S | 0.938 | 1 | 1 | 0.889 |

TABLE 11

Performance of the 1-Nearest Neighbor Classifier

| Class | Sensitivity | Specificity | PPV | NPV |
|---|---|---|---|---|
| N | 1 | 1 | 1 | 1 |
| S | 1 | 1 | 1 | 1 |

TABLE 12

Performance of the 3-Nearest Neighbors Classifier

| Class | Sensitivity | Specificity | PPV | NPV |
|---|---|---|---|---|
| N | 1 | 1 | 1 | 1 |
| S | 1 | 1 | 1 | 1 |

TABLE 13

Performance of the Nearest Centroid Classifier

| Class | Sensitivity | Specificity | PPV | NPV |
|---|---|---|---|---|
| N | 1 | 1 | 1 | 1 |
| S | 1 | 1 | 1 | 1 |

TABLE 14

Performance of the Support Vector Machine Classifier

| Class | Sensitivity | Specificity | PPV | NPV |
|---|---|---|---|---|
| N | 1 | 1 | 1 | 1 |
| S | 1 | 1 | 1 | 1 |

TABLE 15

Performance of the Bayesian Compound Covariate Classifier

| Class | Sensitivity | Specificity | PPV | NPV |
|---|---|---|---|---|
| N | 1 | 0.938 | 0.889 | 1 |
| S | 0.938 | 1 | 1 | 0.889 |

TABLE 16

Composition of classifier sorted by t-value
(Class 1: N; Class 2: S)

| | Parametric p-value | t-value | % CV support | Geometric mean of intensities in class 1 | Geometric mean of intensities in class 2 | Fold-change | Unique ID |
|---|---|---|---|---|---|---|---|
| 1 | <1e-07 | -19.913 | 100 | 5.5241175 | 59.5056631 | 0.0928335 | has-miR-564 |
| 2 | <1e-07 | -12.584 | 100 | 11.9890257 | 74.7074619 | 0.1604796 | has-miR-202 |
| 3 | <1e-07 | -12.393 | 100 | 11.2173002 | 184.6447397 | 0.0607507 | ebv-miR-BART13 |
| 4 | <1e-07 | -10.332 | 100 | 237.2948572 | 2474.3770109 | 0.0959008 | hsa-miR-768-3p |
| 5 | <1e-07 | -9.216 | 100 | 21.6270531 | 173.2018822 | 0.1248662 | kshv-miR-K12-3 |
| 6 | <1e-07 | -9.176 | 100 | 5.9250124 | 261.6543655 | 0.0226444 | hsa-miR-150 |
| 7 | <1e-07 | -8.705 | 100 | 8.0750164 | 73.7203109 | 0.1095358 | hsa-miR-126* |
| 8 | <1e-07 | -8.426 | 100 | 40.8067279 | 364.8262333 | 0.1118525 | hsa-miR-30b |
| 9 | <1e-07 | -8.3 | 100 | 4.9999998 | 18.6015032 | 0.2687955 | hsa-miR-509 |
| 10 | <1e-07 | -8.287 | 100 | 7.3855007 | 591.3997331 | 0.0124882 | ebv-miR-BART19 |
| 11 | <1e-07 | -8.085 | 100 | 18.5178779 | 222.9427324 | 0.0830611 | hsa-miR-575 |
| 12 | <1e-07 | -7.887 | 100 | 6.6246641 | 32.1542068 | 0.2060279 | hsa-miR-198 |
| 13 | <1e-07 | -7.873 | 100 | 11.2819874 | 73.1778723 | 0.1541721 | hsa-miR-188 |
| 14 | <1e-07 | -7.802 | 100 | 12.8351793 | 59.5858888 | 0.2154064 | hsa-miR-99b |
| 15 | 1e-07 | -7.706 | 100 | 74.2764302 | 1203.7490091 | 0.0617043 | hsa-miR-565 |
| 16 | 3e-07 | -7.198 | 100 | 9.6145063 | 152.6015126 | 0.063004 | hsa-miR-801 |
| 17 | 5e-07 | -7.033 | 100 | 25.4812571 | 236.5038022 | 0.1077414 | hsa-miR-342 |
| 18 | 7e-07 | -6.836 | 100 | 7.0535643 | 82.889604 | 0.0850959 | hsa-miR-513 |
| 19 | 9e-07 | -6.742 | 100 | 41.1443954 | 155.4505405 | 0.2646784 | hsa-miR-181a |

TABLE 16-continued

Composition of classifier sorted by t-value
(Class 1: N; Class 2: S)

| | Parametric p-value | t-value | % CV support | Geometric mean of intensities in class 1 | Geometric mean of intensities in class 2 | Fold-change | Unique ID |
|---|---|---|---|---|---|---|---|
| 20 | 9e−07 | −6.74 | 100 | 95.6760941 | 1672.6335028 | 0.0572009 | hsa-miR-494 |
| 21 | 2.7e−06 | −6.251 | 100 | 46.6001099 | 185.0020252 | 0.2518897 | hsa-miR-30c |
| 22 | 4.1e−06 | −6.071 | 100 | 57.873233 | 269.4701022 | 0.2147668 | hsa-miR-324-3p |
| 23 | 4.3e−06 | −6.05 | 100 | 32.0130118 | 281.2450848 | 0.113826 | hsa-miR-370 |
| 24 | 4.5e−06 | −6.037 | 100 | 5.7295189 | 17.1161591 | 0.3347433 | hsa-miR-601 |
| 25 | 5.2e−06 | −5.976 | 100 | 318.5322501 | 1785.1932047 | 0.1784301 | hsa-miR-205 |
| 26 | 6.2e−06 | −5.896 | 100 | 14.2692693 | 44.7856463 | 0.3186126 | hsa-miR-484 |
| 27 | 9.8e−06 | −5.7 | 100 | 10.4022733 | 47.0205561 | 0.2212282 | hsa-miR-31 |
| 28 | 1.04e−05 | −5.677 | 100 | 107.3718015 | 494.2155634 | 0.217257 | hsa-miR-222 |
| 29 | 1.05e−05 | −5.673 | 100 | 6.3259882 | 19.654447 | 0.3218604 | hsa-miR-194 |
| 30 | 1.13e−05 | −5.641 | 100 | 7.9292129 | 24.7136315 | 0.3208437 | hsa-miR-132 |
| 31 | 1.35e−05 | −5.567 | 100 | 7.5556921 | 20.7830593 | 0.3635505 | hsa-miR-154 |
| 32 | 1.5e−05 | −5.524 | 100 | 57.3364859 | 278.9619288 | 0.2055352 | hsa-miR-374 |
| 33 | 1.67e−05 | −5.478 | 100 | 4.9999998 | 12.4378626 | 0.4019983 | hsa-miR-584 |
| 34 | 1.87e−05 | −5.431 | 100 | 7.8525652 | 22.1907384 | 0.3538668 | hsa-miR-128b |
| 35 | 2.79e−05 | −5.263 | 100 | 7.0171501 | 18.1734834 | 0.3861203 | hsa-miR-128a |
| 36 | 3.98e−05 | −5.116 | 100 | 153.2933399 | 656.6720196 | 0.2334397 | hsa-miR-199a |
| 37 | 4.32e−05 | −5.083 | 100 | 674.3354605 | 2276.1579149 | 0.2962604 | hsa-miR-16 |
| 38 | 4.81e−05 | −5.037 | 100 | 24.4518076 | 86.0572969 | 0.284134 | hsa-miR-425-5p |
| 39 | 5.09e−05 | −5.014 | 100 | 87.1332823 | 251.7419015 | 0.3461215 | hsa-miR-572 |
| 40 | 5.17e−05 | −5.008 | 100 | 19.7102093 | 67.2547374 | 0.293068 | hsa-miR-127 |
| 41 | 6.81e−05 | −4.894 | 100 | 7.9933323 | 27.0313443 | 0.2957061 | hsa-miR-135b |
| 42 | 7.23e−05 | −4.87 | 100 | 34.6262662 | 97.3738267 | 0.3556014 | hsa-miR-181b |
| 43 | 7.29e−05 | −4.866 | 100 | 5.6572205 | 12.2698696 | 0.4610661 | hsa-miR-501 |
| 44 | 7.36e−05 | −4.862 | 100 | 50.7648598 | 192.3501575 | 0.263919 | hsa-miR-93 |
| 45 | 7.74e−05 | −4.841 | 100 | 81.1424185 | 263.3956405 | 0.3080629 | hsa-miR-191 |
| 46 | 7.91e−05 | −4.832 | 100 | 8.2243825 | 29.1506073 | 0.2821342 | hsa-miR-452 |
| 47 | 0.0001012 | −4.731 | 100 | 5.0174892 | 12.7221389 | 0.3943904 | hsa-miR-622 |
| 48 | 0.0001023 | −4.727 | 100 | 5.6891867 | 16.9465604 | 0.3357134 | hsv1-miR-H1 |
| 49 | 0.0001095 | −4.699 | 100 | 5.2296051 | 9.5573792 | 0.5471798 | hsa-miR-382 |
| 50 | 0.0001226 | −4.652 | 100 | 18.415451 | 69.5909024 | 0.2646244 | hsa-miR-671 |
| 51 | 0.0001366 | −4.608 | 100 | 43.8080495 | 162.9286348 | 0.2688788 | hsa-miR-221 |
| 52 | 0.0001763 | −4.504 | 100 | 44.6583744 | 179.5059098 | 0.248785 | hsa-miR-146b |
| 53 | 0.0001991 | −4.454 | 100 | 91.7983939 | 741.4785293 | 0.1238045 | hsa-miR-142-5p |
| 54 | 0.0002069 | −4.438 | 100 | 20.2113473 | 67.4569879 | 0.2996183 | hsa-miR-487b |
| 55 | 0.0002091 | −4.434 | 100 | 271.7737125 | 790.2892508 | 0.3438914 | hsa-miR-103 |

TABLE 16-continued

Composition of classifier sorted by t-value
(Class 1: N; Class 2: S)

|  | Parametric p-value | t-value | % CV support | Geometric mean of intensities in class 1 | Geometric mean of intensities in class 2 | Fold-change | Unique ID |
|---|---|---|---|---|---|---|---|
| 56 | 0.0002223 | −4.409 | 100 | 7.588859 | 20.8640422 | 0.3637291 | hcmv-miR-US4 |
| 57 | 0.0002711 | −4.328 | 100 | 4.9999998 | 9.1239309 | 0.5480094 | hsa-miR-512-3p |
| 58 | 0.000311 | −4.271 | 100 | 4.9999998 | 12.1781915 | 0.41057 | hsa-miR-455 |
| 59 | 0.0003724 | −4.198 | 88 | 26.6907437 | 96.0265923 | 0.2779516 | hsa-miR-663 |
| 60 | 0.0003737 | −4.196 | 92 | 8.9999567 | 25.6777388 | 0.3504965 | hsa-miR-766 |
| 61 | 0.0003874 | −4.181 | 96 | 143.0377161 | 435.1631548 | 0.3286991 | hsa-miR-25 |
| 62 | 0.0006798 | −3.951 | 42 | 720.3467022 | 1585.826905 | 0.4542404 | hsa-miR-638 |
| 63 | 0.0007917 | −3.888 | 29 | 4.9999998 | 12.8942834 | 0.3877687 | hsa-miR-212 |
| 64 | 0.0008459 | −3.861 | 29 | 231.0837838 | 693.6555087 | 0.3331391 | hsa-miR-100 |
| 65 | 0.0008806 | −3.844 | 29 | 6.954571 | 15.746096 | 0.4416695 | hsa-miR-409-3p |
| 66 | 0.0008812 | −3.844 | 29 | 133.8146959 | 368.2814467 | 0.363349 | hsa-miR-106a |
| 67 | 0.0002201 | 4.413 | 100 | 704.7961012 | 224.9017337 | 3.1337958 | hsa-miR-768-5p |

Prediction Rule from the Linear Predictors

The prediction rule is defined by the inner sum of the weights ($w_i$) and expression ($x_i$) of significant genes. The expression is the log ratios for dual-channel data and log intensities for single-channel data. A sample is classified to the class N if the sum is greater than the threshold (i.e., $\Sigma_i w_i x_i$ threshold). The threshold for the Compound Covariate predictor is −2237.041; the threshold for the Diagonal Linear Discriminant predictor is −1226.374; and the threshold for the Support Vector Machine predictor is −3.933.

TABLE 17

Gene Weights

|  | Genes | Compound Covariate Predictor | Diagonal Linear Discriminant Analysis | Support Vector Machines |
|---|---|---|---|---|
| 1 | ebv-miR-BART13 | −12.393 | −7.1263 | −0.0432 |
| 2 | ebv-miR-BART19 | −8.2873 | −2.0365 | −0.0868 |
| 3 | hcmv-miR-US4 | −4.4087 | −2.4977 | 0.0048 |
| 4 | hsa-miR-100 | −3.8611 | −1.7627 | 0.0076 |
| 5 | hsa-miR-103 | −4.4339 | −2.3936 | 0.0043 |
| 6 | hsa-miR-106a | −3.8442 | −1.8971 | 0.0113 |
| 7 | hsa-miR-126* | −8.7053 | −4.4536 | −0.0448 |
| 8 | hsa-miR-127 | −5.008 | −2.6558 | −3e−04 |
| 9 | hsa-miR-128a | −5.2633 | −3.7834 | 0.0028 |
| 10 | hsa-miR-128b | −5.4314 | −3.6906 | 0.002 |
| 11 | hsa-miR-132 | −5.6412 | −3.6381 | −0.005 |
| 12 | hsa-miR-135b | −4.8941 | −2.555 | −0.0148 |
| 13 | hsa-miR-142-5p | −4.4539 | −1.2341 | −0.0168 |
| 14 | hsa-miR-146b | −4.5036 | −1.8948 | −0.007 |
| 15 | hsa-miR-150 | −9.1763 | −2.8891 | −0.0909 |
| 16 | hsa-miR-154 | −5.5667 | −3.9803 | −0.0066 |
| 17 | hsa-miR-16 | −5.0825 | −2.7597 | 0.0037 |
| 18 | hsa-miR-181a | −6.7422 | −4.4445 | −0.047 |
| 19 | hsa-miR-181b | −4.8696 | −2.9807 | 0.0011 |
| 20 | hsa-miR-188 | −7.8734 | −4.3091 | −0.0237 |
| 21 | hsa-miR-191 | −4.8414 | −2.5872 | 0.0014 |
| 22 | hsa-miR-194 | −5.6728 | −3.6893 | −0.0015 |
| 23 | hsa-miR-198 | −7.8872 | −5.1178 | −0.0138 |

TABLE 17-continued

Gene Weights

|  | Genes | Compound Covariate Predictor | Diagonal Linear Discriminant Analysis | Support Vector Machines |
|---|---|---|---|---|
| 24 | hsa-miR-199a | −5.1165 | −2.3386 | −9e−04 |
| 25 | hsa-miR-202 | −12.584 | −11.248 | −0.0302 |
| 26 | hsa-miR-205 | −5.976 | −2.6929 | −0.0156 |
| 27 | hsa-miR-212 | −3.8883 | −2.0741 | −0.0058 |
| 28 | hsa-miR-221 | −4.6081 | −2.1011 | 0.0045 |
| 29 | hsa-miR-222 | −5.677 | −2.7436 | −0.0096 |
| 30 | hsa-miR-25 | −4.1814 | −2.0423 | 0.0069 |
| 31 | hsa-miR-30b | −8.4256 | −4.2118 | −0.0279 |
| 32 | hsa-miR-30c | −6.2512 | −3.6836 | −0.0106 |
| 33 | hsa-miR-31 | −5.7004 | −2.7995 | −0.0105 |
| 34 | hsa-miR-324-3p | −6.0706 | −3.1137 | −0.0107 |
| 35 | hsa-miR-342 | −7.0331 | −2.8854 | −0.026 |
| 36 | hsa-miR-370 | −6.0502 | −2.1892 | −0.0182 |
| 37 | hsa-miR-374 | −5.5241 | −2.5068 | −0.007 |
| 38 | hsa-miR-382 | −4.6987 | −4.7587 | −0.0031 |
| 39 | hsa-miR-409-3p | −3.8445 | −2.3506 | 0.004 |
| 40 | hsa-miR-425-5p | −5.0375 | −2.621 | 0.0033 |
| 41 | hsa-miR-452 | −4.8324 | −2.3984 | 0.0063 |
| 42 | hsa-miR-455 | −4.2713 | −2.6635 | −0.0092 |
| 43 | hsa-miR-484 | −5.8958 | −3.9497 | −0.0076 |
| 44 | hsa-miR-487b | −4.4382 | −2.1241 | 0.0086 |
| 45 | hsa-miR-494 | −6.7399 | −2.0634 | −0.0302 |
| 46 | hsa-miR-501 | −4.8658 | −3.9745 | −0.0063 |
| 47 | hsa-miR-509 | −8.3001 | −6.815 | −0.018 |
| 48 | hsa-miR-512-3p | −4.3275 | −4.0467 | −0.0021 |
| 49 | hsa-miR-513 | −6.8361 | −2.4649 | −0.0413 |
| 50 | hsa-miR-564 | −19.913 | −21.682 | −0.0451 |
| 51 | hsa-miR-565 | −7.7056 | −2.7705 | −0.0335 |
| 52 | hsa-miR-572 | −5.0143 | −3.0799 | −0.0063 |
| 53 | hsa-miR-575 | −8.0849 | −3.4143 | −0.0365 |
| 54 | hsa-miR-584 | −5.4781 | −4.2797 | −0.0045 |
| 55 | hsa-miR-601 | −6.0374 | −4.3286 | −0.0042 |
| 56 | hsa-miR-622 | −4.7311 | −3.1267 | −0.0052 |
| 57 | hsa-miR-638 | −3.9509 | −2.5708 | −8e−04 |
| 58 | hsa-miR-663 | −4.1975 | −1.7886 | 0.0036 |
| 59 | hsa-miR-671 | −4.6525 | −2.116 | −0.0011 |

TABLE 17-continued

Gene Weights

| | Genes | Compound Covariate Predictor | Diagonal Linear Discriminant Analysis | Support Vector Machines |
|---|---|---|---|---|
| 60 | hsa-miR-766 | −4.1962 | −2.1827 | −0.0018 |
| 61 | hsa-miR-768-3p | −10.332 | −5.9179 | −0.0319 |
| 62 | hsa-miR-768-5p | 4.4127 | 2.2155 | 0.0638 |
| 63 | hsa-miR-801 | −7.1982 | −2.4358 | −0.0201 |
| 64 | hsa-miR-93 | −4.862 | −2.3063 | 0.0016 |
| 65 | hsa-miR-99b | −7.8025 | −5.1537 | −0.0233 |
| 66 | hsv1-miR-H1 | −4.7268 | −2.6604 | 0.0065 |
| 67 | kshv-miR-K12-3 | −9.2165 | −5.3062 | −0.023 |

TABLE 18

Normalized Log-Transformed Median-Centered Gene Expressions for Significant Genes

| | Experiment | 2A-1 | 2A-2 | 2A-3 | 2A-4 | 2A-5 | 2A-6 | 2A-7 | 2A-8 | 1A-1 | 1A-2 | 1A-3 | 1A-4 | 1B-1 | 1B-2 |
|---|---|---|---|---|---|---|---|---|---|---|---|---|---|---|---|
| | Class | N | N | N | N | N | N | N | N | S | S | S | S | S | S |
| 1 | ebv-miR-BART13 | 2.322 | 3.876 | 3.539 | 3.734 | 3.996 | 3.765 | 4.347 | 2.322 | 7.393 | 7.703 | 7.225 | 7.15 | 9.299 | 8.306 |
| 2 | ebv-miR-BART19 | 2.322 | 2.322 | 2.463 | 2.322 | 3.354 | 4.61 | 3.363 | 2.322 | 7.41 | 9.247 | 7.268 | 7.969 | 12.138 | 11.721 |
| 3 | hcmv-miR-US4 | 2.322 | 4.065 | 2.322 | 3.224 | 2.322 | 2.322 | 4.492 | 2.322 | 4.843 | 4.724 | 4.599 | 4.724 | 5.309 | 4.879 |
| 4 | hsa-miR-100 | 6.086 | 8.48 | 7.378 | 7.903 | 9.488 | 9.095 | 8.794 | 5.595 | 9.339 | 9.87 | 9.701 | 9.899 | 8.426 | 10.485 |
| 5 | hsa-miR-103 | 6.83 | 8.777 | 7.834 | 8.245 | 9.244 | 8.984 | 9.069 | 5.708 | 9.364 | 9.739 | 9.733 | 9.526 | 8.894 | 10.365 |
| 6 | hsa-miR-106a | 6.064 | 7.661 | 7.163 | 7.704 | 7.871 | 7.795 | 7.953 | 4.303 | 8.346 | 8.824 | 8.755 | 8.553 | 7.884 | 9.493 |
| 7 | hsa-miR-126* | 2.322 | 3.542 | 2.831 | 2.958 | 3.554 | 3.427 | 3.152 | 2.322 | 5.091 | 5.598 | 5.587 | 6.061 | 4.502 | 6.395 |
| 8 | hsa-miR-127 | 2.322 | 5.267 | 4.045 | 4.288 | 5.072 | 4.997 | 5.622 | 2.794 | 6.354 | 6.913 | 6.242 | 5.895 | 5.826 | 7.16 |
| 9 | hsa-miR-128a | 2.322 | 2.754 | 2.322 | 2.66 | 3.459 | 3.276 | 3.372 | 2.322 | 4.037 | 4.448 | 4.441 | 4.184 | 2.79 | 5.234 |
| 10 | hsa-miR-128b | 2.322 | 3.092 | 2.322 | 2.831 | 3.759 | 3.526 | 3.61 | 2.322 | 4.198 | 4.461 | 4.726 | 4.375 | 3.111 | 5.515 |
| 11 | hsa-miR-132 | 2.322 | 3.433 | 2.322 | 2.322 | 4.303 | 3.388 | 3.486 | 2.322 | 4.238 | 4.782 | 4.782 | 4.132 | 3.48 | 5.272 |
| 12 | hsa-miR-135b | 2.547 | 3.66 | 2.581 | 2.322 | 3.509 | 3.446 | 3.604 | 2.322 | 4.46 | 4.723 | 5.219 | 4.055 | 2.589 | 4.847 |
| 13 | hsa-miR-142-5p | 6.143 | 7.669 | 7.827 | 6.666 | 6.521 | 6.491 | 6.654 | 4.192 | 7.488 | 9.715 | 9.121 | 7.043 | 8.312 | 9.012 |
| 14 | hsa-miR-146b | 4.616 | 6.214 | 5.234 | 5.44 | 6.538 | 6.44 | 6.075 | 3.29 | 6.228 | 7.712 | 7.085 | 5.934 | 6.219 | 7.531 |
| 15 | hsa-miR-150 | 2.322 | 2.322 | 2.446 | 2.322 | 3.369 | 3.109 | 2.322 | 2.322 | 5.695 | 8.026 | 6.934 | 5.771 | 6.449 | 7.246 |
| 16 | hsa-miR-154 | 2.322 | 3.399 | 2.322 | 2.844 | 3.272 | 3.154 | 3.706 | 2.322 | 4.712 | 4.99 | 4.542 | 4.366 | 3.718 | 5.605 |
| 17 | hsa-miR-16 | 8.35 | 9.78 | 9.53 | 9.709 | 10.257 | 9.787 | 10.347 | 7.419 | 10.403 | 11.006 | 10.943 | 10.698 | 10.271 | 11.568 |
| 18 | hsa-miR-181a | 3.919 | 5.739 | 4.933 | 5.554 | 5.862 | 6.106 | 6.446 | 4.344 | 6.634 | 7.381 | 7.016 | 6.79 | 6.693 | 7.734 |
| 19 | hsa-miR-181b | 3.78 | 5.466 | 4.856 | 5.374 | 6.156 | 5.906 | 6.004 | 3.368 | 5.859 | 7.109 | 6.636 | 6.269 | 5.939 | 7.07 |
| 20 | hsa-miR-188 | 2.322 | 3.969 | 3.536 | 3.825 | 3.983 | 3.673 | 4.338 | 2.322 | 5.449 | 6.308 | 5.402 | 5.729 | 8.545 | 6.182 |
| 21 | hsa-miR-191 | 4.984 | 6.895 | 6.323 | 6.721 | 7.419 | 7.126 | 7.441 | 3.83 | 7.765 | 8.113 | 8.149 | 7.875 | 7.354 | 8.57 |
| 22 | hsa-miR-194 | 2.322 | 3.036 | 2.322 | 2.654 | 2.946 | 2.813 | 2.875 | 2.322 | 4.015 | 4.493 | 4.372 | 3.922 | 3.856 | 5.182 |
| 23 | hsa-miR-198 | 2.322 | 3.234 | 2.322 | 2.654 | 2.322 | 2.322 | 4.325 | 2.322 | 4.493 | 4.975 | 3.825 | 4.898 | 6.001 | 5.209 |
| 24 | hsa-miR-199a | 5.775 | 7.959 | 6.837 | 7.11 | 9.112 | 8.189 | 7.982 | 5.118 | 8.758 | 9.907 | 9.469 | 9.469 | 8.208 | 10.042 |
| 25 | hsa-miR-202 | 3.107 | 3.943 | 3.953 | 3.831 | 3.815 | 3.605 | 4.093 | 2.322 | 6.2 | 6.24 | 6.135 | 6.285 | 6.447 | 6.872 |
| 26 | hsa-miR-205 | 5.875 | 8.981 | 8.225 | 8.438 | 9.86 | 9.286 | 9.716 | 6.141 | 10.676 | 11.045 | 11.198 | 11.186 | 9.923 | 11.523 |
| 27 | hsa-miR-212 | 2.322 | 2.322 | 2.322 | 2.322 | 2.322 | 2.322 | 2.322 | 2.322 | 3.647 | 3.728 | 3.631 | 3.447 | 3.807 | 4.413 |
| 28 | hsa-miR-221 | 4.063 | 6.291 | 5.2 | 5.1 | 6.966 | 6.388 | 6.831 | 2.785 | 7.069 | 7.633 | 7.237 | 7.151 | 6.107 | 7.841 |
| 29 | hsa-miR-222 | 4.93 | 7.506 | 6.424 | 6.421 | 8.347 | 7.815 | 7.948 | 4.58 | 8.384 | 9.127 | 8.755 | 8.406 | 7.894 | 9.287 |
| 30 | hsa-miR-25 | 5.719 | 7.764 | 7.152 | 7.579 | 8.309 | 8.114 | 8.187 | 4.457 | 8.456 | 8.778 | 8.863 | 8.641 | 7.957 | 9.584 |
| 31 | hsa-miR-30b | 3.962 | 6.39 | 5.52 | 5.878 | 5.664 | 6.041 | 6.444 | 2.907 | 8.826 | 9.022 | 9.071 | 8.676 | 8.346 | 9.448 |
| 32 | hsa-miR-30c | 4.074 | 6.423 | 5.427 | 5.931 | 6.205 | 6.239 | 6.212 | 3.827 | 7.827 | 8.07 | 8.122 | 7.683 | 7.528 | 8.448 |
| 33 | hsa-miR-31 | 2.322 | 3.85 | 2.393 | 2.509 | 4.984 | 4.531 | 4.12 | 2.322 | 5.077 | 5.459 | 5.651 | 4.827 | 3.998 | 6.161 |
| 34 | hsa-miR-324-3p | 4.637 | 6.272 | 5.827 | 6.122 | 6.86 | 6.509 | 6.623 | 3.989 | 7.626 | 7.6 | 7.775 | 7.637 | 7.135 | 8.627 |
| 35 | hsa-miR-342 | 3.019 | 5.248 | 4.77 | 4.593 | 5.77 | 5.992 | 5.502 | 2.477 | 6.78 | 7.762 | 7.471 | 6.693 | 6.965 | 7.998 |
| 36 | hsa-miR-370 | 3.445 | 5.387 | 5.101 | 5.395 | 5.596 | 5.849 | 6.172 | 3.059 | 6.947 | 8.532 | 6.758 | 7.508 | 10.557 | 9.257 |
| 37 | hsa-miR-374 | 5.001 | 6.989 | 6.197 | 6.698 | 5.932 | 6.221 | 6.422 | 3.271 | 8.089 | 8.144 | 8.553 | 8.375 | 7.323 | 8.927 |
| 38 | hsa-miR-382 | 2.322 | 2.508 | 2.322 | 2.322 | 2.366 | 2.322 | 2.61 | 2.322 | 3.627 | 4.099 | 3.082 | 3.139 | 2.839 | 4.14 |
| 39 | hsa-miR-409-3p | 2.322 | 3.591 | 2.322 | 2.322 | 3.028 | 2.836 | 3.641 | 2.322 | 4.599 | 5.009 | 4.147 | 4.305 | 3.283 | 5.138 |
| 40 | hsa-miR-425-5p | 3.272 | 5.325 | 4.557 | 5.107 | 5.638 | 5.142 | 5.533 | 2.322 | 6.106 | 6.375 | 6.407 | 6.157 | 5.651 | 7.045 |
| 41 | hsa-miR-452 | 2.322 | 3.78 | 2.322 | 3.375 | 3.587 | 2.548 | 4.063 | 2.322 | 3.858 | 4.753 | 4.029 | 4.941 | 6.126 | 5.339 |
| 42 | hsa-miR-455 | 2.322 | 2.322 | 2.322 | 2.322 | 2.322 | 2.322 | 2.322 | 2.322 | 3.114 | 3.968 | 3.671 | 3.722 | 2.322 | 4.989 |
| 43 | hsa-miR-484 | 3.126 | 4.071 | 3.98 | 4.185 | 4.311 | 4.574 | 4.109 | 2.322 | 4.744 | 5.675 | 5.138 | 5.033 | 4.795 | 6.242 |
| 44 | hsa-miR-487b | 3.092 | 5.116 | 4.151 | 4.16 | 4.946 | 4.789 | 5.921 | 2.522 | 6.92 | 6.745 | 6.615 | 6.399 | 5.558 | 7.179 |
| 45 | hsa-miR-494 | 3.706 | 7.087 | 6.921 | 7.06 | 7.452 | 7.758 | 7.948 | 4.709 | 9.63 | 11.091 | 9.651 | 10.298 | 13.726 | 12.545 |
| 46 | hsa-miR-501 | 2.322 | 2.322 | 2.322 | 2.322 | 3.333 | 2.736 | 2.322 | 2.322 | 3.006 | 3.288 | 3.136 | 3.092 | 3.867 | 4.381 |
| 47 | hsa-miR-509 | 2.322 | 2.322 | 2.322 | 2.322 | 2.322 | 2.322 | 2.322 | 2.322 | 3.636 | 4.002 | 3.972 | 4.038 | 4.521 | 5.158 |
| 48 | hsa-miR-512-3p | 2.322 | 2.322 | 2.322 | 2.322 | 2.322 | 2.322 | 2.322 | 2.322 | 2.714 | 3.554 | 3.006 | 3.033 | 4.161 | 3.738 |
| 49 | hsa-miR-513 | 2.322 | 2.322 | 2.322 | 2.725 | 3.356 | 3.384 | 3.794 | 2.322 | 5.022 | 5.867 | 4.527 | 5.409 | 8.321 | 6.76 |
| 50 | hsa-miR-564 | 2.322 | 2.322 | 2.322 | 2.322 | 2.417 | 2.869 | 2.831 | 2.322 | 5.853 | 5.365 | 5.984 | 5.983 | 6.384 | 5.775 |
| 51 | hsa-miR-565 | 5.954 | 6.949 | 7.055 | 7.423 | 6.005 | 6.502 | 7.236 | 2.593 | 10.923 | 10.699 | 10.637 | 10.567 | 9.305 | 11.51 |

TABLE 18-continued

Normalized Log-Transformed Median-Centered Gene Expressions for Significant Genes

|   | Experiment | 2A-1 | 2A-2 | 2A-3 | 2A-4 | 2A-5 | 2A-6 | 2A-7 | 2A-8 | 1A-1 | 1A-2 | 1A-3 | 1A-4 | 1B-1 | 1B-2 |
|---|---|---|---|---|---|---|---|---|---|---|---|---|---|---|---|
| 52 | hsa-miR-572 | 5.776 | 7.025 | 6.673 | 7.305 | 6.427 | 6.106 | 7.218 | 5.031 | 7.253 | 8.768 | 7.643 | 8.613 | 8.668 | 8.321 |
| 53 | hsa-miR-575 | 2.551 | 5.337 | 4.394 | 4.778 | 4.347 | 3.959 | 5.961 | 2.36 | 7.083 | 7.18 | 6.21 | 7.938 | 8.98 | 7.884 |
| 54 | hsa-miR-584 | 2.322 | 2.322 | 2.322 | 2.322 | 2.322 | 2.322 | 2.322 | 2.322 | 2.846 | 4.241 | 3.362 | 3.832 | 3.703 | 4.698 |
| 55 | hsa-miR-601 | 2.322 | 2.817 | 2.322 | 2.322 | 2.497 | 2.322 | 3.223 | 2.322 | 3.213 | 4.198 | 3.48 | 3.489 | 4.565 | 4.359 |
| 56 | hsa-miR-622 | 2.322 | 2.322 | 2.322 | 2.322 | 2.322 | 2.322 | 2.362 | 2.322 | 3.243 | 3.748 | 3.055 | 3.275 | 5.387 | 4.552 |
| 57 | hsa-miR-638 | 8.853 | 10.072 | 9.61 | 10.195 | 9.651 | 9.287 | 10.176 | 8.097 | 10.02 | 11.387 | 10.327 | 11.094 | 11.489 | 11.193 |
| 58 | hsa-miR-663 | 2.322 | 5.86 | 5.077 | 5.695 | 4.237 | 3.592 | 6.646 | 4.477 | 5.936 | 6.642 | 5.445 | 7.019 | 6.48 | 6.461 |
| 59 | hsa-miR-671 | 2.322 | 5.67 | 4.407 | 5.069 | 3.341 | 3.591 | 6.188 | 3.036 | 5.635 | 6.006 | 5.032 | 5.851 | 6.577 | 6.194 |
| 60 | hsa-miR-766 | 2.322 | 3.939 | 3.133 | 3.489 | 2.89 | 3.295 | 3.969 | 2.322 | 3.863 | 4.97 | 3.673 | 3.56 | 4.384 | 4.002 |
| 61 | hsa-miR-768-3p | 6.293 | 8.442 | 7.728 | 8.022 | 8.923 | 8.719 | 8.897 | 6.099 | 10.922 | 11.23 | 11.223 | 10.853 | 10.626 | 11.683 |
| 62 | hsa-miR-768-5p | 9.176 | 9.526 | 9.409 | 9.856 | 10.11 | 9.846 | 10.204 | 7.562 | 6.92 | 7.501 | 7.079 | 7.234 | 7.624 | 8.35 |
| 63 | hsa-miR-801 | 2.322 | 4.016 | 2.979 | 3.751 | 2.56 | 2.862 | 4.796 | 2.836 | 6.282 | 7.742 | 5.459 | 6.432 | 8.237 | 8.588 |
| 64 | hsa-miR-93 | 4.509 | 6.247 | 5.723 | 6.241 | 6.858 | 6.483 | 6.59 | 2.676 | 7.339 | 7.696 | 7.804 | 7.579 | 6.837 | 8.491 |
| 65 | hsa-miR-99b | 2.322 | 3.908 | 3.356 | 3.576 | 4.847 | 4.799 | 4.327 | 2.322 | 5.545 | 5.953 | 5.932 | 5.712 | 5.028 | 6.621 |
| 66 | hsv1-miR-H1 | 2.322 | 2.486 | 2.322 | 2.322 | 2.322 | 2.322 | 3.648 | 2.322 | 3.312 | 4.178 | 2.717 | 3.434 | 5.512 | 4.913 |
| 67 | kshv-miRK12-3 | 2.786 | 4.842 | 4.753 | 4.901 | 4.821 | 4.945 | 5.352 | 3.076 | 7.18 | 7.503 | 7.318 | 7.362 | 9.039 | 7.802 |

Example 4

MicroRNA Profiling of Minor Salivary Glands of Sjögren's Syndrome Patients

Samples and Array Hybridization

Samples from a total of 24 minor salivary glands were hybridized on microRNA microarrays. Eight of these glands came from healthy controls and 16 from primary Sjögren's syndrome (SS) patients. Half of the primary Sjögren's samples had extensive inflammation with a focus score of 12, and half had low grade inflammation with focus scores of 1 or 2. Within both the high and low focus score groups, half of the patients had low salivary flow and half had preserved salivary flow (FIG. 1). Patients with these clinical parameters were selected to allow for the exploration of microRNA alterations not only between normal controls and SS patients but also to test if there is a difference in specific microRNAs patterns between patients with different degrees of inflammation or between hypofunctional salivary glands and salivary glands with preserved function in patients with similar level of inflammation.

Data Normalization

Normalization is an important step in microarray data analysis since it allows for the removal of systematic differences between samples that represent technical rather than biological variations. A major limitation in the interpretation of microRNA array data is the lack of a clear consensus on the utility and appropriateness of various normalization methods. Many of the classic normalization methods developed for the analysis of mRNA microarrays may not be appropriate to microRNA profiling because of the significant differences between microRNA and mRNA data sets (Pradervand et al., *RNA* 15:493-501, 2009). For example, compared to mRNAs, many microRNAs are expressed at very low levels or not at all, and there are many fewer microRNAs than mRNAs per array (hundreds of microRNAs compared with tens of thousands of mRNAs). Many normalization methods assume that mRNA intensity distributions are invariant over disease or experimental conditions but it is not at all clear that this assumption is valid for microRNAs.

A widely accepted and well validated method for normalizing mRNA microarrays is the use of housekeeping genes, i.e., genes that are expressed at constant levels in all samples. But there are no well-established housekeeping microRNAs that could be used in a similar way for microRNA arrays. For applications such as quantitative PCR, other non-coding housekeeping genes such as nucleolar RNAs have been used, but their variability under different conditions is significant and extensive testing has to be performed before they can be used as "housekeepers." To overcome this problem, a method was devised for the identification of microRNAs that can serve as housekeepers in the disclosed dataset. This method, which is described in detail in Example 1, essentially involves searching for microRNAs whose behavior is consistent with a housekeeping role; specifically, microRNAs whose expression levels vary in synchrony over all arrays, as would be expected if their expression levels were constant. Confining the search to those microRNAs that were scored as present on all arrays (132 in all), a set of 27 such microRNAs were found (FIG. 2A). The existence of such a large set of microRNAs behaving in this way is consistent with their role as housekeepers and is difficult to explain by any other mechanism.

To confirm the efficacy of this normalization method, a correlation test proposed by Ploner et al. (*BMC Bioinformatics* 6:80, 2005) was carried out to assess normalization methods for mRNA arrays. This test is based on the assumption that if one chooses two genes at random it is highly unlikely that their expression levels will be correlated with each other. In other words, while some pairs of genes unquestionably are biologically related, the vast majority of pairs are not. This means that if one calculates the Pearson correlation coefficients for the expression levels of all pairs of genes over all microarrays, a properly normalized data set will yield a distribution of correlation coefficients centered near zero. The presence of poorly normalized arrays will introduce an artifactual correlation (since all signals will be increased or decreased in concert) that will skew this distribution. FIG. 2B illustrates the results of such a calculation for the disclosed microRNA arrays before and after normalization with housekeeper microRNAs. Normalization clearly improves the symmetry and the centeredness of this distribution about zero, consistent with the hypothesis that the microRNAs listed in FIG. 2A behave as housekeepers.

Classification of Healthy and Disease Subsets i) Principal Component Analysis

Principal component analysis (PCA) is a mathematical method for reducing the dimensionality of a data set while retaining most of the variation. In the case of microarray data, the first principal component is a linear combination of expression patterns that accounts for the greatest amount of variability in the data. The second principal component is independent of the first and accounts for the greatest amount of remaining variability, and so on. Thus, PCA provides an unsupervised analysis that allows one to visualize a multidimensional data set in 2 or 3 dimensions that retain much of the experimental variability. FIG. 3 shows the results of a PCA analysis of the salivary microRNA arrays. Each point represents an array plotted according to its coordinates along the first 3 principal components. This analysis shows a clear separation of all SS samples (small and large circles) from healthy controls (medium circles) as well as a separation of low focus score (large circles) and high focus score (small circles) samples from one another. Thus, this analysis provides strong evidence that these various groups can be distinguished according to their microRNA profiles.

ii) Hierarchical Clustering

Figure 4:
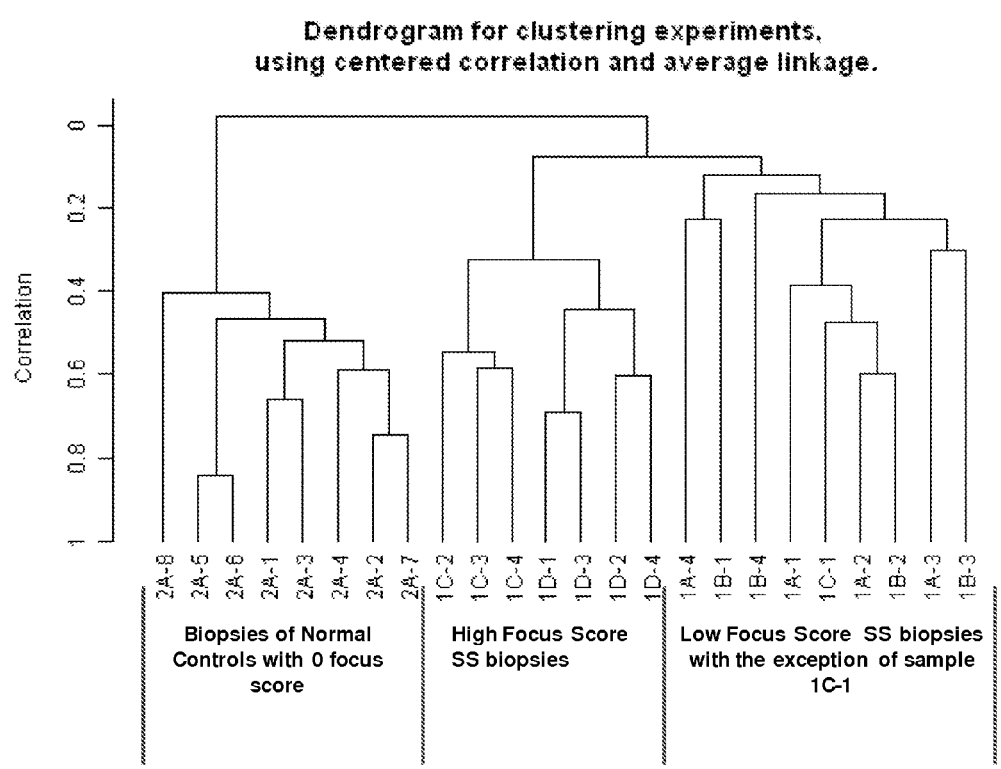
FIG. 4 is a dendrogram showing hierarchical clustering of microRNA arrays. There is a clear separation of the normal controls from the SS samples and a separation between high and low focus score SS samples with only one patient (1C-1) with high focus score clustering with the low focus score samples. In the high focus score group patients with low or preserved salivary flow form distinct clusters: 1A—SS patients with low focus scores and preserved salivary flow; 1A, 1B—SS patients with low focus scores; 1C, 1D—SS patients with high focus scores; 2A—healthy controls. The dendrogram was exported from BRB ArrayTools.

Next, hierarchical clustering of the normalized microarray expression data was performed. Hierarchical clustering, another unsupervised classification method, identifies clusters by merging the samples determined by a defined measure of pair-wise similarity of microRNA expression. Average linkage clustering was used, in which the distance between two clusters is calculated as the average of the distances between all pairs of elements. Similar to PCA, there is a distinct separation of minor salivary gland samples from healthy controls from both high and low focus score SS samples (FIG. 4). The separation of healthy tissue from samples with a high focus score was not surprising since they represent tissues with very different cellular composition. However, the clear distinction of healthy from low focus score tissues indicates that microRNA profiles are sensitive enough to distinguish between minor salivary glands with minimal histologic differences. Moreover, not only did miRNA profiles distinguish well between samples with different degrees of inflammation, they clearly separated samples with preserved or decreased salivary flows in the high focus score samples.

iii) Class Prediction Using Differentially Expressed MicroRNAs

Next it was tested whether differentially expressed microRNAs could predict healthy versus SS class membership. Various prediction algorithms (namely Compound Covariate Predictor, Diagonal Linear Discriminant Analysis, 1-Nearest Neighbor, 3-Nearest Neighbors, Nearest Centroid, Support Vector Machines and Bayesian Compound Covariate Predictor) all correctly classified subjects as patients or healthy controls in 100% of cases yielding both sensitivity and specificity of 1.0 (Table 7). The classifier was composed of 58 microRNAs that were significantly different between the classes at the 0.001 significance level. The leave-one-out cross-validation method was used to compute misclassification rate.

iv) Validation of Potential Biomarkers

Figure 5:
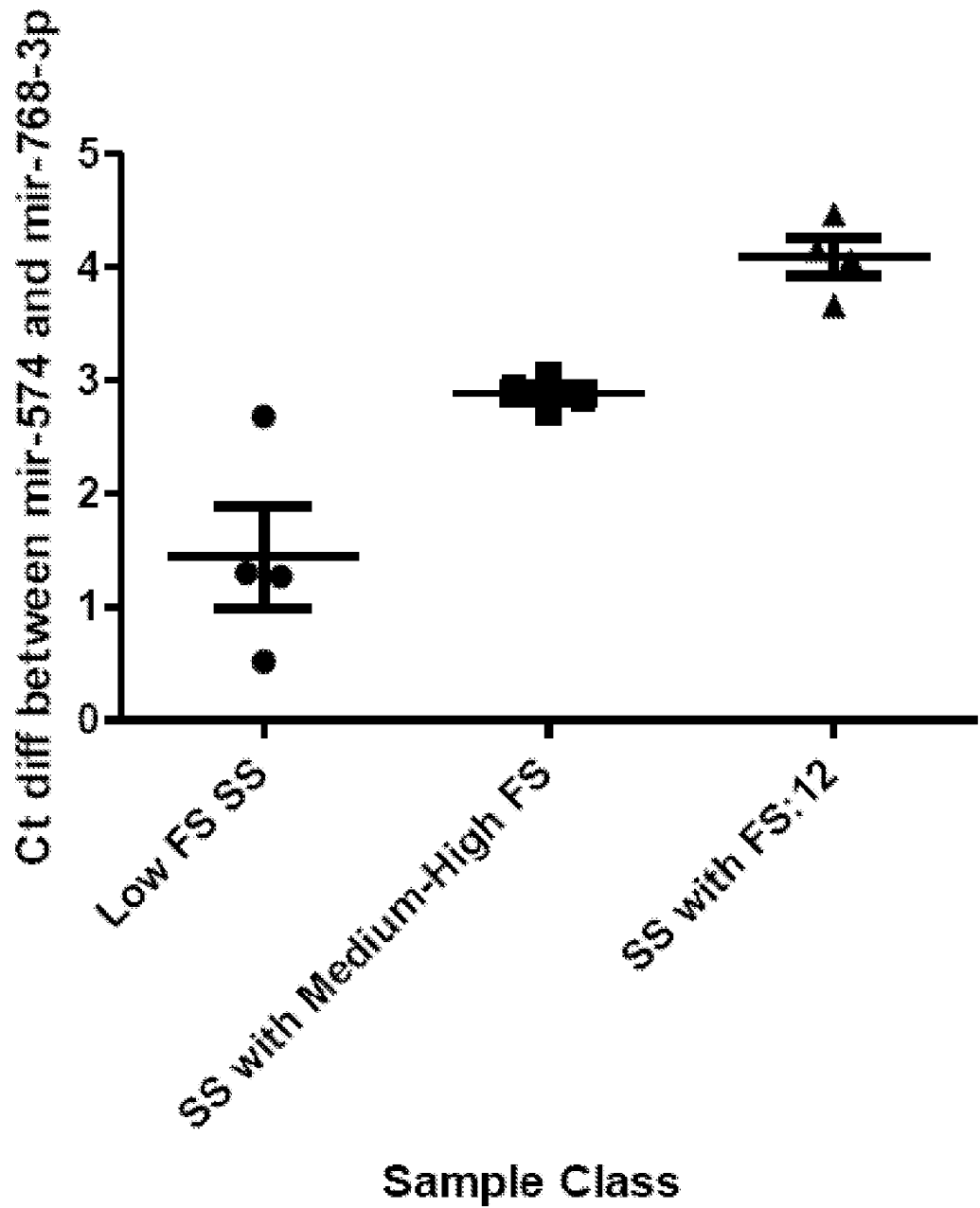
FIG. 5 is a graph showing relative expression of selected microRNAs correlate with minor salivary gland focus scores. From the normalized dataset, two microRNAs were identified that have distinct and opposite expression patterns between normal, low and high focus score samples; miR-768-3p increases whereas miR-574 decreases with increasing focus score. The expression patterns of these two microRNAs were validated by real-time quantitative PCR in an independent set of samples (n=15) with various focus scores by monitoring their relative expression levels in the exact same samples via determining their cycle difference (Ct diff). There was a statistically significant difference in the Ct differences among low focus score (FS: 0-2) samples, medium focus score (FS: 5-7) samples and high focus score (FS: 12) samples (p=0.0003, based on one-way ANOVA).

To confirm the differences observed on microarrays and to assess the potential of using selected microRNAs to distinguish between subgroups of Sjögren's patients, two microRNAs were identified that changed in opposite directions among the normal, low and high focus score groups. One of these microRNAs (hsa-miR-768-3p) increased and the other (hsa-miR-574) decreased with increasing focus score. In the experiments illustrated in FIG. 5, the feasibility of using the expression patterns of these two microRNAs as predictors of focus score was tested in a set of fifteen samples independent of those used for the microarray studies. Shown are the Ct differences between these 2 microRNAs determined simultaneously in the same samples using TaqMan™ Real Time PCR. A statistically significant difference was found in these Ct differences among low focus score (FS: 0-2), medium focus score (FS: 5-7) and high focus score samples (FS: 12). It is important to point out that the Ct difference is a measure of the ratio of the expressions of these two microRNAs and thus is independent of sample normalization.

Biologic Targets of Differentially Expressed MicroRNAs Discriminating Among Normal, Low Focus Score SS and High Focus Score SS Classes In addition to showing a strong association with clinical characteristics, such as diagnosis, disease activity or tissue damage, a reliable biomarker has to reflect an important underlying physiologic process. Therefore, the potential biological significance of these findings was assessed by identifying the physiologic processes, which may be effected by the differentially expressed microRNAs. First, the microRNAs that were most significantly differentially expressed among the various clinical groups were identified. This was accomplished using the Class Comparison algorithm of BRB Array-Tools set to allow a maximum of one false positive with a confidence level of 75%. This yielded 94 microRNAs that were differentially expressed among the healthy, low focus score SS and high focus score SS groups ($p<0.01$) (Table 19).

TABLE 19

List of microRNAs that were significantly differentially expressed ($p < 0.01$) among the various clinical groups

| microRNA array ID | Mature microRNA ID | Parametric p-value | Geom mean of intensities in HF | Geom mean of intensities in LF | Geom mean of intensities in NC |
| --- | --- | --- | --- | --- | --- |
| hsa-miR-126* | MIMAT0000444 | <1e−07 | 162.0 | 55.9 | 1.0 |
| hsa-miR-768-3p | MIMAT0003947 | <1e−07 | 4058.5 | 2510.9 | 572.8 |
| hsa-miR-30b | MIMAT0000420 | <1e−07 | 396.6 | 558.5 | 98.5 |
| hsa-miR-342 | MIMAT0000753 | <1e−07 | 530.5 | 175.5 | 61.5 |
| hsa-miR-150 | MIMAT0000451 | <1e−07 | 931.3 | 122.4 | 3.2 |
| hsa-miR-564 | MIMAT0003228 | <1e−07 | 90.0 | 65.5 | 2.2 |
| hsa-miR-574 | MIMAT0003239 | <1e−07 | 120.2 | 236.6 | 508.8 |
| hsa-miR-93 | MIMAT0000093 | <1e−07 | 272.8 | 225.7 | 122.5 |
| hsa-miR-155 | MIMAT0000646 | <1e−07 | 903.9 | 157.2 | 161.7 |
| hsa-miR-768-5p | MIMAT0003946 | <1e−07 | 416.7 | 202.0 | 1701.4 |
| hsa-miR-222 | MIMAT0000279 | <1e−07 | 827.9 | 491.0 | 259.2 |

TABLE 19-continued

List of microRNAs that were significantly differentially expressed (p < 0.01) among the various clinical groups

| microRNA array ID | Mature microRNA ID | Parametric p-value | Geom mean of intensities in HF | Geom mean of intensities in LF | Geom mean of intensities in NC |
|---|---|---|---|---|---|
| hsa-miR-146b | MIMAT0002809 | <1e−07 | 395.9 | 135.5 | 107.8 |
| hsa-miR-509 | MIMAT0002881 | 1.00E−07 | 18.5 | 21.0 | 1.0 |
| hsa-miR-565 | MIMAT0003229 | 1.00E−07 | 1411.7 | 1708.4 | 179.3 |
| hsa-miR-30c | MIMAT0000244 | 1.00E−07 | 206.7 | 275.5 | 112.5 |
| hsa-miR-16 | MIMAT0000069 | 2.00E−07 | 3888.9 | 2217.4 | 1627.9 |
| hsa-miR-324-3p | MIMAT0000762 | 2.00E−07 | 498.4 | 242.5 | 139.7 |
| hsa-miR-205 | MIMAT0000266 | 2.00E−07 | 2145.2 | 2472.7 | 768.9 |
| hsa-miR-223 | MIMAT0000280 | 3.00E−07 | 639.1 | 252.6 | 323.2 |
| ebv-miR-BART19 | MIMAT0003718 | 5.00E−07 | 1206.8 | 482.4 | 5.2 |
| hsa-miR-200c | MIMAT0000617 | 6.00E−07 | 4470.4 | 8255.2 | 16585.5 |
| hsa-miR-221 | MIMAT0000278 | 6.00E−07 | 241.9 | 182.6 | 105.8 |
| hsa-miR-199a | MIMAT0000231 | 8.00E−07 | 943.8 | 760.5 | 370.1 |
| hsa-miR-22 | MIMAT0000077 | 8.00E−07 | 2848.9 | 3422.6 | 8234.6 |
| hsa-miR-198 | MIMAT0000228 | 1.10E−06 | 52.3 | 32.9 | 2.1 |
| hsa-miR-363 | MIMAT0000707 | 1.30E−06 | 214.5 | 397.5 | 663.7 |
| ebv-miR-BART13 | MIMAT0003424 | 1.40E−06 | 225.9 | 251.3 | 10.5 |
| hsa-miR-548c | MIMAT0003285 | 1.50E−06 | 1.0 | 1.0 | 6.5 |
| hsa-miR-28 | MIMAT0000085 | 2.00E−06 | 193.0 | 249.0 | 457.4 |
| hsa-miR-513 | MIMAT0002877 | 2.80E−06 | 189.5 | 60.4 | 3.7 |
| hsa-miR-200b | MIMAT0000318 | 3.20E−06 | 2185.8 | 4232.4 | 6376.6 |
| hsa-miR-152 | MIMAT0000438 | 4.70E−06 | 249.9 | 480.9 | 533.9 |
| hsa-miR-560 | MIMAT0003224 | 4.80E−06 | 20.5 | 7.2 | 1.0 |
| kshv-miR-K12-3 | MIMAT0002193 | 8.60E−06 | 224.4 | 222.5 | 52.2 |
| hsa-miR-145 | MIMAT0000437 | 1.53E−05 | 6158.0 | 10949.4 | 14804.6 |
| hsa-miR-148a | MIMAT0000243 | 1.67E−05 | 5417.0 | 14461.4 | 16675.9 |
| hsa-miR-601 | MIMAT0003269 | 2.25E−05 | 27.3 | 13.2 | 1.7 |
| hsa-miR-335 | MIMAT0000765 | 2.38E−05 | 169.9 | 387.6 | 409.6 |
| hsa-miR-21 | MIMAT0000076 | 2.79E−05 | 15529.1 | 6327.6 | 9454.3 |
| hsa-miR-142-5p | MIMAT0000433 | 4.77E−05 | 2067.8 | 442.5 | 221.6 |
| hsa-miR-374 | MIMAT0000727 | 5.10E−05 | 369.4 | 350.6 | 138.4 |
| hsa-miR-494 | MIMAT0002816 | 5.98E−05 | 2365.9 | 1968.2 | 231.0 |
| hsa-miR-801 | MIMAT0004209 | 6.77E−05 | 307.7 | 126.0 | 15.3 |
| hsa-miR-575 | MIMAT0003240 | 7.00E−05 | 396.1 | 208.8 | 16.9 |
| hsa-miR-200a | MIMAT0000682 | 7.59E−05 | 1390.8 | 3055.7 | 4242.1 |
| hsa-miR-339 | MIMAT0000764 | 8.46E−05 | 74.8 | 90.7 | 160.1 |
| hsa-miR-181a | MIMAT0000256 | 9.01E−05 | 253.6 | 158.6 | 99.3 |
| hsa-miR-375 | MIMAT0000728 | 0.0001075 | 709.1 | 2280.2 | 2912.8 |
| hsv1-miR-H1 | MIMAT0003744 | 0.0001132 | 27.0 | 13.9 | 1.8 |
| hsa-miR-135b | MIMAT0000758 | 0.0001225 | 31.8 | 8.0 | 1.0 |
| hsa-miR-202 | MIMAT0002811 | 0.0001272 | 94.9 | 97.9 | 17.1 |
| hsa-miR-132 | MIMAT0000426 | 0.0001862 | 40.4 | 25.2 | 5.3 |
| hsa-miR-31 | MIMAT0000089 | 0.0002232 | 75.9 | 48.5 | 7.0 |
| hsa-miR-429 | MIMAT0001536 | 0.0002247 | 320.4 | 641.7 | 687.0 |
| hsa-miR-299-3p | MIMAT0000687 | 0.0003133 | 1.8 | 18.3 | 2.6 |
| hcmv-miR-US4 | MIMAT0003341 | 0.0003432 | 20.7 | 35.0 | 3.2 |
| hsa-miR-188 | MIMAT0000457 | 0.0003456 | 107.6 | 82.8 | 10.6 |
| hsa-miR-128a | MIMAT0000424 | 0.0003461 | 25.7 | 21.4 | 4.8 |
| hsa-miR-128b | MIMAT0000676 | 0.0003864 | 32.7 | 25.1 | 5.3 |
| hsa-miR-584 | MIMAT0003249 | 0.0004106 | 8.3 | 12.3 | 1.2 |
| hsa-miR-143 | MIMAT0000435 | 0.0004164 | 3491.9 | 7605.7 | 8650.5 |
| hsa-miR-99b | MIMAT0000689 | 0.0004223 | 91.1 | 64.9 | 12.0 |
| hsa-miR-452 | MIMAT0001635 | 0.0004492 | 47.4 | 29.9 | 4.3 |
| hsa-miR-424 | MIMAT0001341 | 0.0004508 | 227.3 | 437.1 | 770.2 |
| hsa-miR-625 | MIMAT0003294 | 0.000503 | 42.3 | 23.8 | 47.1 |
| hsa-miR-487b | MIMAT0003180 | 0.0005041 | 68.5 | 110.6 | 48.8 |
| hsa-miR-455 | MIMAT0003150 | 0.0005541 | 7.0 | 11.3 | 1.0 |
| hsa-miR-370 | MIMAT0000722 | 0.0008064 | 438.5 | 300.3 | 77.3 |
| hsa-miR-338 | MIMAT0000763 | 0.0012512 | 79.0 | 287.8 | 312.0 |
| hsa-miR-142-3p | MIMAT0000434 | 0.0017266 | 4776.0 | 939.8 | 824.4 |
| hsa-miR-200a* | MIMAT0001620 | 0.0018568 | 13.0 | 32.0 | 55.1 |
| hsa-miR-622 | MIMAT0003291 | 0.0019099 | 12.4 | 4.7 | 1.0 |
| hsa-miR-382 | MIMAT0000737 | 0.0019676 | 8.9 | 12.8 | 2.6 |
| hsa-miR-368 | MIMAT0000720 | 0.0023573 | 68.5 | 127.3 | 106.9 |
| hsa-miR-210 | MIMAT0000267 | 0.0025901 | 100.6 | 178.5 | 160.3 |
| hsa-miR-501 | MIMAT0002872 | 0.0027201 | 20.6 | 6.9 | 2.9 |
| hsa-miR-585 | MIMAT0003250 | 0.0028392 | 1.0 | 1.3 | 5.2 |
| hsa-miR-369-5p | MIMAT0001621 | 0.0030675 | 1.3 | 7.6 | 2.3 |
| hsa-miR-650 | MIMAT0003320 | 0.0033436 | 49.3 | 7.2 | 4.6 |
| hsa-miR-299-5p | MIMAT0002890 | 0.0038794 | 14.8 | 39.8 | 48.5 |
| hsa-miR-409-3p | MIMAT0001639 | 0.0039263 | 12.8 | 24.2 | 3.6 |
| hsa-miR-330 | MIMAT0000751 | 0.0040909 | 11.7 | 3.3 | 1.6 |
| hsa-miR-140 | MIMAT0000431 | 0.0045103 | 216.2 | 185.7 | 345.8 |

TABLE 19-continued

List of microRNAs that were significantly differentially expressed (p < 0.01) among the various clinical groups

| microRNA array ID | Mature microRNA ID | Parametric p-value | Geom mean of intensities in HF | Geom mean of intensities in LF | Geom mean of intensities in NC |
|---|---|---|---|---|---|
| hsa-miR-149 | MIMAT0000450 | 0.0047885 | 16.7 | 39.4 | 63.2 |
| hsa-miR-329 | MIMAT0001629 | 0.0048856 | 1.0 | 3.0 | 1.0 |
| hsa-miR-379 | MIMAT0000733 | 0.0053442 | 20.3 | 55.0 | 83.7 |
| hsa-miR-194 | MIMAT0000460 | 0.0055898 | 19.1 | 24.1 | 4.3 |
| hsa-miR-376b | MIMAT0002172 | 0.0059764 | 2.9 | 17.5 | 2.7 |
| hsa-miR-381 | MIMAT0000736 | 0.0062613 | 32.3 | 66.7 | 43.7 |
| hsa-miR-766 | MIMAT0003888 | 0.0075524 | 55.8 | 19.7 | 14.2 |
| hsa-miR-10a | MIMAT0000253 | 0.0084362 | 45.0 | 34.5 | 8.0 |
| hsa-miR-484 | MIMAT0002174 | 0.0087041 | 73.8 | 45.3 | 20.3 |
| hsa-miR-154 | MIMAT0000452 | 0.0087539 | 17.0 | 29.8 | 5.1 |
| hsa-miR-377 | MIMAT0000730 | 0.0094478 | 61.7 | 217.2 | 145.7 |

The BRB ArrayTools class comparison algorithm was used, set to allow a maximum of one false positive with a confidence level of false discovery of 75%. The univariate F-test was run, and the multivariate permutation test was computed based on 1000 permutations.
HF, high focus score group;
LF, low focus score group;
NC, normal controls.

To separate miRNAs that are associated with inflammation from those that change independent from the number of lymphocytic foci, two major patterns were primarily evaluated (Table 20):
A. Non-inflammatory pattern (n=13): microRNAs in this group increased >5-fold between the Healthy and Low Focus score groups but were essentially unchanged (increased or decreased <50%) between the Low and High Focus score groups (i.e., their expression levels did not correlate with inflammation).
B. Inflammatory pattern (n=10): microRNAs in this group increased >50% between Healthy controls and Low Focus Score and also increased >2.5-fold between Low and High Focus Score groups (i.e., their expression levels consistently increased with inflammation).

TABLE 20

Class comparison among Normal, SS low focus score (Low FS), and SS high focus score (High FS) samples

| Unique id | Geom mean of intensities in Normal | Geom mean of intensities in Low FS | Geom mean of intensities in High FS |
|---|---|---|---|
| A. Non-inflammatory microRNA expression pattern. The following miRNAs increase >5-fold between Low Focus and Normal but increase or decrease <50% between Low Focus and High Focus. | | | |
| hsa-miR-564 | 2.2 | 65.5 | 90.0 |
| ebv-miR-BART13 | 10.5 | 251.3 | 225.9 |
| hsa-miR-509 | 1.0 | 21.0 | 18.5 |
| hcmv-miR-US4 | 3.2 | 35.0 | 20.7 |
| hsa-miR-565 | 179.3 | 1708.4 | 1411.7 |
| hsa-miR-494 | 231.0 | 1968.2 | 2365.9 |
| hsa-miR-188 | 10.6 | 82.8 | 107.6 |
| hsa-miR-409-3p | 3.6 | 24.2 | 12.8 |
| hsa-miR-154 | 5.1 | 29.8 | 17.0 |
| hsa-miR-202 | 17.1 | 97.9 | 94.9 |
| hsa-miR-30b | 98.5 | 558.5 | 396.6 |
| hsa-miR-194 | 4.3 | 24.1 | 19.1 |
| hsa-miR-99b | 12.0 | 64.9 | 91.1 |
| B. Inflammatory microRNA expression pattern. The following miRNAs increase >50% between Normal and Low focus score and >2.5-fold between Low and High Focus. | | | |
| hsa-miR-150 | 3.2 | 122.4 | 931.3 |
| hsa-miR-650 | 4.6 | 7.2 | 49.3 |

TABLE 20-continued

Class comparison among Normal, SS low focus score (Low FS), and SS high focus score (High FS) samples

| Unique id | Geom mean of intensities in Normal | Geom mean of intensities in Low FS | Geom mean of intensities in High FS |
|---|---|---|---|
| hsa-miR-142-5p | 221.6 | 442.5 | 2067.8 |
| hsa-miR-135b | 1.0 | 8.0 | 31.8 |
| hsa-miR-330 | 1.6 | 3.3 | 11.7 |
| hsa-miR-513 | 3.7 | 60.4 | 189.5 |
| hsa-miR-342 | 61.5 | 175.5 | 530.5 |
| hsa-miR-501 | 2.9 | 6.9 | 20.6 |
| hsa-miR-126* | 1.0 | 55.9 | 162.0 |
| ebv-miR-BART19 | 5.2 | 482.4 | 1206.8 |

Differentially expressed microRNAs were identified using the BRB ArrayTools class comparison algorithm set to allow a maximum of one false positive with a confidence level of false discovery of 75%. The complete set of 94 differentially expressed microRNAs with p < 0.01 are listed in Table 19.
The geometric (Geom) means for each sample group are shown.

Figure 6A:
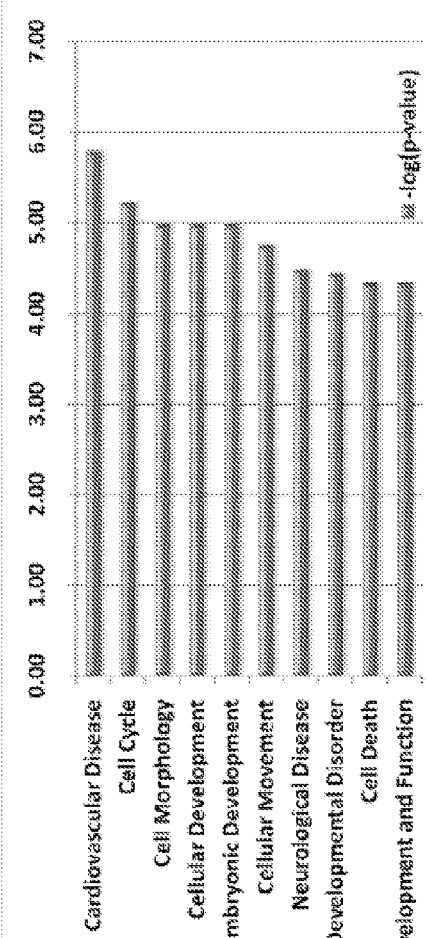
FIGS. 6A and 6B are graphs showing the ten most significant biological functions by Ingenuity Pathway Analysis for the genes targeted by the non-inflammatory (A) and inflammatory (B) group of microRNAs from Table 20.
Figure 6B:
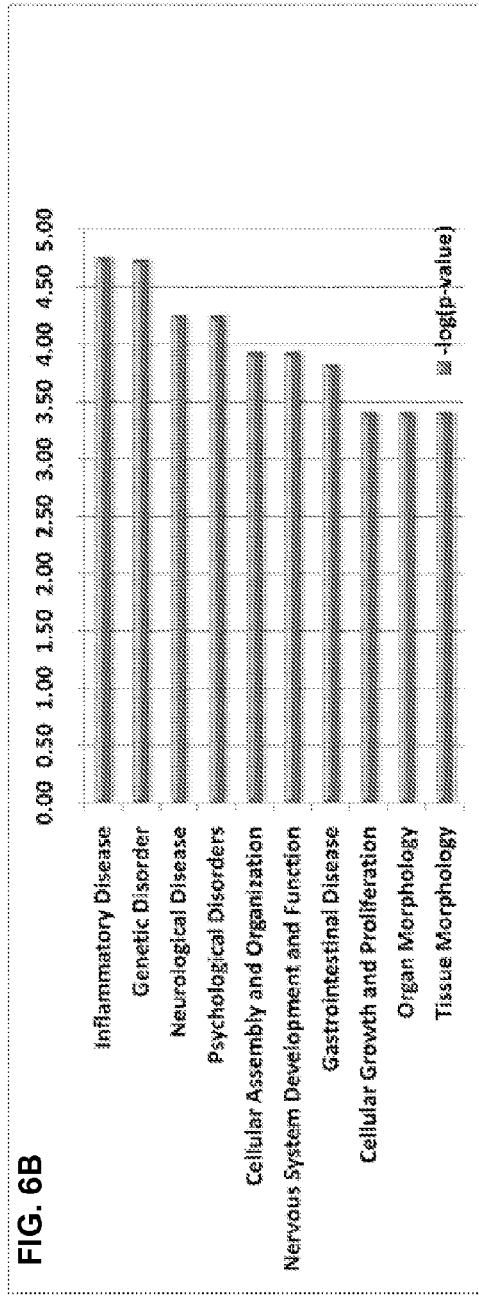

It was hypothesized that microRNAs from the non-inflammatory pattern would target pathways that are not related to increased inflammation in SS but rather are related to other aspects of the disease process. To test this hypothesis, the predicted mRNA targets of these microRNAs were identified using the RNA22 target prediction algorithm (Miranda et al., Cell 126:1203-1217, 2006), then the Ingenuity Pathway Analysis software was used to predict the physiologic networks and functions those microRNAs might be targeting. To reduce the possibility of the identification of spurious pathways arising from multiple microRNA targets, only those mRNAs that were predicted to be targeted by at least 3 of the microRNAs in the non-inflammatory group were included. The resulting top statistically significant biologic functions included pathways involved in cardiovascular disease, cell cycle, cell morphology and cell development (FIG. 6A). A similar analysis using the microRNAs of the inflammatory group identified pathways involved in immunological, neurologic, genetic and psychological diseases and cellular assembly and organization (FIG. 6B).

Differentially Expressed MicroRNAs Discriminating Between Preserved and Low Salivary Flow in Salivary Glands with a High Focus Score To further explore if specific microRNAs are associated with decreased function in the setting of intense inflammation, patients with high focus scores were compared with either preserved or low salivary flows. As expected from the hierarchical clustering analysis (FIG. 4), there were a number of miRNAs that were differentially expressed in the high focus score group between normal and preserved salivary flow (Table 21).

TABLE 21

MicroRNAs differentially expressed in minor salivary glands of patients with high focus score and either preserved or low salivary function

| Unique ID | Mature Name |
|---|---|
| hsa-miR-101 | MIMAT0000099 |
| hsa-miR-136 | MIMAT0000448 |
| hsa-miR-141 | MIMAT0000432 |
| hsa-miR-142-3p | MIMAT0000434 |
| hsa-miR-144 | MIMAT0000436 |
| hsa-miR-18a | MIMAT0000072 |
| hsa-miR-193a | MIMAT0000459 |
| hsa-miR-19a | MIMAT0000073 |
| hsa-miR-19b | MIMAT0000074 |
| hsa-miR-212 | MIMAT0000269 |
| hsa-miR-29b | MIMAT0000100 |
| hsa-miR-301 | MIMAT0000688 |
| hsa-miR-30e-5p | MIMAT0000692 |
| hsa-miR-33 | MIMAT0000091 |
| hsa-miR-374 | MIMAT0000727 |
| hsa-miR-377 | MIMAT0000730 |
| hsa-miR-590 | MIMAT0003258 |
| hsa-miR-565 | MIMAT0003229 |
| hsa-miR-770-5p | MIMAT0003948 |
| hsa-miR-15a | MIMAT0000068 |
| hsa-miR-17-3p | MIMAT0000071 |
| hsa-miR-181c | MIMAT0000258 |
| hsa-miR-29c | MIMAT0000681 |
| hsa-miR-338 | MIMAT0000763 |

Interestingly, all of these 24 microRNAs are downregulated in the group with decreased function, suggesting that an overexpression of their targets may have a negative effect on epithelial cells. It is also intriguing that four of these differentially expressed microRNAs belong to the mir-17-92 cluster which is associated with specific subsets of inflammatory cells.

Example 5

Exosomes from Human Saliva as a Source of MicroRNA Biomarkers

This example describes an exemplary protocol for isolating miRNAs from exosomes from human saliva (see also Michael et al., *Oral Dis.* 16:34-38, 2010).
Methods
Research Subjects
Subjects were enrolled in a protocol for healthy volunteers or in a study of the natural history of Sjögren's syndrome.
Saliva Collection
To stimulate glandular salivary flow, patients received a 2% citric acid solution to the posterior lateral surfaces of the tongue, applied bilaterally with a cotton swab for 5 seconds every 30 seconds. The citric acid stimulation continued for 30-second intervals during the entire collection procedure. Parotid saliva was collected as follows. Carlson Crittenden parotid collectors were placed bilaterally on the opening of Stenson's duct orifice on the buccal mucosa opposite the upper second molar tooth. The parotid collectors were positioned on the mucosa so that the inner ring surrounded the duct orifice. Suction from the outer ring held the collector on the mucosa, with a vacuum created by squeezing and holding the deflated bulb during placement over the duct orifice and subsequent release of the bulb when the cup was in place. Submandibular/sublingual saliva was collected as follows. With the orifices of the parotid ducts covered by the collectors, after applying 2% citric acid on the tongue at least 5 times, the floor of the mouth was dried and saliva was collected with gentle suction into a tube on ice for 20 seconds. The collection was then stopped, a 2×2 gauze was placed over the orifice of the submandibular ducts and 2% citric acid was applied on the tongue. Saliva was collected in the same tube with gentle suction and the collection was stopped again with gauze. The whole process was repeated up to 8 times.
Salivary Exosome Isolation
The protocol for salivary exosome isolation was adapted and modified from a previous method for urinary exosome isolation (Zhou et al., *Kidney Int* 74: 613-621, 2008). Immediately after collection, saliva was placed on ice, transferred to the laboratory and centrifuged at 1500 g for 10 minutes at 4° C. The supernatant was then removed, placed in another tube and centrifuged at 17,000 g for 15 minutes at 4° C. to further remove unwanted organelles and cell fragments. Following initial centrifugation steps, the supernatant was transferred to sterile tubes for ultracentrifugation at 160,000 g for 1 hour at 4° C. Following ultracentrifugation, the aqueous layer, which is viscous in whole saliva samples, was removed and the pellet containing the exosomes was washed with PBS and ultracentrifuged again at 160,000 g for 1 hour at 4° C. After the end of the second ultracentrifugation, the supernatant was removed and the pellet was briefly allowed to dry. The samples were then ready for protein or RNA isolation.
Protein Isolation and Western Blotting
Prior to exosome protein analysis, a stock solution of isolation buffer was made by mixing 10 mM triethanolamine, 250 mM sucrose and deionized water. The isolation buffer pH was then adjusted to pH 7.6 with 1N sodium hydroxide. Deionized water was added to bring the total volume of the isolation buffer stock solution to 50 mL. Solution was stored at –20° C. Protease inhibitors were added to 1 mL of isolation buffer just prior to use (50 microliters of phenylmethylsulphonyl fluoride (2 mg/ml) and 10 microliters of leupeptin (1 mg/ml), both stored at –20° C.). Following exosome isolation, the pellet was resuspended in 100 microliters of isolation buffer containing the protease inhibitors. An equal volume of 2× Laemmli buffer (Biorad, Hercules, Calif.) was added and the sample was denatured at 60° C. for 10 minutes. Presence of TSG101 was determined with Western blotting. The samples were subjected to NuPAGE Novex 4-12% Bis-Tris Gel (Invitrogen, Carlsbad Calif., USA). The protein was transferred onto membranes using a semidry transfer unit. Western blotting was performed with TSG101 antibody (Abcam, (ab83), Cambridge, Mass.) diluted 1:7500.
RNA Isolation and Analysis
Following exosome isolation, the pellet was treated with RNase A to degrade any residual cellular RNAs in order to ensure that all detected RNA was exosomal in origin. Some samples were treated with RNase A (Puregene-Gentra Systems, Valencia, Calif.), 4 mg/ml solution, working concentration of 0.4 mg/ml in deionized water for 10 minutes at 37° C. The sample exosomes were then lysed with 600 microliters of miRNeasy lysis buffer (Qiagen, Valencia, Calif., USA) and stored at –80° C. for later use or immediately processed using Qiagen's miRNeasy Kit according to the manufacturer's protocol. All RNA samples were eluted in 50 microliters of RNase free water. To aid in the concentration and precipitation of exosomal RNA, Novagen's pellet paint was used according to the manufacturer's protocol with minor modifications; two microliters of pellet paint was added to the RNA samples. Following pellet paint addition, 0.1 volumes of 3M sodium acetate was added to the sample and the sample was mixed for 10 seconds. After mixing, 2.5 volumes of 100% ethanol were added to the sample and vortexed briefly. The sample was then incubated at room temperature for two minutes and centrifuged for five minutes at 4° C. Following centrifugation, the pellet containing exosomal RNA was washed with 200 microliters of 70% ethanol and allowed to air dry prior to resuspension in RNase free water. RNA was then quantitated using a UV-Vis spectrophotometer (Nanodrop 8000) and quality was assessed using the Agilent 2100 Bioanalyzer, where the presence of small RNAs was verified in both RNase-treated and untreated samples.

After the isolation and quantitation of the exosomal RNA, five nanograms of input RNA were used for a reverse transcription reaction with the TAQMAN™ MicroRNA Reverse Transcription Kit (Applied Biosystems). Gene-specific primers to hsa-mir-203, hsa-mir-768-3p and hsa-mir-574-3p were used in separate reactions. A positive control reverse transcription reaction with the small nucleolar RNA U48 was performed using specific primers. Negative controls using 5 microliters of water in place of the RNA were performed alongside each reaction. cDNA obtained from the reverse transcription reactions were stored at −20° C. or immediately used for real-time quantitative PCR. Real-time quantitative PCR was used to detect and quantify microRNAs of interest. All samples were run in triplicate using 5 ng of cDNA for each reaction as described by the manufacturer's protocol.

Microarray Studies

Microarray hybridization was performed using the Exiqon miRNA microarray system (miRCURY LNA™ microRNA Array, v.10.0) on exosomal miRNAs isolated from parotid and submandibular gland saliva, as well as from parotid salivary exosomal miRNAs from Sjögren's syndrome patient. Sample labeling and hybridization were performed as described in the manufacturer's protocol with the exception that starting material used was on the lower limit than the array manufacturer recommends. Briefly, miRNA spike-in controls were added to 250 ng of salivary exosomal microRNAs and were treated with calf intestinal phosphatase. The samples were then labeled with either Hy3 or Hy5, denatured, hybridized on the array at 56° C. for 16 hours, washed and scanned on an Agilent scanner (Model G2505B). Data were processed with the Feature Extraction algorithm of Agilent.

Results

Saliva samples ranging from 200 µl up to 5 mL volume yielded an adequate amount of exosomal RNA for quantitative PCR. microRNAs were isolated from even smaller volumes of saliva, but the RNA yield was sufficient for only for a small number of quantitative PCR reactions. It was also possible to isolate exosomes from saliva that was frozen at −20° C. for 7 days. Although it is possible to isolate exosomes from both glandular and whole saliva, the viscosity and cellular contamination of whole saliva make it a less than ideal medium for exosomal isolation. Therefore, this study primarily focused on glandular saliva only.

To verify the presence of exosomes in the pellet after the series of centrifugations, pellets were lysed from both submandibular and parotid saliva, and the presence of TSG101, a standard exosomal marker, was confirmed by Western blot. In order to assess the microRNA content of exosomes, and to ensure that isolated miRNAs originated from within the exosomes, the exosomal pellets were treated with RNaseA, as described above, and then miRNA was isolated from exosomal lysates with a kit that also preserved mRNA. The total concentration of RNA that was isolated varied among individuals, with an average of 20.9 ng per 100 µl for parotid and 27.4 ng per 100 µl of submandibular saliva collected. Increased collection times did not increase the RNA concentration linearly; in continuous saliva collection, the first 100 µl collected consistently had a greater RNA concentration than the subsequent 100 µl. It is hypothesized that the exosomes present in the cell are released in the saliva promptly upon stimulation and are collected quickly by this method. Once this extant supply is exhausted, the de novo synthesis of exosomes requires longer periods than the saliva collection times.

To confirm the presence of microRNAs within the exosomes, TaqMan™ microRNA quantitative PCR amplification was performed for three microRNAs (hsa-miR-203, hsa-miR-768-3p and hsa-miR-574-3p) that were previously identified as present in minor salivary glands, as well as whole saliva. PCR reactions with negative and positive controls demonstrated the presence of microRNAs within the exosomes. For a more comprehensive view of what microRNAs might be present within the exosomes, two miRNA microarrays were run: one microarray was hybridized with microRNAs from parotid saliva against microRNAs from submandibular saliva from the same normal volunteer, and the second microarray was hybridized with miRNAs from parotid saliva from a normal volunteer against miRNAs from a Sjögren's syndrome patient saliva sample.

The results described herein demonstrate that exosomes can be readily isolated from saliva, and that these exosomes contain microRNAs in quantities adequate for both qPCR and microarray hybridization.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A method of treating a patient with Sjögren's syndrome, comprising administering to the patient a therapeutically effective amount of an agent that inhibits expression of a miR gene product that is up-regulated in the patient with Sjögren's syndrome relative to a control, or a therapeutically effective amount of an isolated miR gene product that is down-regulated in the patient with Sjögren's syndrome relative to a control, wherein the up-regulated miR gene product is ebv-miR-BART13 and the down-regulated miR gene product is miR-22 or miR-183.

2. The method of claim 1, wherein the agent that inhibits expression of a miR gene product is an antisense compound specific for the miR gene product.

3. The method of claim 2, wherein the antisense compound is an antisense oligonucleotide, siRNA or ribozyme.

4. The method of claim 1, wherein the down-regulated miR gene product is a miR-183 gene product.

5. The method of claim 1, wherein the treatment comprises restoring salivary flow in the subject with Sjögren's syndrome.

6. The method of claim 1, wherein the control is a biological sample from a healthy subject.

7. The method of claim 1, wherein the isolated miR gene product is a mature miR.

8. The method of claim 1, wherein the isolated miR gene product is a synthetic miR gene product.

9. The method of claim 1, wherein administering a therapeutically effective amount of the isolated miR gene product comprises administering a vector encoding the miR gene product.

10. The method of claim 1, wherein the down-regulated miR gene product is a miR-22 gene product.

11. The method of claim 2, wherein the antisense compound comprises one or more modifications.

12. The method of claim 11, wherein the one or more modifications comprise a modified internucleoside linkage, a modified sugar moiety, a modified base, or any combination thereof.

* * * * *